US012044675B2

(12) United States Patent
Looger et al.

(10) Patent No.: US 12,044,675 B2
(45) Date of Patent: Jul. 23, 2024

(54) GENETICALLY ENCODED CALCIUM INDICATORS (GECIS) AND METHODS OF MAKING AND USING

(71) Applicant: Howard Hughes Medical Institute, Chevy Chase, MD (US)

(72) Inventors: Loren L. Looger, Madison, AL (US); Yan Zhang, Ashburn, VA (US); Eric R. Schreiter, Leesburg, VA (US); Jeremy P Hasseman, Leesburg, VA (US); Ilya Kolb, Ashburn, VA (US);

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 17/483,800

(22) Filed: Sep. 23, 2021

(65) Prior Publication Data
US 2022/0365071 A1 Nov. 17, 2022

Related U.S. Application Data

(60) Provisional application No. 63/082,222, filed on Sep. 23, 2020.

(51) Int. Cl.
*G01N 33/50* (2006.01)
*A61B 5/00* (2006.01)
*C12N 15/62* (2006.01)
*C12N 15/85* (2006.01)

(52) U.S. Cl.
CPC ....... *G01N 33/5041* (2013.01); *A61B 5/0071* (2013.01); *C12N 15/62* (2013.01); *C12N 15/85* (2013.01); *A61B 2503/40* (2013.01); *C12N 2800/107* (2013.01)

(58) Field of Classification Search
CPC .... G01N 33/5041; C12N 15/62; C12N 15/85; C12N 2800/107
See application file for complete search history.

(56) References Cited

U.S. PATENT DOCUMENTS

| | | | |
|---|---|---|---|
| 6,133,502 A | 10/2000 | Kasuga et al. | |
| 6,175,057 B1 | 1/2001 | Mucke et al. | |
| 6,180,849 B1 | 1/2001 | Streuli et al. | |
| 8,629,256 B2 | 1/2014 | Looger et al. | |
| 9,488,642 B2 | 11/2016 | Looger et al. | |
| 9,518,980 B2 | 12/2016 | Looger et al. | |
| 9,664,697 B2 | 5/2017 | Ai et al. | |
| 9,945,844 B2 | 4/2018 | Looger et al. | |
| 10,509,026 B2 | 12/2019 | Looger et al. | |
| 2010/0154068 A1 | 6/2010 | Yu et al. | |
| 2011/0154515 A1 | 6/2011 | Griesbeck et al. | |
| 2012/0034691 A1 | 2/2012 | Looger et al. | |
| 2014/0101758 A1 | 4/2014 | Ludin et al. | |
| 2014/0101785 A1* | 4/2014 | Looger | C07K 14/00 435/254.11 |
| 2015/0226755 A1 | 8/2015 | Ai et al. | |
| 2015/0315258 A1 | 11/2015 | Looger et al. | |
| 2017/0247769 A1 | 8/2017 | Ast et al. | |
| 2017/0292943 A1 | 10/2017 | Looger et al. | |
| 2018/0250402 A1 | 9/2018 | Deisseroth et al. | |
| 2019/0153067 A1 | 5/2019 | Kim et al. | |
| 2019/0153967 A1 | 5/2019 | Iwase | |

FOREIGN PATENT DOCUMENTS

| | | | | |
|---|---|---|---|---|
| WO | WO 2006/110728 | 10/2006 | | |
| WO | WO 2009/012435 | 1/2009 | | |
| WO | WO-2009012435 A1 * | 1/2009 | ........... | G01N 24/088 |
| WO | WO 2011/056975 | 5/2011 | | |
| WO | WO 2014/059154 | 4/2014 | | |
| WO | WO 2017/048808 | 3/2017 | | |
| WO | WO 2019/104166 | 5/2019 | | |

OTHER PUBLICATIONS

NCBI AXK50352.1, NCBI Database (Year: 2018).*
Broussard (Broussard GJ et al. Nat Neurosci. Sep. 2018;21(9):1272-1280) (Year: 2018).*
Addgene #162371, Gene Name: jGCaMP8s, Nov. 23, 2020, retrieved on Mar. 21, 2022, retrieved from URL <https://www.addgene.org/162371/>, 3 pages.
Addgene #162382, Gene Name: jGCaMP8f, Nov. 23, 2020, retrieved on Mar. 21, 2022, retrieved from URL <https://www.addgene.org/162382/>, 5 pages.
Airan et al., "Temporally precise in vivo control of intracellular signaling," Nature, Apr. 2009, 458:1025-1029.
Akerboom et al., "Crystal Structures of the GCaMP Calcium Sensor Reveal the Mechanism of Fluorescence Signal Change and Aid Rational Design," J.Biol. Chem, Mar. 6, 2009, 284(10):6455-6464.
Akerboom et al., "Optimization of a GCaMP Calcium Indicator for Neural Activity Imaging," J. Neurosci., Oct. 2012, 32(40):13819-13840.
Altschul et al., "Gapped BLAST and PSI-BLAST: a new generation of protein database search programs," Nucleic Acids Res., 1997, 25(17):3389-3402.
Aso et al., "Mushroom body output neurons encode valence and guide memory-based action selection in *Drosophila*," eLife, Dec. 2014:1-42.
Barykina et al., "FGCaMP7, an Improved Version of Fungi-Based Ratiometric Calcium Indication for In Vivo Visualization of Neuronal Activity," Int. J. Mol. Sci., Apr. 2020, 21(8):1-33.
Barykina et al., "Green fluorescent genetically encoded calcium indicator based on calmodulin.M13-peptide from fungi," PLoS One, Aug. 2017, 12(8):1-27.

(Continued)

*Primary Examiner* — Nancy J Leith
*Assistant Examiner* — Douglas Charles Ryan
(74) *Attorney, Agent, or Firm* — Fish & Richardson P.C.

(57) ABSTRACT

Genetically encoded calcium indicator (GECI) polypeptides and the nucleic acid molecules encoding such polypeptides are provided.

25 Claims, 33 Drawing Sheets
(27 of 33 Drawing Sheet(s) Filed in Color)
Specification includes a Sequence Listing.

(56) References Cited

OTHER PUBLICATIONS

Behnia et al., "Processing properties of On and Off pathways for *Drosophila* motion detection," Nature, 2014:427-430.

Berg et al., "Ilastik: interactive machine learning for (bio) image analysis," Nat. Methods, Dec. 2019, 16:1226-1232.

Brenner et al., "An automated microscope for cytologic research a preliminary evaluation," J. Histochem. Cytochem., 1976, 24(1):100-111.

Brinster et al., "Expression of a microinjected immunoglobulin gene in the spleen of transgenic mice," Nature, Nov. 1983, 306(4):332-336.

Cai et al., "A Cell-Based Functional Assay Using a Green Fluorescent Protein-Based Calcium Indicator dCys-GCaMP," Assay and Drug Development Technologies, 2014, 12(6):342-351.

Chen et al., "Ultrasensitive fluorescent proteins for imaging neuronal activity," Nature, Jul. 2013, 499:295-300.

Constantini et al., "Introduction of a rabbit β-globin gene into the mouse germ line," Nature, Nov. 1981, 294(5):92-94.

Dana et al., "High-performance calcium sensors for imaging activity in neuronal populations and microcompartments," Nat. Methods, Jul. 2019, 16:649-657.

Dana et al., "Sensitive red protein calcium indicators for imaging neural activity," eLife, Mar. 2016:1-24.

EBI Accession No. BEH09936,"M13 peptide-LE linker-cpsfGFP-LP linker (GCaMP6s) fusion protein seq 188," Oct. 19, 2017, 1 page.

Emsley et al., "Coot: model-building tools for molecular graphics," Acta Crystallogr. D. Biol. Crystallogr., 2004, D60(12):2126-2132.

Garcea et al., "Virus-like particles as vaccines and vessels for the delivery of small molecules," Curr. Opin. Biotechnol., Oct. 2004, 15:513-517.

GenBank Accession No. ADJ53338.1, "GCaMP3 [synthetic construct]," NCBI, dated Jul. 4, 2010, 2 pages.

GenBank Accession No. HM143847.1, "Synthetic construct GCaMP3 gene, complete cds, " NCBI, dated Jul. 4, 2010, 2 pages.

Goldey et al., "Removeable cranial windows for long-term imaging in awake mice," Nat. Protoc., 2014, 9(11):2515-2538.

Guo et al., "Protein tolerance to random amino acid change," PNAS, Jun. 2004, 101(25):9205-9210.

Hsu et al., "Molecular dissection of G protein preference using Gsα chimeras reveals novel ligand signaling of GPCRs," Am. J. Physiol. Endocrinol. Metab., Jul. 2007, 293(4):E1021-E1029.

Huber et al., "Multiple dynamic representations in the motor cortex during sensorimotor learning," Nature, Apr. 2012, 484:473-478.

Inoue et al., "Rational Engineering of XCaMPs, a Multicolor GECI Suite for In Vivo Imaging of Complex Brain Circuit Dynamics," Cell, May 2019, 177(5):1346-1360.

International Search Report and Written Opinion in International Appln. No. PCT/US2021/051844, dated Mar. 7, 2022, 16 pages.

Jiang et al., "DRAMS: A tool to detect and re-align mixed-up samples for integrative studies of multi-omics data," PloS Comput. Biol., Apr. 2020, 16(4):1-19.

Jones et al., "Voronoi-Based Segmentation of Cells on Image Manifolds," Computer Vision for Biomedical Image Applications, Springer-Verlag, 2005, 3765:535-543.

Kabsch, "XDS," Acta Crystallogr. D. Biol. Crystallogr., 2010, D66:125-132.

Kerr et al., "Imaging input and output of neocortical networks in vivo," PNAS, Sep. 2005, 102(39):14063-14068.

Kitamura et al., "Targeted patch-clamp recordings and single-cell electroporation of unlabeled neurons in vive," Nat. Methods, Jan. 2008, 5(1):61-67.

Kralj et al., "Optical recording of action potentials in mammalian neurons using a microbial rhodopsin," Nat. Methods, Jan. 2012, 9(1):90-95.

Lacy et al., "A foreign β-globin gene in transgenic mice: Integration at abnormal chromosomal positions and expression in inappropriate tissues," Cell, Sep. 1983, 34:343-358.

Maravall et al., "Estimating Intracellular Calcium Concentrations and Buffering withouth Wavelength Ratioing,"Biophys. J., May 2000, 78(5):2655-2667.

McKnight et al., "Expression of the chicken transferrin gene in transgenic mice," Cell, Sep. 1983, 34:335-341.

Muto et al., "Real-Time Visualization of Neuronal Activity during Perception," Curr. Biol., Feb. 2013, 23(4):307-311.

Ohkura et al., "An Improved Genetically Encoded Red Fluorescent Ca2+ Indicator for Detecting Optically Evoked Action Potentials," PLoS One, Jul. 2012, 7(7):1-7.

Palmiter et al., "Differential Regulation of Metallothionein-Thymidine Kinase Fusion Genes in Transgenic Mice and Their Offspring," Cell, Jun. 1982, 29(2):701-710.

Palmiter et al., "Dramatic growth of mice that develop from eggs microinjected with metallothionein-growth hormone fusion genes," Nature, Dec. 1982, 300:611-615.

Palmiter et al., "Metallothionein-Human GH Fusion Genes Stimulate Growth of Mice," Science, Nov. 1983, 222:809-814.

Pepperl-Klindworth et al., "Protein delivery by subviral particles of human cytomegalovirus," Gene Ther., Jan. 2003, 10(3):278-284.

Perkins, "Cell-attached voltage-clamp and current-clamp recording and stimulation techniques in brain slices," J. Neurosci. Methods., 2006, 154:1-18.

Pologruto et al., "Monitoring Neural Activity and [Ca/\2+] with Genetically Encoded Ca/\2+ Indicators," J. Neurosci., Oct. 2004, 24(43):9572-9579.

Stewart et al., "Human Beta-Globin Gene Sequences Injected into Mouse Eggs, Retained in Adults, and Transmitted to Progeny," Science, Sep. 1982, 217:1046-1048.

Stringer et al., "Inhibitory control of correlated intrinsic variability in cortical networks," eLife, Dec. 2016: 1-33.

Strother et al., "Direct Observation of On and Off Pathways in the Dosophila Visual System," Curr. Biol., May 2014, 24(9):976-983.

Strother et al., "The Emergence of Directional Selectivity in the Visual Motion Pathway of Drosophila," Neuron, Apr. 2017, 94(1):168-182.

Tian et al., "Imaging neural activity in worms, flies and mice with improved GCaMP calcium indicators," Nat. Methods, Dec. 2009, 6(12):875-881.

Vagin et al., "Molecular replacement with MOLREP," Acta Crystallorg. D. Biol. Crystallorg., 2010, D66:22-25.

VanScyoc et al., "Calcium Binding to Calmodulin Mutants Monitored by Domain-Specific Intrinsic Phenylalanine and Tyrosine Fluorescence," Biophys. J., Nov. 2002, 83(5):2767-2780.

Wagner et al., "The human β-globin gene and a functional viral thymidine kinase gene in developing mice," PNSA USA, Aug. 1982, 78(8):5016-5020.

Wardill et al., "A Neuron-Based Screening Platform for Optimizing Genetically-Encoded Calcium Indicators," PLoS One, Oct. 2013, 8(10):1-12.

Winn et al., "Macromolecular TLS Refinement in REFMAC at Moderate Resolutions," Meth. Enzymol., 2003, 374(14):300-321.

Zhang et al., "Evaluation of FLIPR Calcium 3 Assay Kit—A New No-Wash Fluorescence Calcium Indicator Reagent," J. Biomol. Screen, 2003, 8(5):571-577.

Zhang et al., "Fast and sensitive GCaMP calcium indicators for imaging neural populations," bioRxiv, Nov. 2021, 62 pages.

International Preliminary Report on Patentability in International Appln. No. PCT/US2021/051844, dated Apr. 6, 2023, 8 pages.

* cited by examiner

3A

3B

3C 4A  4B  4C

5A

5B

5C

6A

6B

6C

|     | Peptide | | |
|---|---|---|---|
| 1 | ------SSRRK---WNKTGHAVRAIGRLSSLE-NVYIKADKQKNGIKANFKIRHNIEDGGVQLAYHYQQNTPIGDGPVLLP | 108 |

```
  1   ------SSRRK---WNKTGHAVRAIGRLSSLE-NVYIKADKQKNGIKANFKIRHNIEDGGVQLAYHYQQNTPIGDGPVLLP   108
  1   MSHHHHHSTRKKTFKEVATAVKIIARLMGLKINVYIKADKQKNGIKANFKIRHNIEDGGVQLAYHYQQNTPIGDGPVLLP    80
  1   MSHHHHHSTRKKTFKEVATAVKIIARLMGLKINVYIKADKQKNGIKANFKIRHNIEDGGVQLAYHYQQNTPIGDGPVLLP    80
  1   MSHHHHHSTRKKTFKEVATAVKIIARLMGLKINVYIKADKQKNGIKANFKIRHNIEDGGVQLAYHYQQNTPIGDGPVLLP    80
  1   MSHHHHHSTRKKTFKEVANAVKISASLMGLE-NVYIKADKQKNGIKANFKIRHNIEDGGVQLAYHYQQNTPIGDGPVLLP    80
  1   MSHHHHHSTRKKTFKEVANAVKISASLMGLKINVYIKADKQKNGIKANFKIRHNIEDGGVQLAYHYQQNTPIGDGPVLLP    80
  1   MSHHHHHSTRKKTFKEVATAVKIIARLMGLKINVYIKADKQKNGIKANFKIRHNIEDGGVQLAYHYQQNTPIGDGPVLLP    80
  1   MSHHHHHSTRKKTFKEVATAVIIGRLMGLKINVYIKADKQKNGIKANFKIRHNIEDGGVQLAYHYQQNTPIGDGPVLLP     80
  1   MSHHHHHSTRKKTFKEVATAVIIAMLMGLKINVYIKADKQKNGIKANFKIRHNIEDGGVQLAYHYQQNTPIGDGPVLLP     80
  1   MSHHHHHSTRKKTFKEVATAVKIIARLMGLKINVYIKADKQKNGIKANFKIRHNIEDGGVQLAYHYQQNTPIGDGPVLLP    80
  1   MSHHHHHSTRKKTFKEVANAVKISARLSGLKINVYIKADKQKNGIKANFKIRHNIEDGGVQLAYHYQQNTPIGDGPVLLP    80

109   DNHYLSVQSKLSKDPNEKRDHMVLLEFVTAAGITLGMDELYKGGTGGSMVSKGEELFTGVVPILVELDGDVNGHKFSVSG   188
 81   DNHYLSVESKLSKDPNEKRDHMVLLEFVTAAGITLGMDELYKGGTGGSMVSKGEELFTGVVPILVELDGDVNGHKFSVSG   160
 81   DNHYLSVESKLSKDPNEKRDHMVLLEFVTAAGITLGMDELYKGGTGGSMVSKGEELFTGVVPILVELDGDVNGHKFSVSG   160
 81   DNHYLSVESKLSKDPNEKRDHMVLLEFVTAAGITLGMDELYKGGTGGSMVSKGEELFTGVVPILVELDGDVNGHKFSVSG   160
 81   DNHYLSVQSKLSKDPNEKRDHMVLLEFVTAAGITLGMDELYKGGTGGSMVSKGEELFTGVVPILVELDGDVNGHKFSVSG   160
 81   DNHYLSVQSKLSKDPNEKRDHMVLLEFVTAAGITLGMDELYKGGTGGSMVSKGEELFTGVVPILVELDGDVNGHKFSVSG   160
 81   DNHYLSVESKLSKDPNEKRDHMVLLEFVTAAGITLGMDELYKGGTGGSMVSKGEELFTGVVPILVELDGDVNGHKFSVSG   160
 81   DNHYLSVESKLSKDPNEKRDHMVLLEFVTAAGITLGMDELYKGGTGGSMVSKGEELFTGVVPILVELDGDVNGHKFSVSG   160
 81   DNHYLSVESKLSKDPNEKRDHMVLLEFVTAAGITLGMDELYKGGTGGSMVSKGEELFTGVVPILVELDGDVNGHKFSVSG   160
 81   DNHYLSVESKLSKDPNEKRDHMVLLEFVTAAGITLGMDELYKGGTGGSMVSKGEELFTGVVPILVELDGDVNGAKFSVSG   160
 81   DNHYLSVESKLSKDPNEKRDHMVLLEFVTAAGITLGMDELYKGGTGGSMVSKGEELFTGVVPILVELDGLVRGKFSVSG    160

189   EGEGDATYGKLTLKFICTTGKLPVPWPTLVTTLTYGVQCFSRYPDHMKQHDFFKSAMPEGYIQERTIFFKDDGNYKTRAE   268
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
161   EGEGDATYGKLTLKFICTTGKLPVPWPTLVTTLTYGVQCFSRYPDHMKQHDFFKSAMPEGYIQERTIFFKDDGNYKTRAE   240
```

FIG. 10A

```
269                                                                              348
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320
241  VKFEGDTLVNRIELKGIDFKEDGNILGHKLEYNLPDQLTEEQIAEFKEAFSLFDKDGDGTITTKELGTVMRSLGQNPTEA  320

349  ELQDMINEVDADGDGTIDFPEFLTMMARKMKYTDSEEEIREAFRVFDKDGNGYISAAELRHVMTNLGEKLTDEEVDEMIR  428
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400
321  ELQDMINEVDADGDGTIDFPEFLTMMARKMKYTDSEEEIREAFRVFDKDGNGYISAAELRHVMTNLGEKLTDEEVDEMIR  400

429  EADIDGDGQVNYEEFVQMMTAK  450
401  EADIDGDGQVNYEEFVQMMTAK  422
401  EADIDGDGQVNYEEFVQMMTAK  422
401  EADIDGDGQVNYEEFVQMMTAK  422
401  EADIDGDGQVNYEEFVQMSTAK  422
401  EADIDGDGQVNYEEFVQMMTAK  422
401  EADIDGDGQVNYEEFVQMMTAK  422
401  EADIDGDGQVNYEEFVQMMTAK  422
401  EADIDGDGQVNYEEFVQMMTAK  422
401  EADIDGDGQVNYEEFVQMMTAK  422
401  EADIDGDGQVNYEEFVQMMTAK  422
```

FIG. 10B

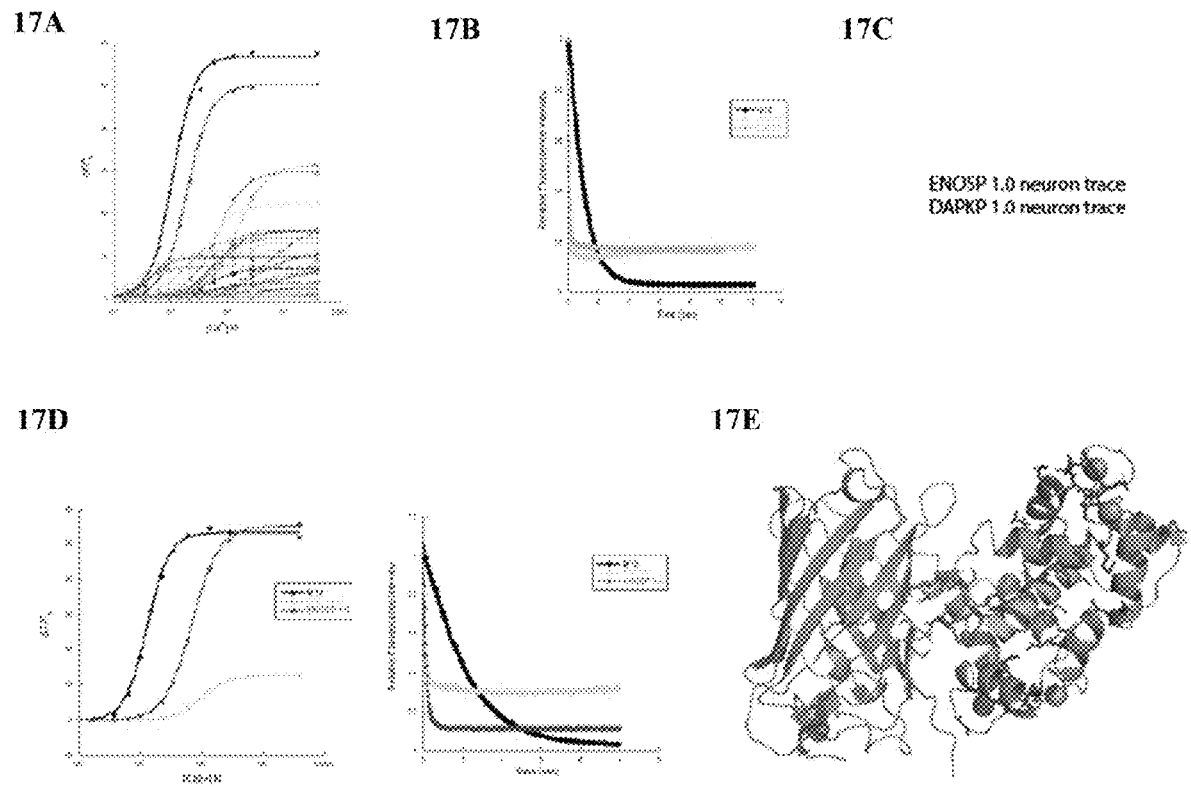
FIG. 17A-E

19A

19B

19C

27A

27B

GENETICALLY ENCODED CALCIUM INDICATORS (GECIS) AND METHODS OF MAKING AND USING

CROSS REFERENCE TO RELATED APPLICATIONS

This application claims the benefit of priority under 35 U.S.C. 119(e) to U.S. Application No. 63/082,222 filed on Sep. 23, 2020, the entirely of which is incorporated by reference herein.

INCORPORATION BY REFERENCE

This application contains a Sequence Listing that has been submitted electronically as an ASCII text file named "51601020.txt." The ASCII text file, created on Mar. 21, 2022, is 76,491 bytes in size. The material in the ASCII text file is hereby incorporated by reference in its entirety.

BACKGROUND

Calcium is a universal second messenger regulating essential cellular signaling events in a broad range of cells, tissues and organisms. In neurons, action potentials (APs) trigger large and rapid changes in cytoplasmic free calcium. Similarly, activation of synaptic glutamate receptors during synaptic transmission produces $Ca^{2+}$ in dendritic spines. Calcium imaging using synthetic calcium indicators has been used to measure neuronal spiking and synaptic input across populations of neurons in vitro and in vivo. However, synthetic indicators are difficult to target to specific cell types or sub-cellular locations, and the loading procedures are invasive and damaging to neural tissue, precluding repeated, chronic in vivo measurements.

SUMMARY

Described herein are genetically encoded calcium indicator (GECI) polypeptides and the nucleic acid molecules encoding such polypeptides.

In one aspect, nucleic acid molecules encoding a genetically encoded calcium indicator (GECI) polypeptide are provided. In some embodiments, the GECI polypeptide includes an amino acid sequence having at least 95% sequence identity (e.g., at least 99% sequence identity; e.g., 100% sequence identity) to a sequence shown in SEQ ID NO:1, SEQ ID NO:3, or SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21. In some embodiments, the GECI includes an amino acid sequence shown in SEQ ID NO:1, SEQ ID NO:3, or SEQ ID NO:5, SEQ ID NO:7, SEQ ID NO:9, SEQ ID NO: 11, SEQ ID NO:13, SEQ ID NO:15, SEQ ID NO:17, SEQ ID NO:19, or SEQ ID NO:21.

In one aspect, a nucleic acid molecule as described herein has the sequence shown in SEQ ID NO:2, SEQ ID NO:4, or SEQ ID NO:6, SEQ ID NO:8, SEQ ID NO:10, SEQ ID NO:12, SEQ ID NO:14, SEQ ID NO: 16, SEQ ID NO:18, SEQ ID NO:20, or SEQ ID NO:22. In another aspect, vectors are provided that include a nucleic acid molecule as described herein. In still another aspect, cells are provided that include a nucleic acid molecule as described herein or a vector as described herein.

In one aspect, GECI polypeptides are provided. In some embodiments, the polypeptide includes an amino acid sequence having at least 95% sequence identity (e.g., at least 99% sequence identity; e.g., 100% sequence identity) to a sequence shown in SEQ ID NO:1, SEQ ID NO:3, or SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21. In some embodiments, the polypeptide includes an amino acid sequence shown in SEQ ID NO:1, SEQ ID NO:3, or SEQ ID NO:5, SEQ ID NO:7, SEQ ID NO:9, SEQ ID NO: 11, SEQ ID NO:13, SEQ ID NO:15, SEQ ID NO:17, SEQ ID NO:19, or SEQ ID NO:21. In one aspect, cells are provided that include a polypeptide as described herein.

In one aspect, methods of screening agents for agonists or antagonists of G-protein coupled receptor (GPCR) polypeptides are provided. Such methods typically include (i) contacting a test agent with a cell including a GPCR polypeptide and a genetically encoded calcium indicator (GECI) polypeptide, where the GECI polypeptide includes an amino acid sequence having at least 95% sequence identity to SEQ ID NO:1, SEQ ID NO:3, or SEQ ID NO:5, SEQ ID NO:7, SEQ ID NO:9, SEQ ID NO:11, SEQ ID NO: 13, SEQ ID NO: 15, SEQ ID NO:17, SEQ ID NO:19, or SEQ ID NO:21; and (ii) determining a level of fluorescence produced by the cell, where an increase in fluorescence relative to a control indicates that the test agent is an agonist of the GPCR polypeptide and a decrease in fluorescence relative to a control indicates that the test agent is an antagonist of the GPCR polypeptide.

In some embodiments, the cell is in vitro. In some embodiments, the cell is in vivo. In some embodiments, the cell is in vivo in a mouse, a worm, a rat, a fish, or a fly. In some embodiments, the agent is selected from nucleic acids, polypeptides, small molecules, chemical compounds, and combinations thereof. In some embodiments the nucleic acid is an inhibitory nucleic acid. Representative inhibitory nucleic acids include, without limitation, a triplex forming oligonucleotide, an aptamer, a ribozyme, an antisense RNA, a short interfering RNA (siRNA), or a micro-RNA (miRNA). In some embodiments, the polypeptide is an antibody.

In one aspect, methods of monitoring the activity of a cell is provided. Such methods typically include (i) providing a cell comprising a GPCR and a GECI, wherein the GECI comprises an amino acid sequence having at least 95% sequence identity to a sequence shown in SEQ ID NO:1, SEQ ID NO:3, or SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21; (ii) stimulating the cell; and (iii) detecting the fluorescence emitted by the cell.

In some embodiments, the cell is provided in a biological sample from a subject. Representative subjects include, without limitation, a mouse, a worm, a rat, a fish, or a fly. In some embodiments, the detecting step includes imaging. In some embodiments, the cell is a neuronal cell, a muscle cell or a cardiomyocyte.

In one aspect, nucleic acid molecules encoding a calmodulin-binding peptide portion of a genetically encoded calcium indicator (GECI) polypeptide are provided. In some embodiments, the peptide portion of the GECI polypeptide includes an amino acid sequence having at least 95% sequence identity (e.g., at least 99% sequence identity; e.g., 100% sequence identity) to the dashed underlined portion (residues 10-29) of the sequence shown in SEQ ID NO:1, SEQ ID NO:3, or SEQ ID NO:5, SEQ ID NO:7, SEQ ID NO:9, SEQ ID NO:11, SEQ ID NO:13, SEQ ID NO:15, SEQ ID NO: 17, SEQ ID NO: 19, or SEQ ID NO:21, or any of SEQ ID NOs: 25-55. In some embodiments, the calmodulin-binding peptide portion of the GECI includes the dashed underlined portion (residues 10-29) of the sequence shown in SEQ ID NO:1, SEQ ID NO:3, or SEQ ID NO:5, SEQ ID NO:7, SEQ ID NO:9, SEQ ID NO:11, SEQ ID NO: 13, SEQ ID NO:15, SEQ ID NO:17, SEQ ID NO:19, SEQ ID NO:21, or any of SEQ ID NOs: 25-55.

In one aspect, vectors including a nucleic acid molecule as described herein are provided. In one aspect, cells are provided that include a vector as described herein or a nucleic acid molecule as described herein.

In one aspect, calmodulin-binding peptide portions of a GECI polypeptide are provided. Such peptide portions typically include an amino acid sequence having at least 95% sequence identity (e.g., at least 99% sequence identity; e.g., 100% sequence identity) to the dashed underlined portion (residues 10-29) of the sequence shown in SEQ ID NO:1, SEQ ID NO:3, or SEQ ID NO:5, SEQ ID NO:7, SEQ ID NO:9, SEQ ID NO: 11, SEQ ID NO:13, SEQ ID NO:15, SEQ ID NO:17, SEQ ID NO:19, or SEQ ID NO:21, or any of SEQ ID NOs: 25-55. In some embodiments, the peptide portion comprises the dashed underlined (residues 10-29) amino acid sequence shown in SEQ ID NO:1, SEQ ID NO:3, or SEQ ID NO:5, SEQ ID NO:7, SEQ ID NO:9, SEQ ID NO:11, SEQ ID NO: 13, SEQ ID NO:15, SEQ ID NO:17, SEQ ID NO:19, or SEQ ID NO:21, or any of SEQ ID NOs: 25-55.

In one aspect, methods of imaging neurons in mouse primary visual cortex (V1) is provided. Such methods typically include introducing a nucleic acid encoding a jGCaMP8 sensor into a neuronal cell under conditions in which the nucleic acid is expressed, where the nucleic acid has a sequence shown in SEQ ID NO:2, SEQ ID NO:4, or SEQ ID NO:6, SEQ ID NO:8, SEQ ID NO:10, SEQ ID NO:12, SEQ ID NO:14, SEQ ID NO: 16, SEQ ID NO:18, SEQ ID NO:20, or SEQ ID NO:22, or encodes a polypeptide having the amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21; and recording neuronal response to drifting grating stimuli.

In some embodiments, the cells are in culture. In some embodiments, the cells are in vivo. In some embodiments, such methods further include performing (e.g., simultaneously) cell-attached recordings.

In one aspect, methods of discriminating single action potentials in vivo are provided. Such methods typically include introducing a nucleic acid encoding a jGCaMP8 sensor into a neuronal cell under conditions in which the nucleic acid is expressed, where the nucleic acid has a sequence shown in SEQ ID NO:2, SEQ ID NO:4, or SEQ ID NO:6, SEQ ID NO:8, SEQ ID NO: 10, SEQ ID NO:12, SEQ ID NO:14, SEQ ID NO: 16, SEQ ID NO:18, SEQ ID NO:20, or SEQ ID NO:22, or encodes a polypeptide having the amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21; thereby dramatically improving spike deconvolution (e.g., from fast-spiking interneurons in vivo).

In one aspect, methods of imaging neurons are provided. Such methods typically include introducing a nucleic acid encoding a jGCaMP8 sensor into a neuronal cell under conditions in which the nucleic acid is expressed, wherein the nucleic acid has a sequence shown in SEQ ID NO:2, SEQ ID NO:4, or SEQ ID NO:6, SEQ ID NO:8, SEQ ID NO: 10, SEQ ID NO:12, SEQ ID NO:14, SEQ ID NO: 16, SEQ ID NO:18, SEQ ID NO:20, or SEQ ID NO:22, or encodes a polypeptide having the amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21; and imaging the neurons.

In some embodiments, such methods further include stimulating the jGCaMP8 sensor. In some embodiments, the neurons are in Drosophila larval neuromuscular junction. In some embodiments, the neurons are L2 neurons of adult Drosophila. In some embodiments, the method is performed to record the response of neurons to high-frequency light pulses. In some embodiments, the method is performed to identify the response of neurons to odors. In some embodiments, the neurons are in zebrafish. In some embodiments, the neurons are in C. elegans. In some embodiments, the neurons are iPSC-derived neurons (and/or iPSC-derived cardiomyocytes).

In one aspect, methods of monitoring neuronal activity in cells are provided. Such methods typically include introducing a nucleic acid encoding a jGCaMP8 sensor into a neuronal cell under conditions in which the nucleic acid is expressed, where the nucleic acid has a sequence shown in SEQ ID NO:2, SEQ ID NO:4, or SEQ ID NO:6, SEQ ID NO:8, SEQ ID NO:10, SEQ ID NO:12, SEQ ID NO: 14, SEQ ID NO:16, SEQ ID NO:18, SEQ ID NO:20, or SEQ ID NO:22, or encodes a polypeptide having the amino acid sequence shown in SEQ ID NO:1, SEQ ID NO:3, SEQ ID NO:5, SEQ ID NO:7, SEQ ID NO:9, SEQ ID NO:11, SEQ ID NO: 13, SEQ ID NO:15, SEQ ID NO: 17, SEQ ID NO: 19, or SEQ ID NO:21; and monitoring neuronal activity.

In some embodiments, the method further including exposing the neuronal cells to a stimulus. In some embodiments, the method further including exposing the neuronal cells to a test compound. In some embodiments, the cells are brain organoids in culture. In some embodiments, the cells are in vivo.

In some embodiments, the test compounds are selected from the group consisting of peptides, nucleic acids, small molecules, chemical compounds.

In some embodiments, the monitoring detects seizure-like neuronal activity (e.g., high-frequency firing). In some embodiments, the monitoring identifies test compounds that modify interneuron activity.

In one aspect, methods of monitoring cells are provided. Such methods typically include introducing a nucleic acid encoding a jGCaMP8 sensor into a cell under conditions in which the nucleic acid is expressed, where the nucleic acid has a sequence shown in SEQ ID NO:2, SEQ ID NO:4, or SEQ ID NO:6, SEQ ID NO:8, SEQ ID NO: 10, SEQ ID NO: 12, SEQ ID NO:14, SEQ ID NO:16, SEQ ID NO:18, SEQ ID NO:20, or SEQ ID NO:22, or encodes a polypeptide having the amino acid sequence shown in SEQ ID NO:1, SEQ ID NO:3, SEQ ID NO:5, SEQ ID NO:7, SEQ ID NO:9, SEQ ID NO: 11, SEQ ID NO: 13, SEQ ID NO:15, SEQ ID NO:17, SEQ ID NO:19, or SEQ ID NO:21; and monitoring cells.

In some embodiments, the cells are immune cells. In some embodiments, the immune cells are T cells.

In some embodiments, the method further includes exposing the cells to a virus under conditions in which the virus infects the cells. In some embodiments, the method further includes exposing the cells to a test compound.

In some embodiments, the monitoring is to screen for viral entry blockers.

In some embodiments, the methods described herein further include exposing the cells to calcium. In some embodiments, the methods further include changing the calcium concentration in the culture medium.

In one aspect, a nucleic acid molecule encoding a genetically encoded calcium indicator (GECI) polypeptide is provided, wherein the GECI polypeptide comprises an amino acid sequence having at least 95% sequence identity to a sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, or SEQ ID NO:21. In some embodiments, the GECI comprises an amino acid sequence having at least 99% sequence identity to a sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21. In some embodiments, the GECI comprises an amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, or SEQ ID NO:21. In some embodiments, the nucleic acid has the sequence shown in SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO:18, SEQ ID NO:20, or SEQ ID NO:22. Also provided is a vector including any of the above-described nucleic acid molecules. Also provided is a cell including such a vector, or a cell including any of the above-described nucleic acid molecule.

In another aspect, a GECI polypeptide is provided, wherein the polypeptide comprises an amino acid sequence having at least 95% sequence identity to a sequence shown in SEQ ID NO:1, SEQ ID NO:3, SEQ ID NO:5, SEQ ID NO:7, SEQ ID NO:9, SEQ ID NO: 11, SEQ ID NO:13, SEQ ID NO:15, SEQ ID NO:17, SEQ ID NO:19, or SEQ ID NO:21. In some embodiments, the polypeptide comprises an amino acid sequence having at least 99% sequence identity to a sequence shown in SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO:17, SEQ ID NO:19, or SEQ ID NO:21. In some embodiments, the polypeptide comprises an amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21. Also provided is a cell including any of the above-described polypeptides. In some embodiments, such a cell further includes a nucleic acid molecule encoding a G-protein coupled receptor (GPCR) polypeptide. In some embodiments, such a cell further includes a nucleic acid molecule encoding an ion channel. In some embodiments, the nucleic acid molecule encoding the GPCR polypeptide or the ion channel is heterologous to the cell.

In still another aspect, a method of screening agents for agonists or antagonists of G-protein coupled receptor (GPCR) polypeptides is provided. Generally, such a method includes (i) contacting a test agent with a cell including a GPCR polypeptide and a genetically encoded calcium indicator (GECI) polypeptide, wherein the GECI polypeptide comprises an amino acid sequence having at least 95% sequence identity to SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO: 17, SEQ ID NO:19, or SEQ ID NO:21; and (ii) determining a level of fluorescence produced by the cell. Typically, an increase in fluorescence relative to a control indicates that the test agent is an agonist of the GPCR polypeptide, and a decrease in fluorescence relative to a control indicates that the test agent is an antagonist of the GPCR polypeptide. In some embodiments, the cell is in vitro. In some embodiments, the cell is in vivo (e.g., in a mouse, a worm, a rat, or a fly).

In some embodiments, the agent is a nucleic acid, a polypeptide, a small molecule or combinations thereof. In some embodiments, the nucleic acid is an inhibitory nucleic acid. Representative inhibitory nucleic acids include, without limitation, a triplex forming oligonucleotide, an aptamer, a ribozyme, an antisense RNA, a short interfering RNA (siRNA), or a micro-RNA (miRNA). In some embodiments, the polypeptide is an antibody.

In still another aspect, a method of monitoring the activity of a cell is provided. Generally, such a method includes (i) providing a cell including a GPCR and a GECI, wherein the GECI comprises an amino acid sequence having at least 95% sequence identity to a sequence shown in SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO: 17, SEQ ID NO: 19, or SEQ ID NO:21; (ii) stimulating the cell; and (iii) detecting the fluorescence emitted by the cell. In some embodiments, the cell is provided in a biological sample from a subject (e.g., a mouse, a worm or a fly). In some embodiments, the detecting step comprises imaging. In some embodiments, the cell is a neuronal cell, a muscle cell or a cardiomyocyte.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION OF DRAWINGS

The patent or application file contains at least one drawing executed in color. Copies of this patent or patent application publication with color drawings will be provided by the office upon request and payment of the necessary fee.

FIG. 1 is a schematic showing the 3D structure of a GCaMP.

FIG. 2 shows screening results (n=425 variants with 1AP ΔF/F0>ΔF/F0 of GCaMP6s) for jGCaMP8 variants, ranked by ΔF/F0, half-rise time for 1 AP stimulation, half-decay time for 1 AP stimulation, and time to fluorescent peak for 1 AP stimulation. All data was normalized to GCaMP6s control. Other jGCaMP controls (7f, 7s, 7c, 7b) as well as the XCaMP sensor family (XCaMP-G, XCaMP-Gf, and XCaMP-Gf0) were included. Horizontal dashed line (y=1) in each plot signifies GCaMP6s performance. The jGCaMP8 sensors are shown in bold and underlined.

FIGS. 3A-3C show representative results for jGCaMP8f in a field stimulation screen. FIG. 3A shows cultured neurons expressing jGCaMP8f GECI (neuron somata that were automatically segmented are outlined). FIG. 3B are plots showing ΔF/F0 of the GECI in response to 1, 3, 10, and 160 action potentials elicited by electrical stimulation at t=1 s. FIG. 3C shows individual time traces of the 1AP response of each segmented soma (N=34).

FIGS. 4A-4C show representative results for jGCaMP8m in cultured neurons. FIG. 4A shows cultured neurons expressing jGCaMP8m GECI (neuron somata that were automatically segmented are outlined). FIG. 4B are plots showing ΔF/F0 of the GECI in response to 1, 3, 10, and 160 action potentials elicited by electrical stimulation at t=1 s. FIG. 4C shows individual time traces of the 1AP response of each segmented soma. N=81 somata were segmented, only a subset of which is shown in FIG. 4C for clarity.

FIGS. 5A-5C show representative results for jGCaMP8s in cultured neurons. FIG. 5A shows cultured neurons expressing jGCaMP8s GECI (neuron somata that were automatically segmented are outlined). FIG. 5B are plots showing ΔF/F0 of the GECI in response to 1, 3, 10, and 160 action potentials elicited by electrical stimulation at t=1 s. FIG. 5C shows individual time traces of the 1AP response of each segmented somata (N=41).

FIGS. 6A-6C show representative results for jGCaMP7f in cultured neurons. FIG. 6A shows cultured neurons expressing jGCaMP7f GECI (neuron somata that were automatically segmented are outlined). FIG. 6B are plots showing ΔF/F0 of the GECI in response to 1, 3, 10, and 160 action potentials elicited by electrical stimulation at t=1 s. FIG. 6C shows individual time traces of the 1AP response of each segmented soma (N=32).

FIGS. 7A-7F are graphs showing the performance of jGCaMP8 in cultured neurons. FIG. 7A shows the average responses to 1, 3, 10, 160 stimulation pulses. First stimulation pulse occurs at t=1 s. GCaMP6s: 802 wells; jGCaMP7f: 893 wells; jGCaMP8f: 40 wells; jGCaMP8m: 11 wells; jGCaMP8s: 24 wells. Inset: zoomed in response to 1 stimulation pulse. FIG. 7B shows the peak ΔF/F0 amplitude. Inset: zoomed in. Graphs of the sensor half-rise time (FIG. 7C), time-to-peak (FIG. 7D), half-decay time (FIG. 7E) and signal-to-noise ratio (FIG. 7F) normalized to GCaMP6s are shown. Data shown as mean±s.e.m.

FIG. 8 is a graph showing resting fluorescence (F0) in neuronal cultures expressing GECI variants. All variants were imaged in the same week (N=3 96-well plates) to reduce variability in culture conditions. GCaMP6s: 23 wells; jGCaMP8f: 24 wells; jGCaMP8s: 12 wells; jGCaMP8.712: 12 wells; jGCaMP8.543: 12 wells; jGCaMP8.707: 12 wells; jGCaMP8.455: 4 wells; jGCaMP7f: 12 wells; jGCaMP7s: 23 wells; jGCaMP7c: 12 wells; jGCaMP7b: 12 wells; XCaMP-G: 23 wells; XCaMP-Gf: 24 wells; XCaMP-Gf0: 11 wells. Data shown as mean±s.e.m.

FIGS. 10A and 10B shows an alignment, top to bottom, of jGCaMP7f (SEQ ID NO:23); jGCaMP8.455 (SEQ ID NO:17); jGCaMP8f (SEQ ID NO:1); jGCaMP8.543 (SEQ ID NO:13); jGCaMP8.640 (SEQ ID NO:9); jGCaMP6s_ENOSP (SEQ ID NO:19); jGCaMP6s_ENOSP_linker1 (SEQ ID NO:21); jGCaMP8.333 (SEQ ID NO:7); jGCaMP8m (SEQ ID NO:5); jGCaMP8s (SEQ ID NO:3); jGCaMP8.707 (SEQ ID NO:15); and jGCaMP8.712 (SEQ ID NO:11).

Figure 11:
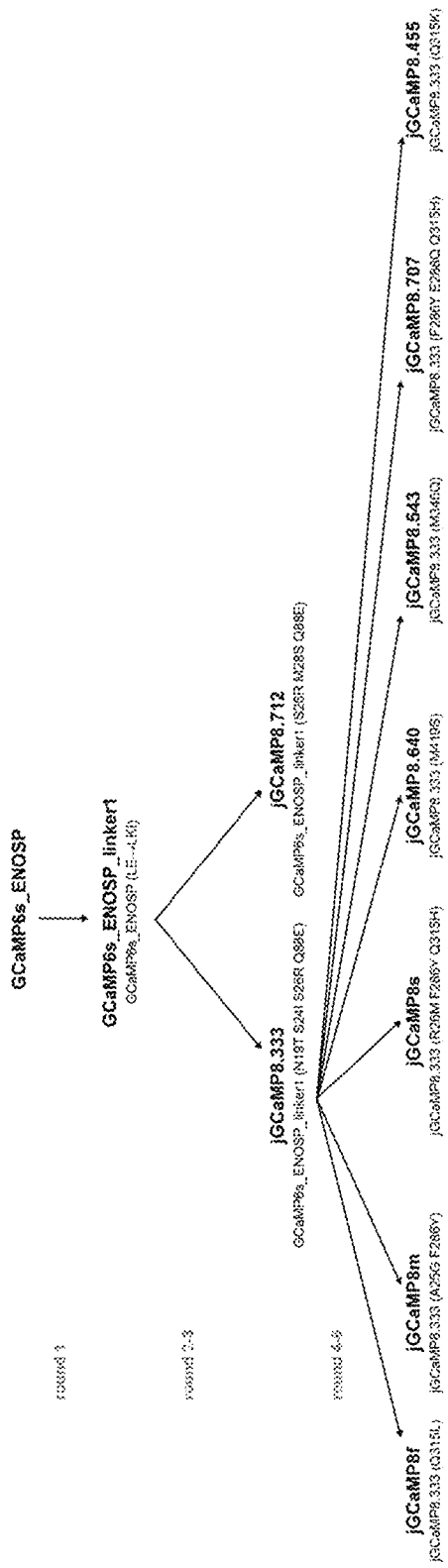

FIG. 11 is an evolutionary history of the jGCaMP8 family. All mutations were based on the GCaMP6s protein with the M13 peptide replaced by an endothelial nitric oxide synthase peptide (ENOSP), denoted jGCaMP6s_ENOSP. In the first round of mutations, linker 1 connecting ENOSP and circularly permuted GFP was optimized to create GCaMP6s_ENOSP_linker1. In the second round of mutations, structural point mutations were made to improve the kinetics and sensitivity of the sensor. In the third round of mutations, jGCaMP8.333, a highly sensitive and fast sensor, was produced from a combination of the beneficial mutations in the second round. In subsequent rounds, jGCaMP8.333 was mutated further.

Figure 12A:
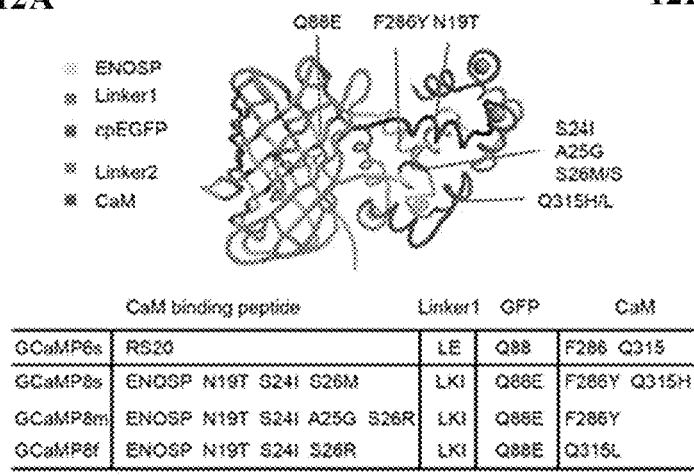
Figure 12B:
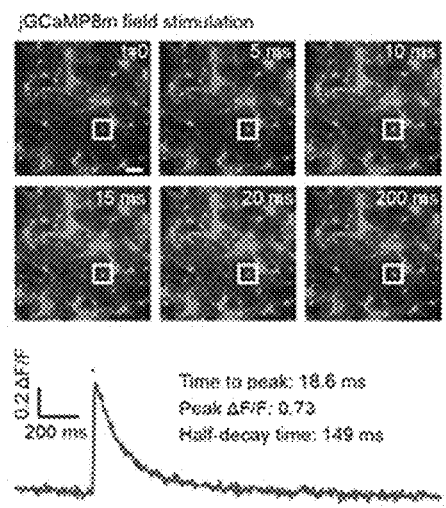
Figure 12C:
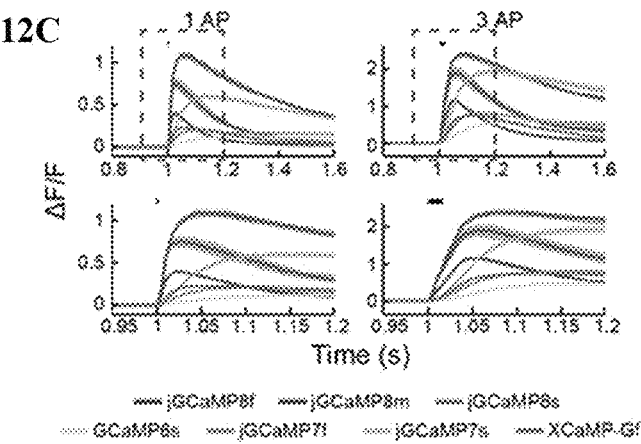
Figure 12D:
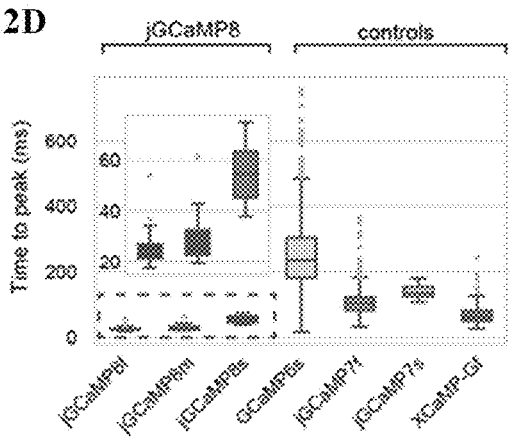
Figure 12E:
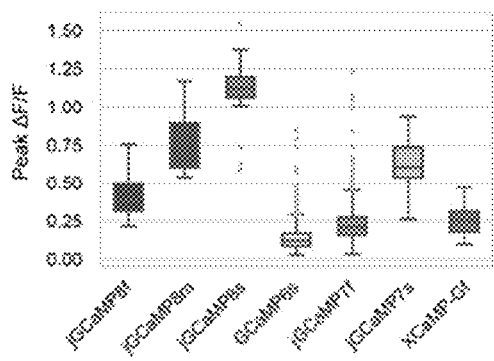
Figure 12F:
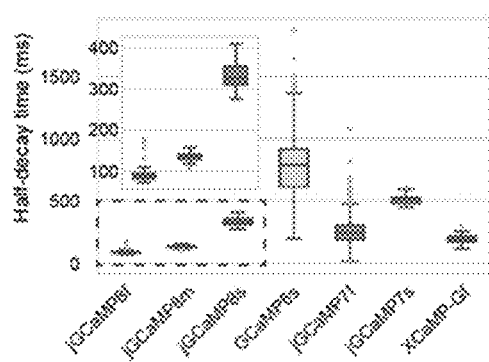
Figure 12G:
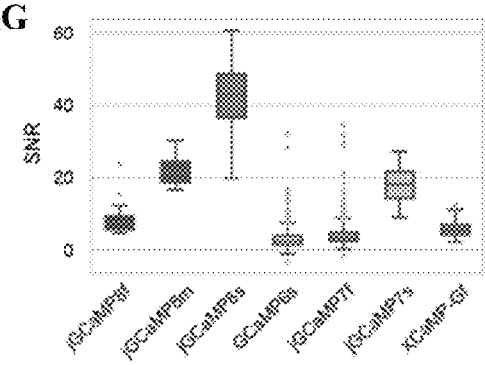
Figure 12H:
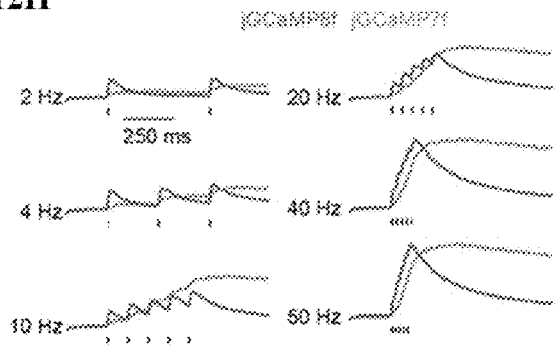

FIG. 12A-12H show GCaMP mutagenesis and screening in cultured neurons. FIG. 12A shows jGCaMP8.410.80 protein crystal structure and mutations in different jGCaMP8 variants relative to GCaMP6s (top). ENOSP (yellow), linker 1 (ENOSP-cpGFP; dark grey), linker 2 (cpGFP-CaM; light grey), cpGFP (green), CaM (blue), mutated sites (red), $Ca^{2+}$ ions (orange). Bottom table, mutations for each jGCaMP8 variant. FIG. 12B are photos showing representative frames of a jGCaMP8m FOV in the field-stimulation assay (top; seale bar 100 µm) and fluorescence trace and response characteristics of the cell body outlined in white in the top panel (bottom). FIG. 12C are graphs showing responses to 1 and 3 field stimuli (top; black bars) and zoomed-in insets from the top panel to highlight rise and decay kinetics (bottom). Solid lines: mean, shaded area: s.e.m. FIG. 12D-FIG. 12G are graphs showing 1-AP response characteristics of jGCaMP8 indicators compared to GCaMP6s, jGCaMP7f,s and XCaMP-Gf in the screen. Each point represents the compilation of a single well (jGCaMP8f: 48 wells, 1,696 neurons; jGCaMP8m: 11 wells, 496 neurons; jGCaMP8s: 24 wells, 1,183 neurons; GCaMP6s: 859 wells, 24,998 neurons; jGCaMP7f: 950 wells, 26,679 neurons; jGCaMP7s: 22 wells, 514 neurons; XCaMP-Gf: 69 wells, 1,305 neurons; overall statistics: 23 independent transfections, 130 96-well plates). FIG. 12D shows time-to-peak; FIG. 12E shows peak $\Delta F/F_0$; FIG. 12F shows half-decay time; and FIG. 12G shows SNR. Insets in FIG. 12D and FIG. 12F show zoomed jGCaMP8 kinetics. FIG. 12H are traces showing jGCaMP8f and jGCaMP7f responses to field stimulation pulses of increasing frequencies imaged in neuronal culture under 2P illumination.

Figures 13A, 13B, 13C, 13D, 13E, 13F, 13G:
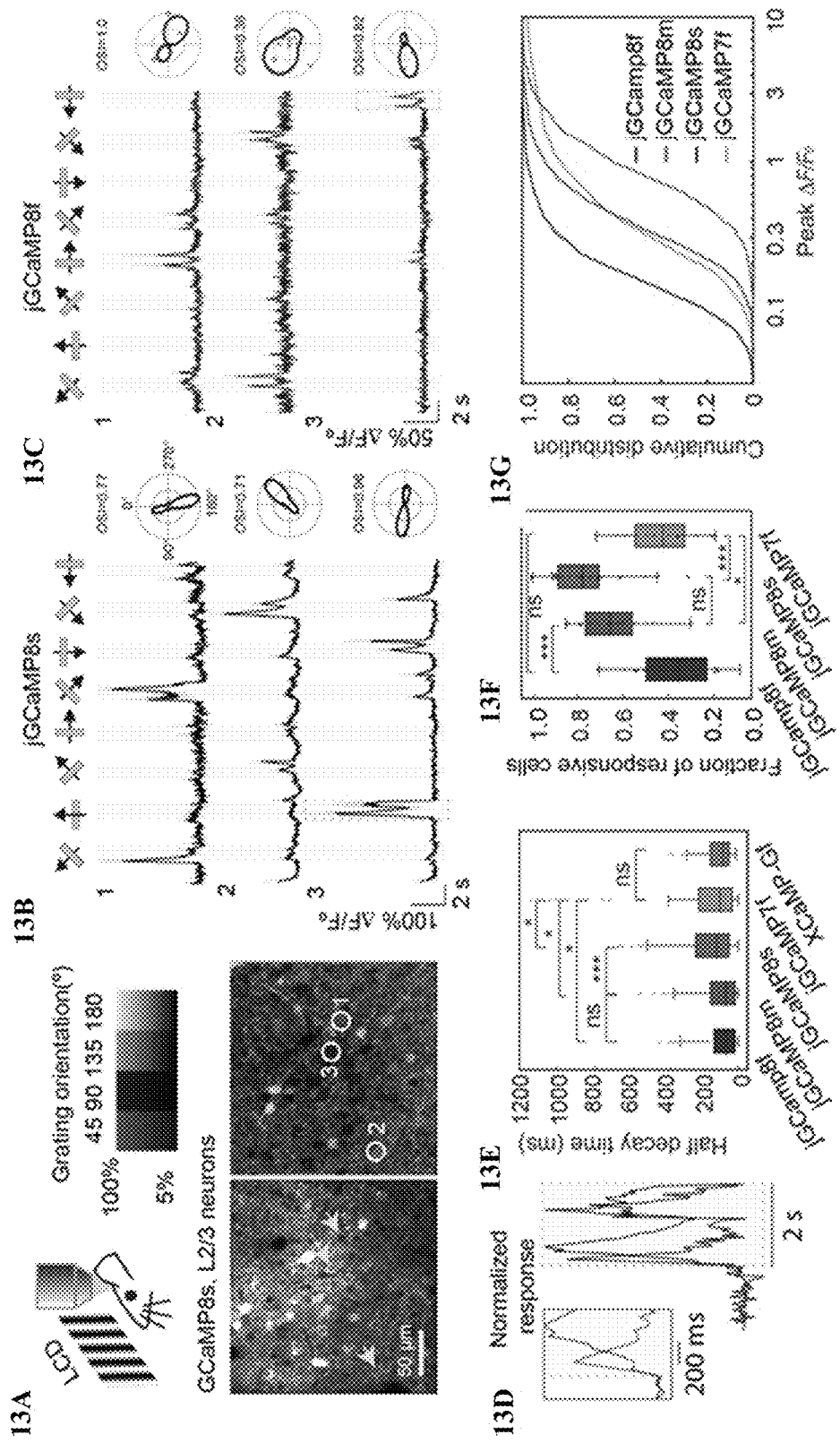

FIG. 13A-13G shows imaging of neural populations in the mouse primary visual cortex (V1) in vivo. FIG. 13A is a schematic of the experiment (top) and an example image of V1 L2/3 cells expressing jGCaMP8s (bottom left), and the same field of view color-coded based on the neurons' preferred orientation (hue) and response amplitude (brightness) (bottom right). FIG. 13B-13C show example traces from three L2/3 neurons expressing jGCaMP8s (FIG. 13B, same cells as indicated in FIG. 13A) or jGCaMP8f (FIG. 13C). Averages of five trials with shaded s.e.m. were displayed. Eight grating motion directions are indicated by arrows and shown above traces. The preferred stimulus is the direction evoking the largest response. Polar plots indicate the preferred direction of cells. The orientation selectivity index (OSI) is displayed above each polar plot. FIG. 13D show a high magnification view of fluorescence changes corresponding to the orange boxes in FIG. 13B (black, jGCaMP8s) and FIG. 13C (blue, jGCaMP8f), normalized to the peak of the response. The inset shows a further zoomed view. FIG. 13E is a graph showing the half-decay time of the fluorescence response after the end of the visual stimulus (jGCaMP7f, 320 cells, n=3 mice; XCaMP-Gf, 124 cells, n=3 mice; jGCaMP8f, 317 cells, n=5 mice; jGCaMP8m, 365 cells, n=3 mice; jGCaMP8s, 655 cells, n=6 mice). The boxes indicate medians and 25th-75th percentile range; whiskers indicate the shorter of 1.5 times the 25th-75th range or the extreme data point. Kruskal-Wallis test with Dunn's multiple comparison test. P<0.001. jGCaMP7f vs XCaMP-Gf: P=1.0; jGCaMP7f vs jGCaMP8f: P=0.013; jGCaMP7f vs jGCaMP8m: P=0.029; jGCaMP7f vs jGCaMP8m: P=0.010; jGCaMP7f vs jGCaMP8s: P=0.010; XCaMP-Gf vs jGCaMP8f: P=1.0; XCaMP-Gf vs jGCaMP8m: P=1.0; XCaMP-Gf vs jGCaMP8s: P=0.0027; jGCaMP8f vs jGCaMP8m: P=1.0;

jGCaMP8f vs jGCaMP8s: P<0.001; jGCaMP8m vs jGCaMP8s: P<0.001. * P<0.05; *** P<0.001; ns, not significant. FIG. 13F is a graph showing the proportion of cells detected as responding to visual stimuli. This proportion was significantly higher for jGCaMP8s and jGCaMP8m. jGCaMP7f data: 12 FOVs from n=3 mice; jGCaMP8f, 19 FOVs, n=5 mice; jGCaMP8m, 14 FOVs, n=3 mice; jGCaMP8s, 26 FOVs, n=6 mice. The boxes indicate medians and 25th-75th percentile range; whiskers indicate the shorter of 1.5 times the 25th-75th range or the extreme data point. Data passed Shapiro-Wilk normality test and/or one-way ANOVA test with Tukey's multiple comparison test. P<0.001. jGCaMP7f vs jGCaMP8f: P=0.83; jGCaMP7f vs jGCaMP8m; P=0.0184; jGCaMP7f vs jGCaMP8s: P<0.001; jGCaMP8f vs jGCaMP8m: P<0.001; jGCaMP8m vs jGCaMP8s: P=0.23. * P<0.05; *** P<0.001; ns, not significant. FIG. 13G shows the distribution of response amplitude ($\Delta F/F$) for the preferred stimulus. The jGCaMP8s distribution is significantly right-shifted compared to other jGCaMP versions. Kruskal-Wallis test with Dunn's multiple comparison test was used to compare the magnitude of response across groups. jGCaMP7f vs jGCaMP8f: P<0.001; jGCaMP7f vs jGCaMP8m; P=1.0; jGCaMP7f vs jGCaMP8s: P<0.001; jGCaMP8f vs jGCaMP8m: P<0.001; jGCaMP8m vs jGCaMP8s: P<0.001. The 75th percentile $\Delta F/F0$ (%) values for each construct: 71 (jGCaMP7f), 24 (jGCaMP8f), 59 (jGCaMP8m), 138 (jGCaMP8s). jGCaMP7f, 1,053 cells from n=3 mice; jGCaMP8f, 1,253 cells, n=5 mice; jGCaMP8m, 848 cells, n=3 mice; jGCaMP8s, 1026 cells, n=6 mice.

Figures 14A, 14B, 14C, 14D, 14E, 14F, 14G:
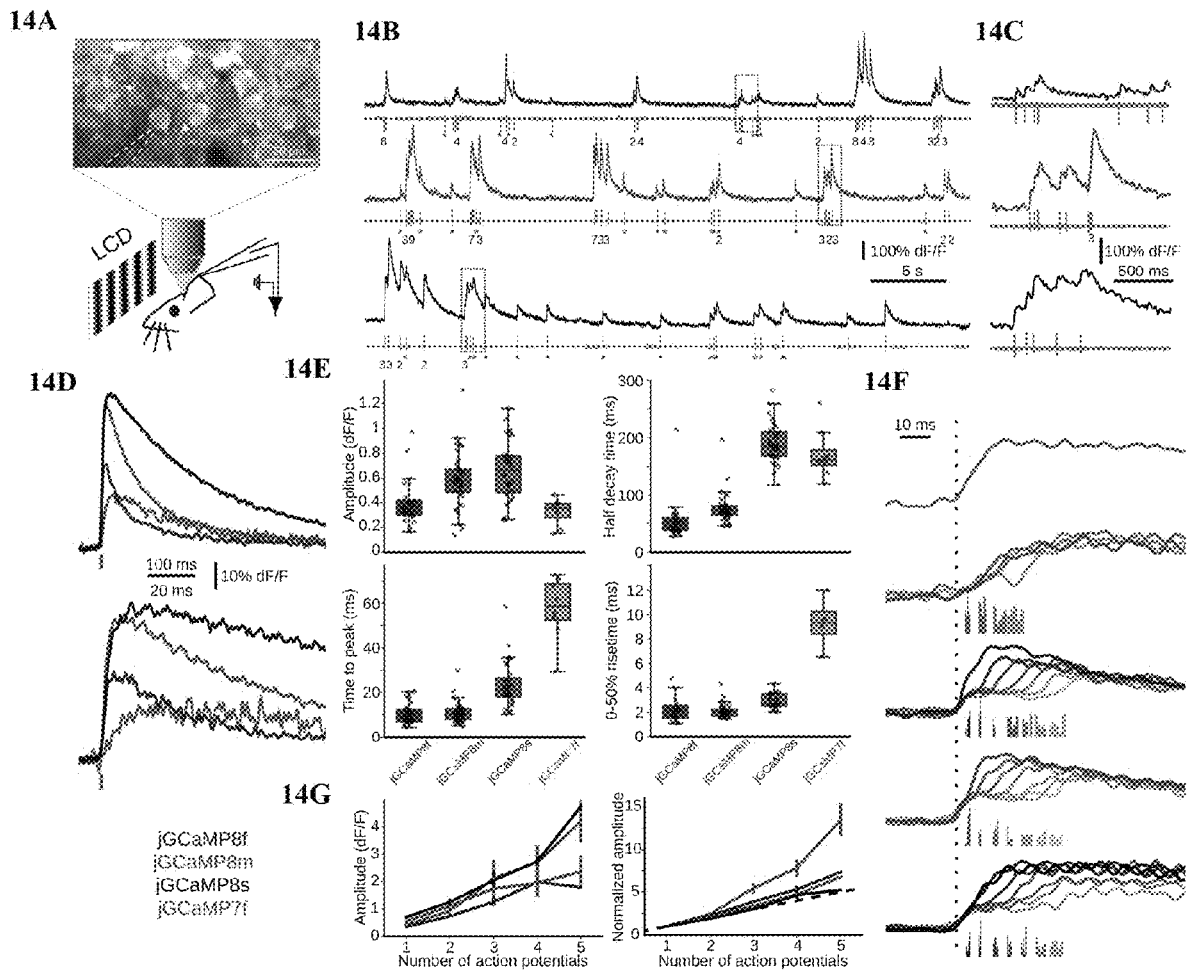

FIG. 14A-14G shows simultaneous electrophysiology and imaging. FIG. 14A is a schematic of the experiment. The inset on top shows a representative field of view. The recording pipette is indicated by dashed lines. FIG. 14B shows the simultaneous fluorescence dynamics and spikes in example neurons expressing jGCaMP8f (top), jGCaMP8m (middle) and jGCaMP8s (bottom). The number of spikes for each burst is indicated below the trace (single spikes, asterisks). Fluorescence traces were filtered with a gaussian filter (o=5 ms). FIG. 14C shows a zoomed-in view of traces corresponding to dashed boxes in FIG. 14B. FIG. 14D shows the grand average of fluorescence response elicited by single action potentials, aligned to action potential peak (red vertical bar), sampled at 500 Hz (see text and FIG. 29). FIG. 14E shows fluorescence responses elicited by single action potentials. Black dots, single cells; bars medians across cells. FIG. 14F shows jGCaMP8 sensors resolve high-frequency action potential trains. Top, jGCaMP7f response to a single action potential (from FIG. 14D). Bottom, response to action potential doublets, binned based on inter-spike intervals. The transients are aligned to the first action potential of the doublet (dotted line). The timing of the second action potential is denoted by the histograms below the transients. The inter-spike intervals are selected to be approximately 5, 10, 15, 20, 25, 30 and 35 ms. FIG. 14G are graphs showing the response linearity. The graph on the left shows peak response as a function of number of action potentials with a 20 ms inclusion window (error bars correspond to s.e.m. across cells) and the graph on the right is the same as on the left but normalized to the peak fluorescence change for a single action potential. Thus, the jGCaMP8 sensors are more linear compared to jGCaMP7f.

Figures 15A, 15B, 15C, 15D, 15E, 15F:
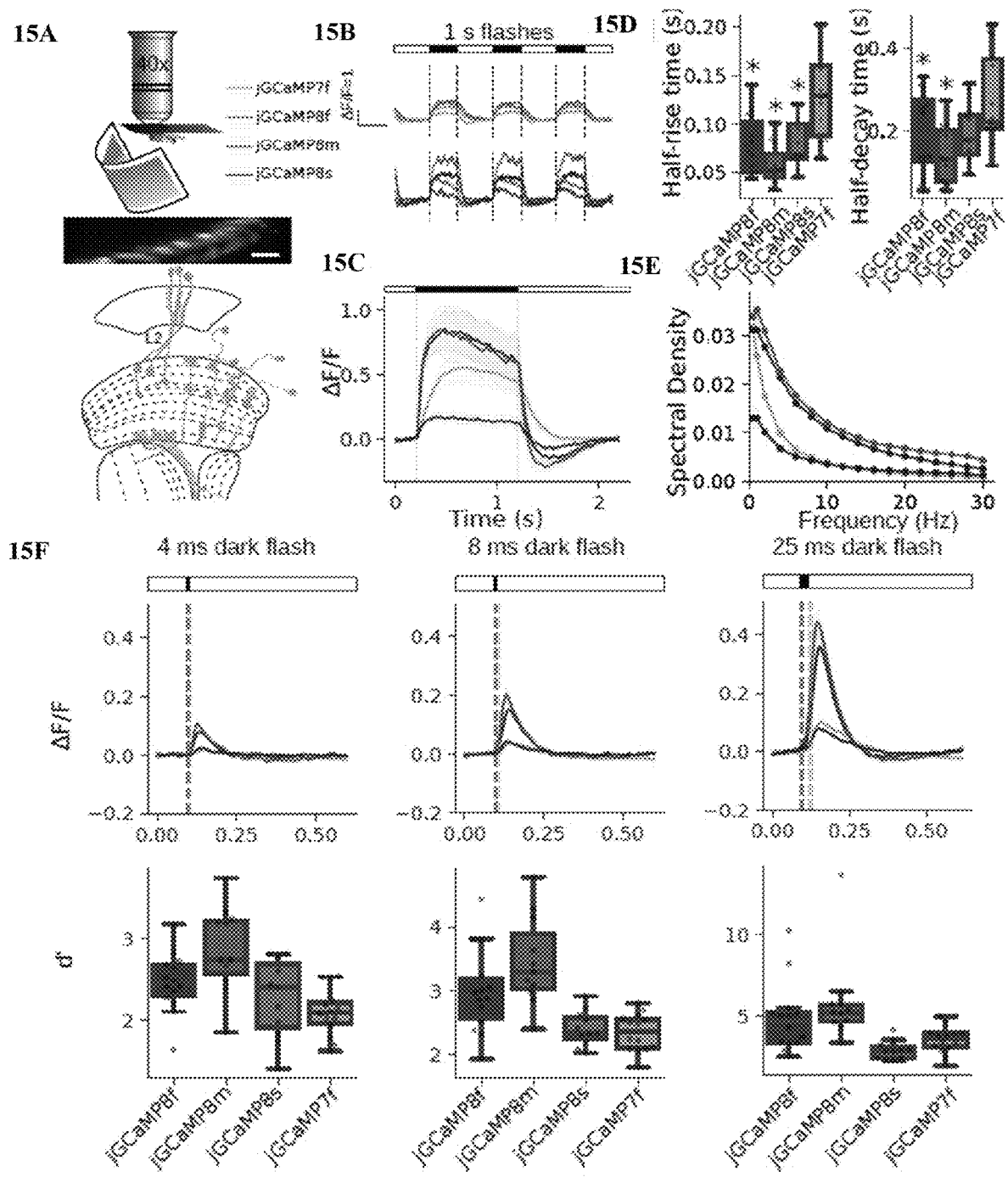

FIG. 15A-15F show jGCaMP8 performance in *Drosophila* L2 neurons. FIG. 15A is a schematic of the experimental setup. Facing an illuminated screen, a female's head and thorax is glued to a pyramidal holder placed under an objective (top); image of the L2 dendrites in layer 2 in the medulla (5 µm bar) (middle) as shown in the schematic of the *Drosophila* visual system (modified from (Fischbach and Dittrich 1989)) (bottom). FIG. 15B show the $\Delta F/F0$ response from 4 individual animals responding to a 0.5 Hz visual stimulation frequency from variants 7f (top) and 8m (bottom). FIG. 15C shows the mean $\Delta F/F$ response to the 0.5 Hz stimulation. Dark line represents mean and shaded area represents standard error. Top, dark period indicates when visual stimulus dims and is indicated within the $\Delta F/F$ graph by dashed vertical lines. FIG. 15D are box plots showing half rise and half decay to dimming onset during the 0.5 Hz stimulation. In half rise, the multi-comparison KW test finds p-2.9E-4 and pair MRS tests to 7f follow: 8f=3.1E-3, 8m=2.9E-5, and 8s=0.013. In half decay, multi-comparison KW finds p=3.6E-3 and pair wise MRS to 7f p-values follow: 8f=7.0E-3, 8m=6.2E-4, and 8s=0.15. FIG. 15E shows the spectral power density measured from L2 responses at stimulation frequencies ranging from 0.5 to 30 Hz. FIG. 15F show the $\Delta F/F$ responses to dark flashes varying by 4, 8, and 25 ms in duration. $\Delta F/F$ plot is as in FIG. 15C; below, box plots describing d'. At 4 ms duration, KW test finds p=2.3E-3 and pair wise MRS to 7f follows: 8f-0.03, 8m=2.0E-4, and 8s=0.24. At 8 ms duration, KW test find p=3.5E-5 and pair wise MRS to 7f follows: 8f=3.5E-3, 8m=2.8E-5, and 8s=0.73. At 25 ms duration, KW test find p=3.4E-5 and pair wise MRS to 7f follows: 8f=0.074, 8m=1.6E-3, and 8s=0.11. Asterisks indicate multi-comparison KW test and MRS pairwise test to 7f to find p<0.05. Unless otherwise stated, all statistics include the following numbers tested: 8f=14, 8m=11, 8s=11, and 7f=14.

Figures 16A, 16B, 16C, 16D, 16E, 16F, 16G:
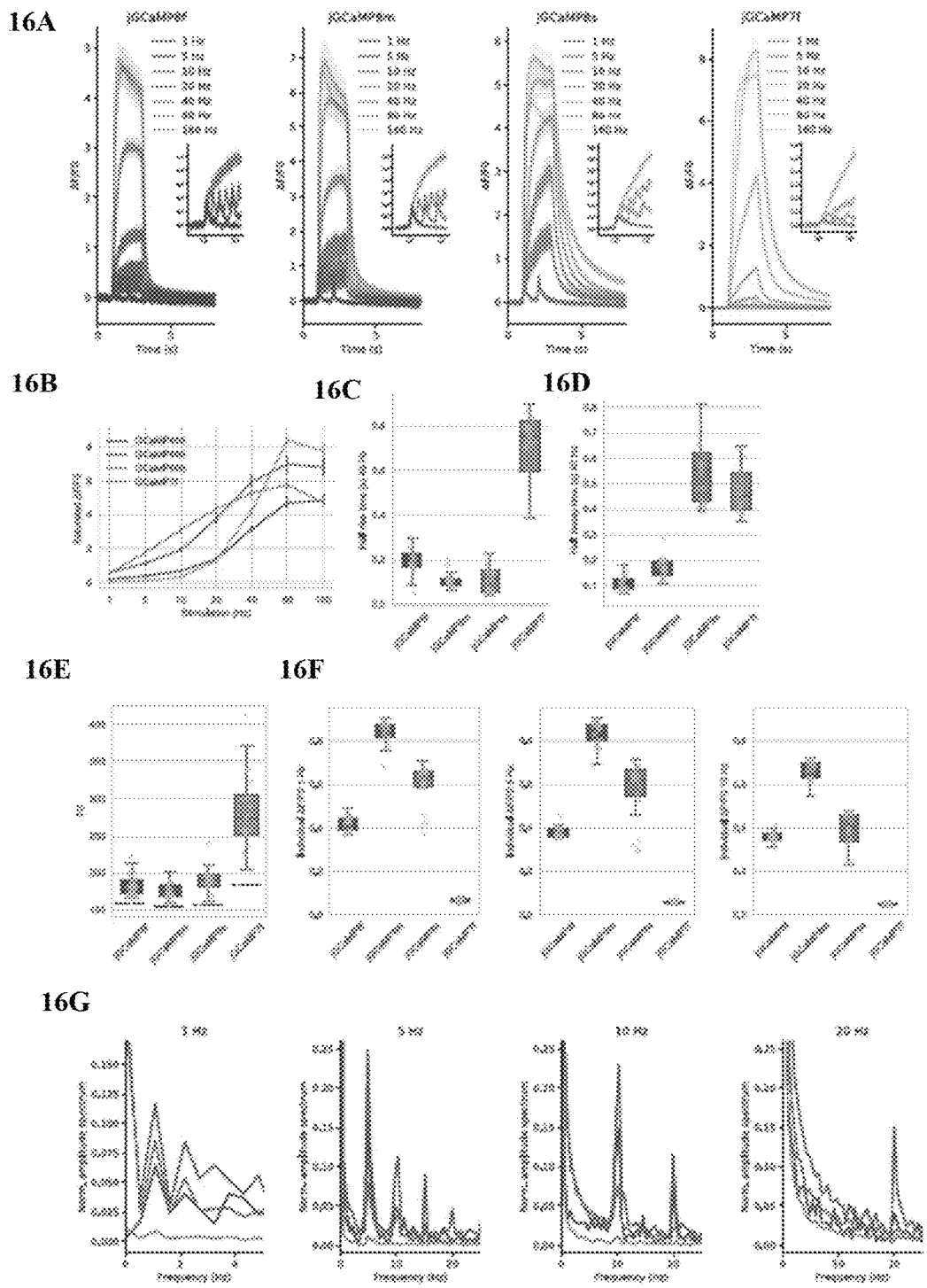

FIG. 16A-16G shows jGCaMP8 performance in neuromuscular junction (NMJ) of larval *Drosophila*. FIG. 16A show frequency response to 1, 5, 10, 20, 40, 80 and 160 Hz stimulation (2 s) of motor axons. Inset: response to 1, 5 and 10 Hz. FIG. 16B show $\Delta F/F_0$ at saturation. FIG. 16C show half-rise time (left) from stimulus onset to saturated peak and half decay time (right) from stimulus end to baseline under 40 Hz stimulation. FIG. 16D show F0 for each sensor. Dashed line indicates the background fluorescence level. FIG. 16E shows an individual response to 1 (left), 5 (middle) and 10 (right) Hz. FIG. 16F shows the power spectral density normalized to 0 Hz for responses to 5 (left), 10 (middle) and 20 Hz (right).

FIG. 17A-17E show biophysical characterization of the sensors. FIG. 17A show Ca2+ titration curves of all peptide-swapped sensors in the original round of optimization. FIG. 17B shows stopped-flow fluorescence titrations of preliminary generations of improved sensors. FIG. 17D shows Ca2+ titrations of the intermediate sensors and stopped-flow fluorescence kinetic traces of second round improved sensors. FIG. 17E shows the crystal structure of jGCaMP8.410.80.

Figures 18A, 18B:
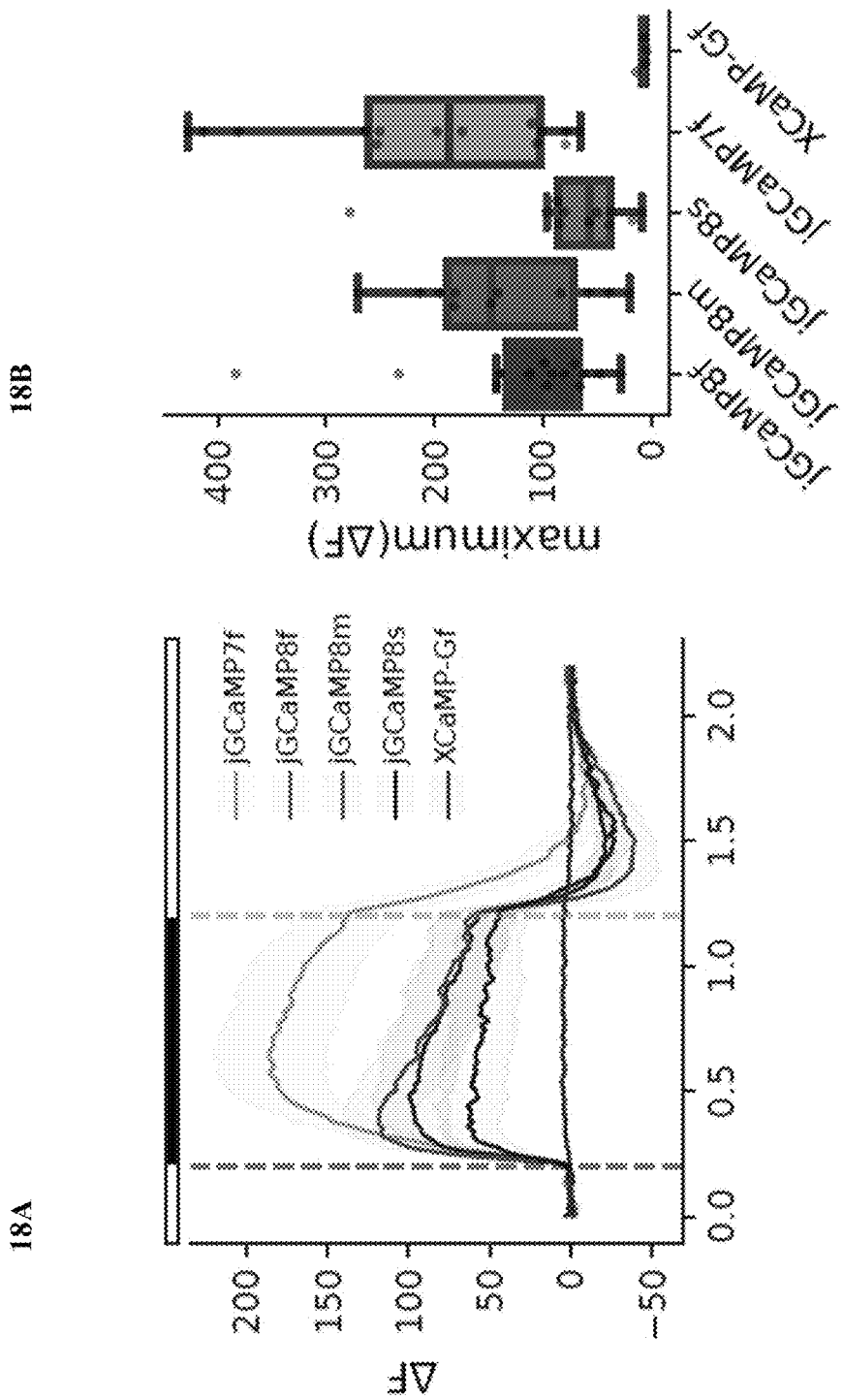

FIG. 18A-18B show quantification of jGCaMP8 and XCaMP performance in the L2 *Drosophila* visual neuron assay. FIG. 18A. $\Delta F$ response during 0.5 Hz visual stimulation. FIG. 18B shows a maximum $\Delta F$ response occurring after the light to dark transition. KW test finds p=4.3E-4 and pair wise MRS to 7f follow: 8f=0.068, 8m-0.29, 8s=2.4E-3, and XCaMP=7E-5. Numbers tested follow: 8f=14, 8m=11, 8s=11, 7f=14, and XCaMP=4. Asterisk indicate multi-comparison KW test and MRS pairwise test to 7f find p<0.05.

Figure 19A:
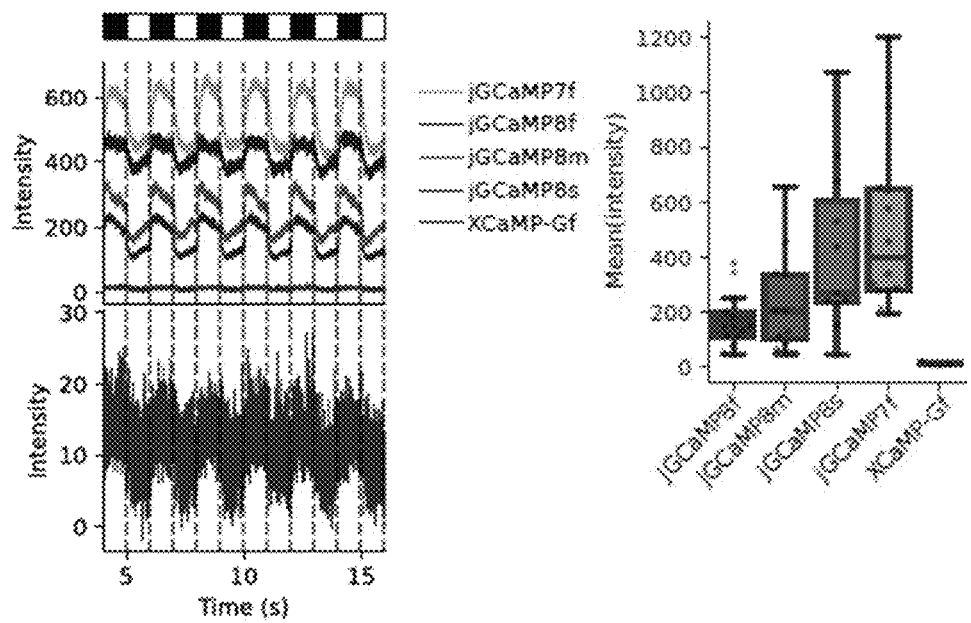
Figure 19B:
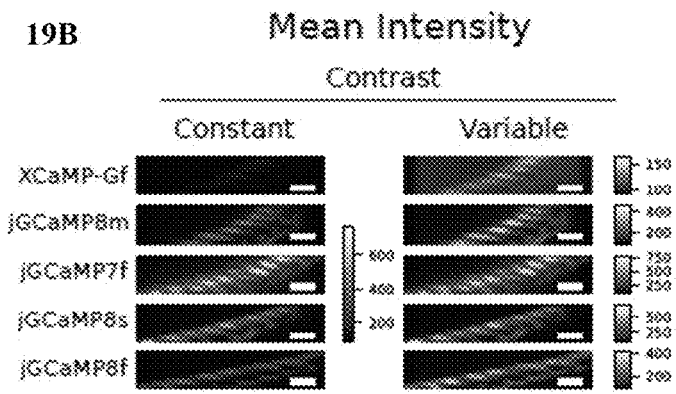
Figure 19C:
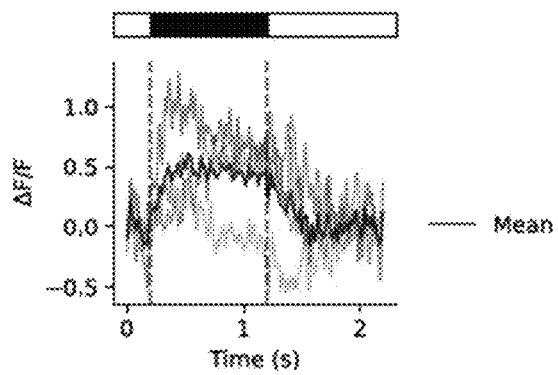

FIG. 19A-19C show further quantification of jGCaMP8 and XCaMP performance in the L2 *Drosophila* visual neuron assay. FIG. 19A shows plots comparing mean intensity during 0.5 Hz stimulation. Top, compares variants using a common axis. Below, the same XCaMP intensity is plotted but the intensity range is adjusted so that intensity changes from XCaMP can be discerned. Right, the mean intensity over the 5 Hz testing period. KW test finds p=5.6E-5 while MRS pair wise comparison to 7f finds: 8f=6.5E-4, 8m=0.014, 8s=0.37, and XCaMP=2.81E-5. In FIGS. 19A and 19B, the numbers tested follow: 8f=14, 8m=11, 8s=11, 7f=14, and XCaMP=4. FIG. 19B shows images that compare mean intensity over the 0.5 Hz stimulation period. Left, the contrast is kept constant between variants to allow comparison. Right, contrast ranges are adjusted to the intensity range for each variant. FIG. 19C shows the mean ΔF/F0 response during a 0.5 Hz stimulation. Black line represents mean between all animals and lighter shades are responses from individual animals.

Figures 20A, 20B, 20C:
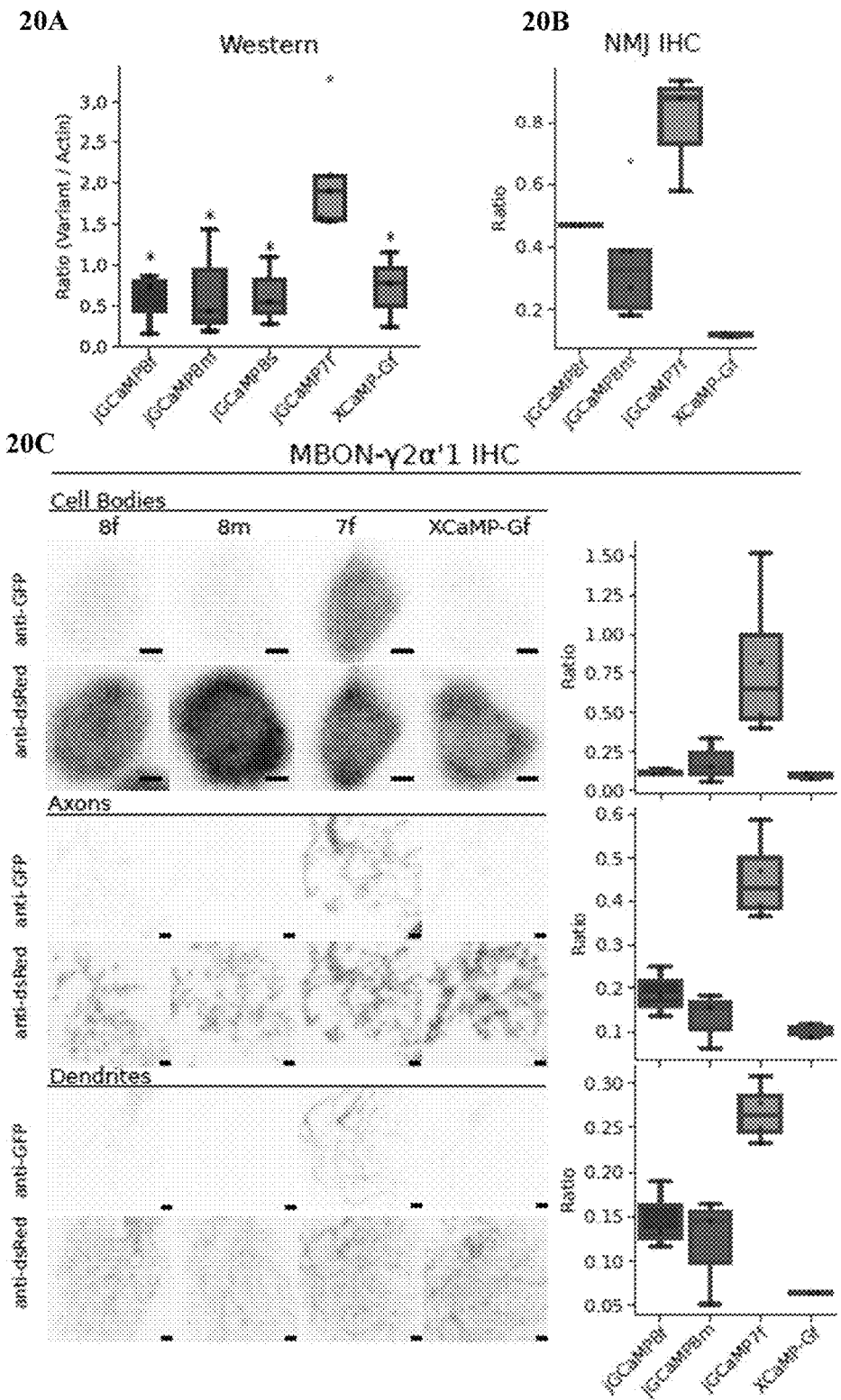

FIG. 20A-20C show protein quantification in *Drosophila* expression. FIG. 20A shows Western blot analysis comparing protein expression between GCaMP variants. Ratio is the band intensity levels from a variant divided by the band intensity from the actin loading control. Multi-comparison KW finds p=0.038 and pair wise MRS to 7f finds the following p-values: 8f=0.011, 8m=0.019, 8s=0.024, and XCaMP=0.038. Numbers tested are as follow: 8f=3, 8m=3, 8s=3, 7f=5, and XCaMP=3. FIG. 20B show a box plot comparing immunostaining at the NMJ. Ratio is the intensity from stain targeting variant divided by intensity from a myr::tdTomato co-expressed with the variant. Multi-comparison KW finds p=0.029 and pair wise MRS to 7f finds the following p-values: 8f=0.37, 8m=0.039, and XCaMP=4.2E-3. Numbers tested are as follow: 8f=2, 8m=6, 7f=3, and XCaMP=2. FIG. 20C shows immunostaining females expressing GCaMP variants and myr::tdTomato in MBON-γ2a'1. Left, images from cell bodies (top), axons (middle), and dendrites (bottom). Bar is 1 µm. Green images show variant expression while red images show myr::tdTomato expression. Right, box plots quantify the ratio between intensity from the variant to the myr::tdTomato. Multi-comparison KW for cell body finds p=0.05. Multi-comparison KW for axon finds p=0.032 and p-values from pair wise MRS comparison follow: 8f=0.13, 8m=0.018, and XCaMP=0.010. Multi-comparison KW for dendrite finds p-0.040 and p-values from pair wise MRS comparison follow: 8f=0.079, 8m=0.034, and XCaMP=0.010. Numbers tested are as follow: 8f=3, 8m=3, 7f-4, and XCaMP=2.

Figure 21:
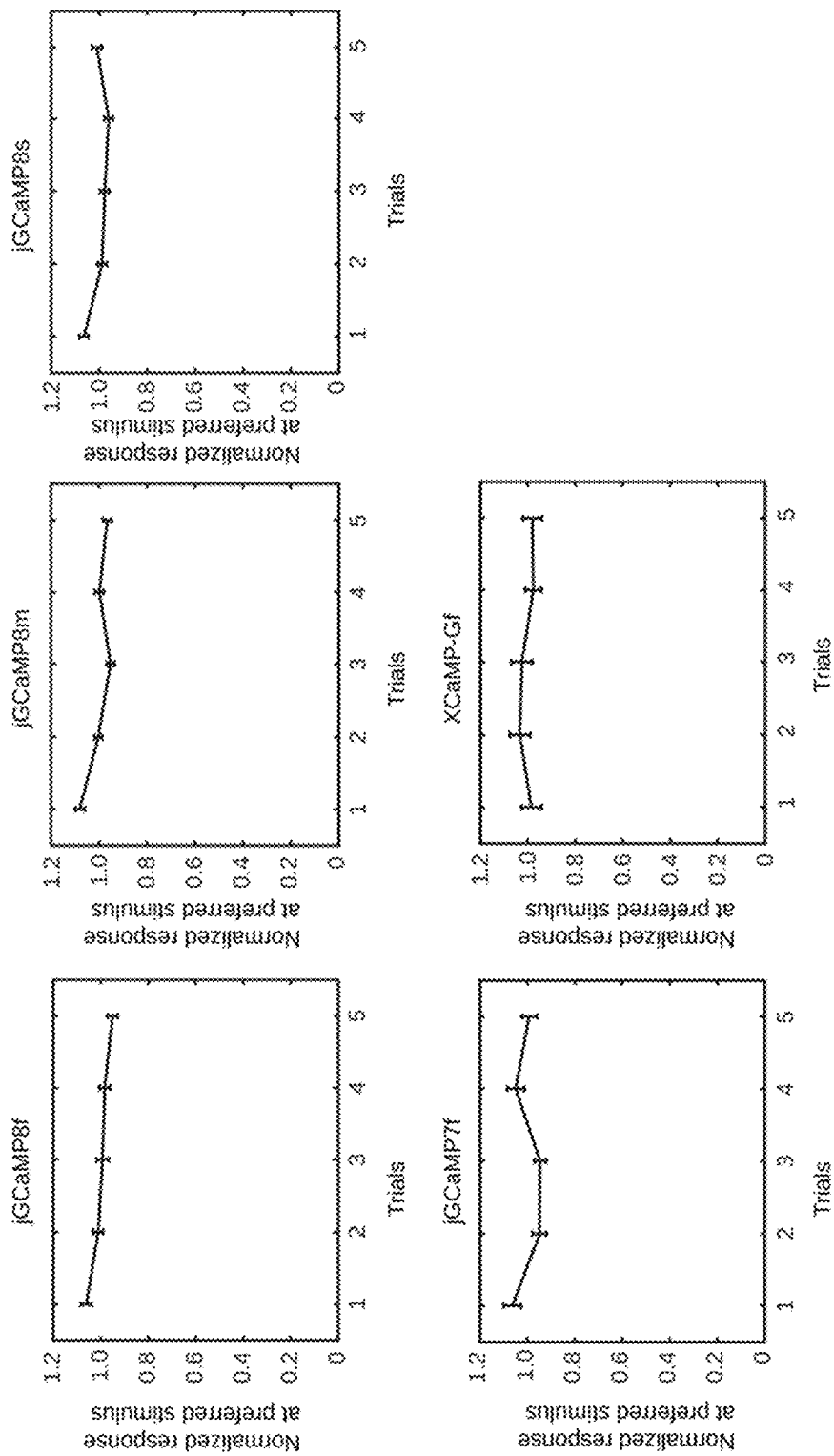

FIG. 21 shows reproducible responses across trials. The peak response amplitude of orientation selective neurons was averaged (jGCaMP8f, 288 neurons; jGCaMP8m, 305 neurons; jGCaMP8s, 420 neurons; jGCaMP7f, 269 neurons; XCaMP-Gf, 121 cells) and plotted as a function of trial number.

Figures 22A, 22B, 22C, 22D:
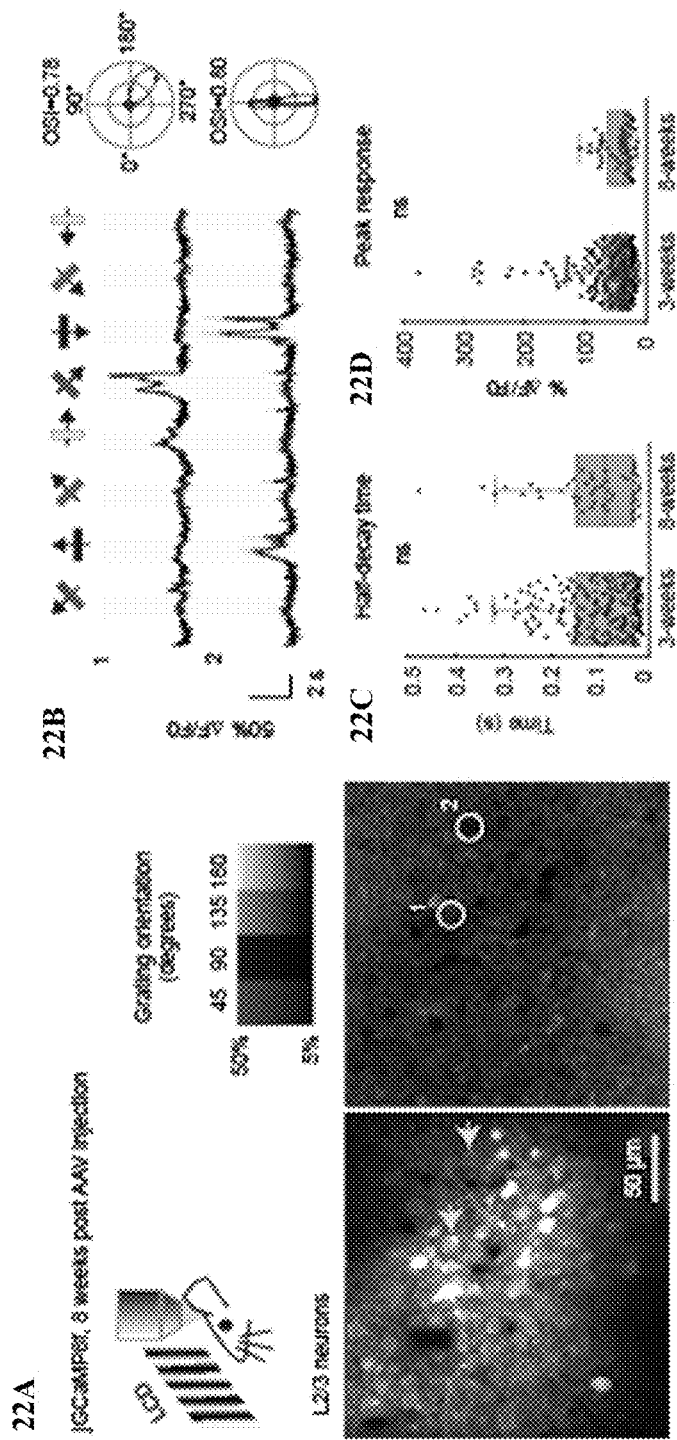

FIG. 22A-22D shows the response comparison between 3 weeks and 8 weeks post AAV infection. FIG. 22A (top) is a schematic of the experiment. Bottom, image of V1 L2/3 cells expressing jGCaMP8f 8 weeks post-AAV injection (left), and the same field of view color-coded according to the neurons' preferred orientation (hue) and response amplitude (brightness). Scale bar, 50 µm. FIG. 22B shows an example traces from two L2/3 neurons in (FIG. 22A). Averages of five trials are overlaid. Eight grating motion directions are indicated by arrows and shown above traces. The preferred stimulus is the direction evoking the largest response. Polar plots indicate the preferred orientation or direction of the cells. OSI values were displayed above each polar plot. FIG. 22C shows comparison of half-decay time for jGCaMP7f between data acquired at 3 weeks and 8 weeks post-AAV injection. 225 cells from 6 mice for 3 weeks' data; 50 cells from 2 mice for 8 weeks' data. The line at the middle of the box correspond to medians, and boxes show the 25th-75th percentile range, whisker length is the shorter of 1.5 times the 25th-75th range or the extreme data point. Two-sided Wilcoxon rank-sum test was used to examine the difference between pairs of groups. P=0.60. FIG. 22D shows the comparison of peak response for jGCaMP7f between data acquired at 3 weeks and 8 weeks post-AAV injection. 225 cells from 6 mice for 3 weeks' data; 50 cells from 2 mice for 8 weeks' data. The line at the middle of the box correspond to medians, and boxes show the 25th-75th percentile range, whisker length is the shorter of 1.5 times the 25th-75th range or the extreme data point. Two-sided Wilcoxon rank-sum test was used to examine the difference between pairs of groups. P=0.053.

Figures 23A, 23B, 23C, 23D:
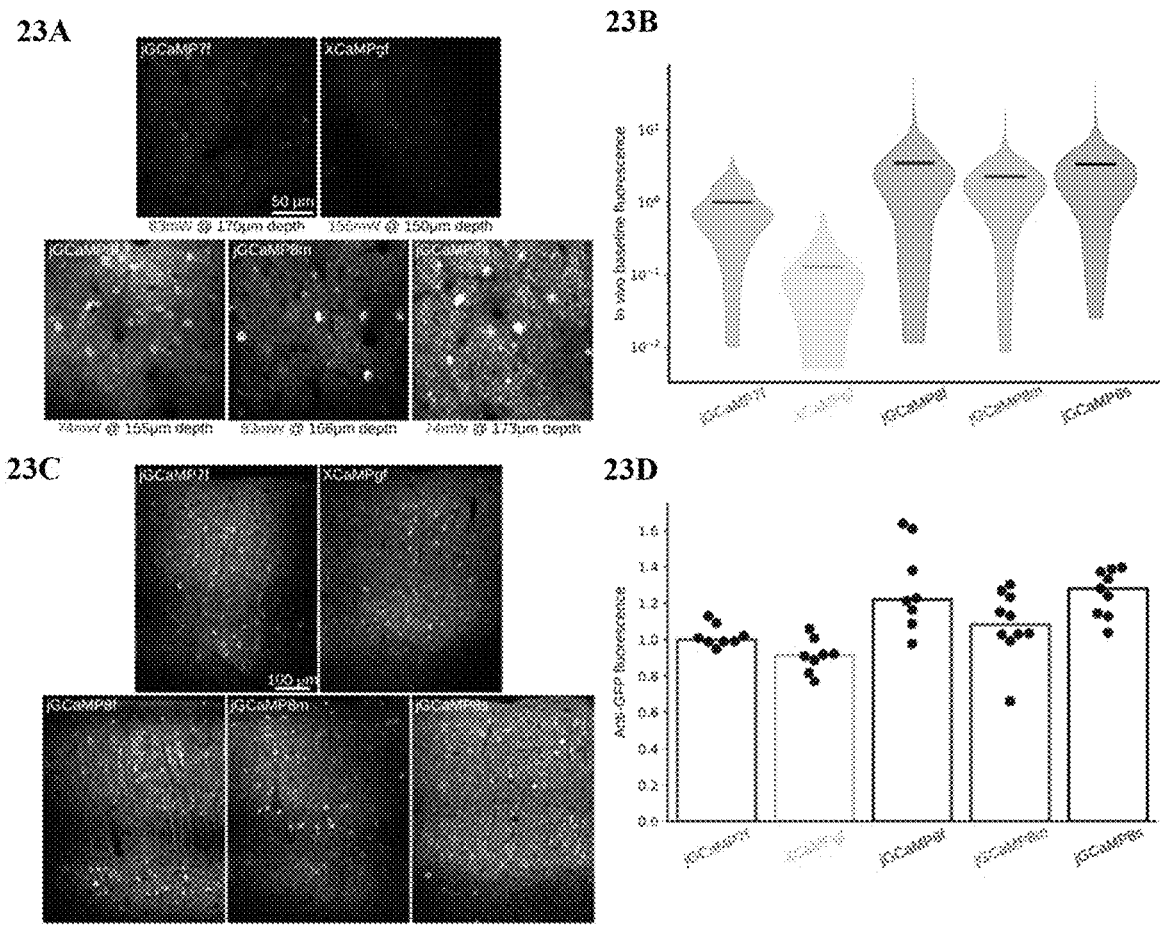

FIG. 23A-23D shows brightness in vivo and expression level. FIG. 23A shows representative in vivo average movies for all GECIs. The post-objective illumination power and the depth of imaging is noted under each image. The color axis is the same for all images. FIG. 23B shows in vivo distribution of excitation power corrected baseline fluorescence values for segmented cellular ROIs. Horizontal bars represent the median of each distribution. Note the logarithmic seale. All data were normalized to the median of the jGCaMP7f distribution. See FIG. 23A for representative motion corrected in vivo two-photon movie averages. FIG. 23C shows representative images of anti-GFP fluorescence for all GECIs in a coronal section across the center of an injection site, 20-22 days post injection. The color axis is the same for all images. FIG. 23D shows maximal fluorescence of the anti-GFP antibody at the center of the injection sites for all sensors, 20-22 days post injection. The maximum was obtained after applying a gaussian filter (σ=50 µm). A dot represents an injection site, the colored bars represent the median for each sensor. All data was normalized to the median of the jGCaMP7f values. Note that the expression levels are similar across sensors and injection sites. See FIG. 22E for representative images of injection centers. The data is collected from two mice for each sensor.

Figures 24A, 24B:
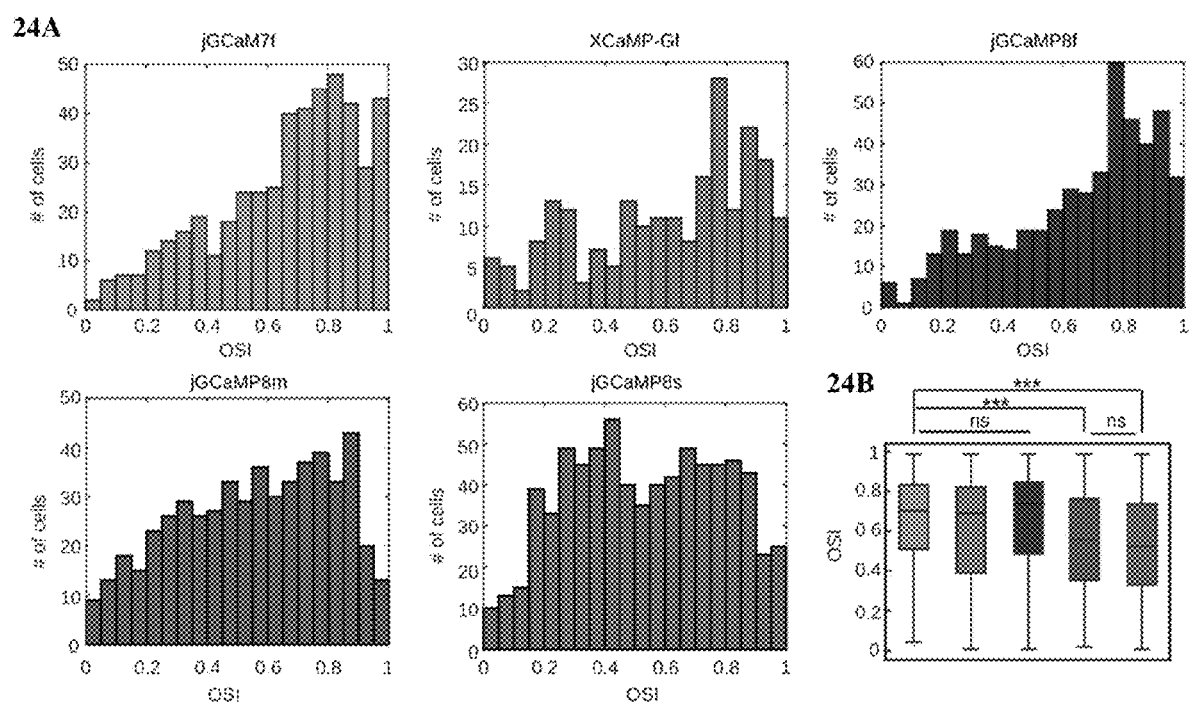

FIG. 24A-24B shows the orientation tuning in V1 neurons. FIG. 24A shows the distribution of orientation selectivity index (OSI) for visually responsive cells measured using different sensors (n=473 cells, jGCaMP7f; 221, XCaMP-Gf; 484, jGCaMP8f; 532, jGCaMP8m; 742, GcaMP8s). There is a left-shift in the distributions of OSI for jGCaMP8m and jGcaMP8s. FIG. 24B shows the comparison of OSI values across sensors (same data as in FIG. 24A). Red lines correspond to medians, each box shows the 25th to 75th percentile range, whisker length is the shorter of 1.5 times the 25th to 75th range or until the extreme data point. Kruskal-Wallis test (P<0.001) with Dunn's multiple comparison test was used for statistics. jGCaMP7f vs XCaMP-Gf: P=0.13; jGCaMP7f vs jGCaMP8f: P=1.0; jGCaMP7f vs jGCaMP8m; P<0.001; jGCaMP7f vs jGCaMP8s; P<0.001; jGCaMP8m vs jGCaMP8s: P=1.0. *** P<0.001. ns, not significant.

Figure 25A:
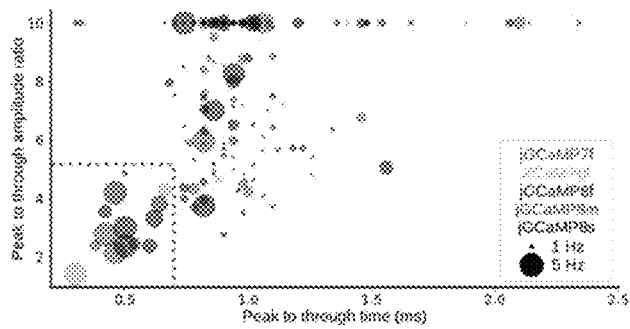
Figure 25B:
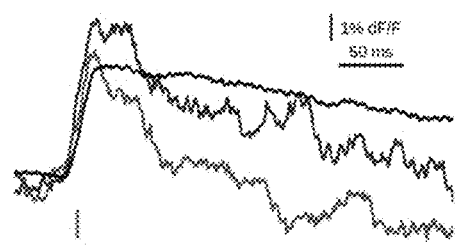
Figure 25C:
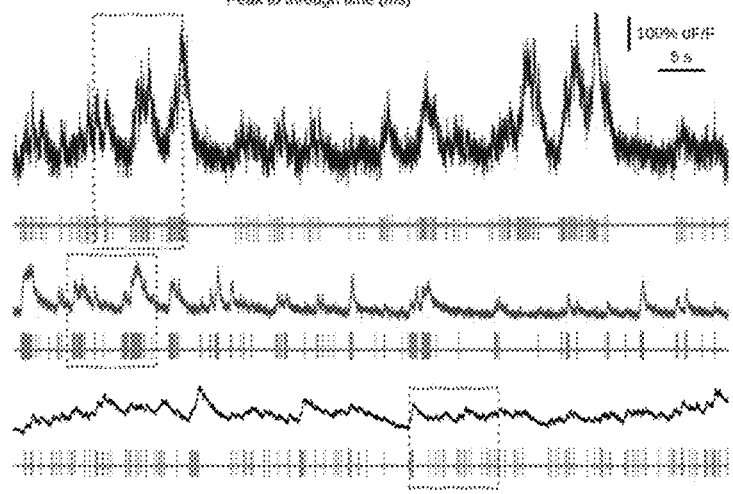
Figure 25D:
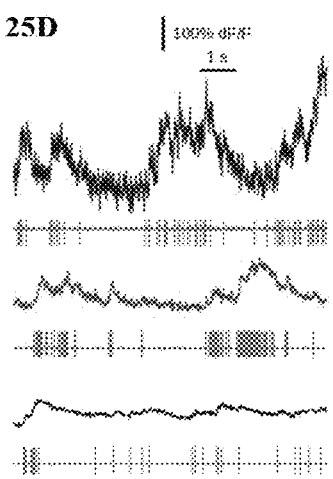

FIG. 25A-25D shows responses in fast-spiking interneurons. FIG. 25A show spike waveform parameters for each recorded cell, colors represent the expressed sensor, size of the circle represent average firing rate. Peak-to-trough ratios larger than 10 are plotted as 10. We defined putative interneurons as cells that occupy the lower left quadrant of this figure, borders highlighted with red dotted lines. FIG. 25B shows the average calcium transient waveform for a single action potential in putative interneurons for the jGCaMP8 series sensors. Resampling was done with a 20 ms long mean filter. FIG. 25C shows simultaneous fluorescence dynamics and spikes in a jGCaMP8f (top), jGCaMP8m (middle) and jGCaMP8s (bottom) expressing putative interneuron. Fluorescence traces were filtered with a gaussian filter (σ=5 ms). FIG. 25D shows a zoomed-in view of bursts of action potentials from FIG. 25C (top, jGCaMP8f; middle, jGCaMP8m; bottom, jGCaMP8s).

Figures 26A, 26B, 26C, 26D:
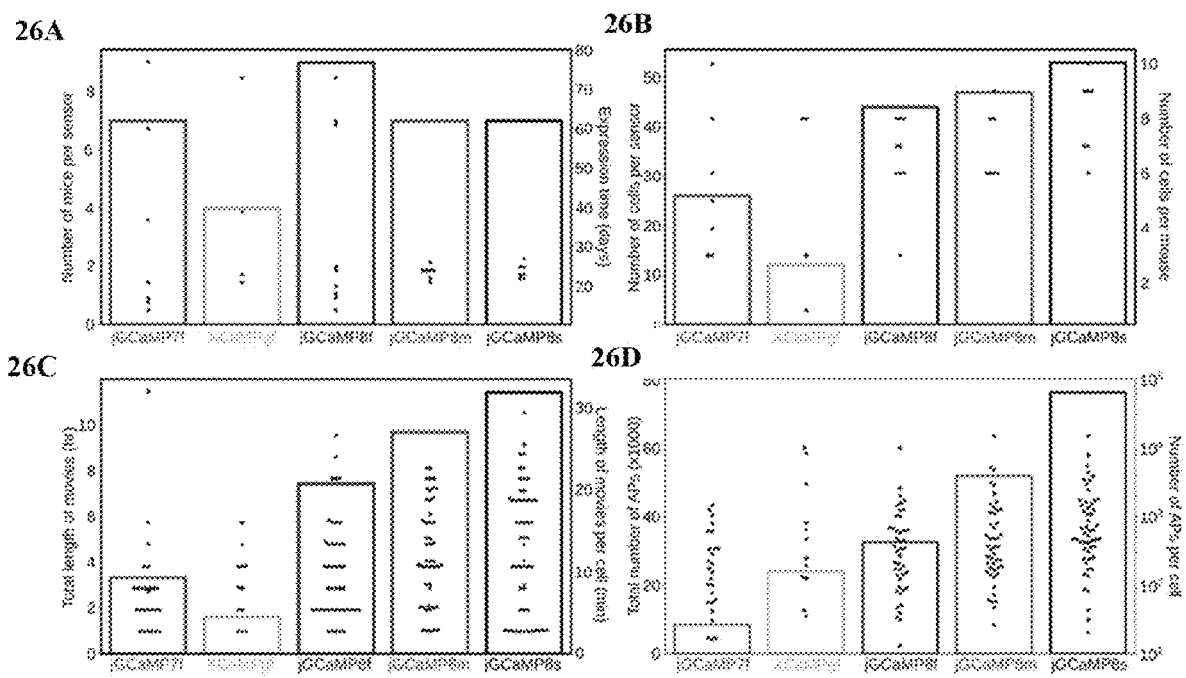

FIG. 26A-26D shows descriptive statistics for loose-seal cell-attached recordings. FIG. 26A shows a summary plot showing the number of mice used (bars, left y axis) and the expression time at the time of the loose seal recording in days (dots, right y axis), for each sensor. FIG. 26B shows a summary plot showing the total number of cells recorded (bars, left y axis), and the number of cells recorded per mouse (dots, right y axis) for each sensor. FIG. 26C shows a summary plot showing the total length of simultaneous imaging and loose-seal recordings in hours (bars, left y axis), and the length of simultaneous imaging and loose-seal recordings in minutes for each cell (dots, right y axis). FIG. 26D shows a summary plot showing the total number of action potentials (bars, left y axis), and the number of recorded action potentials for each cell (dots, right y axis), for each sensor.

Figure 27A:
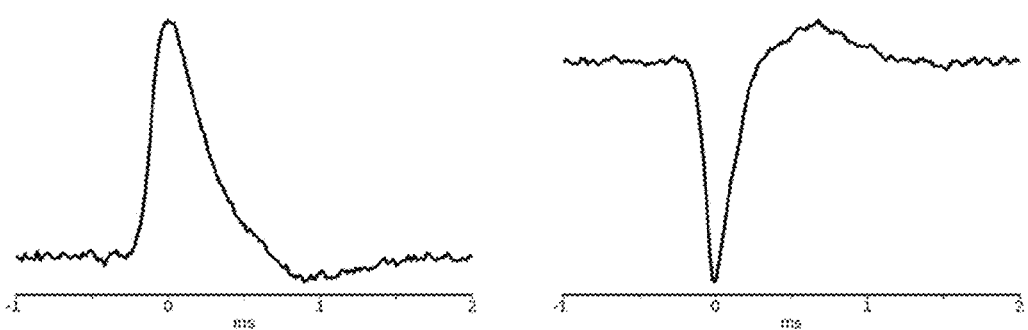
Figure 27B:
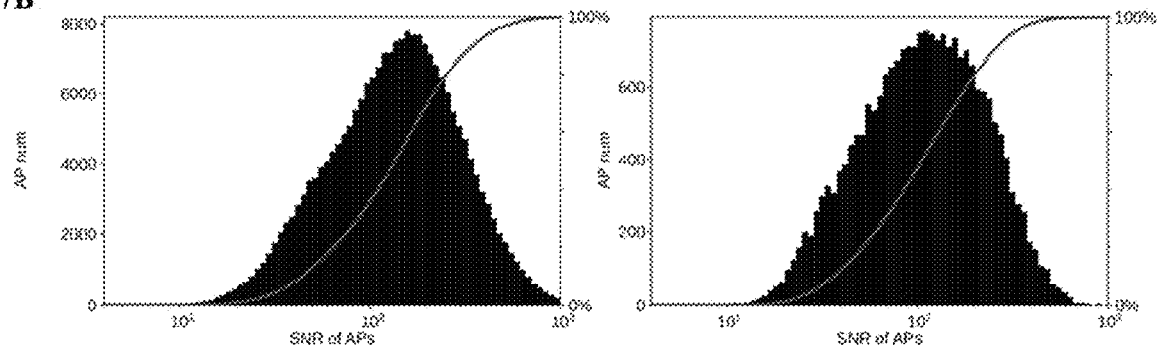

FIG. 27A-27B shows signal-to-noise ratio of action potential recordings. FIG. 27A shows representative waveforms of loose-seal recorded action potentials in current clamp (left) and voltage clamp (right) recording mode. FIG. 27B shows distribution of action potential waveform parameters for all recorded spikes in current clamp (left) and voltage clamp (right) recording mode.

Figures 28A, 28B, 28C, 28D:
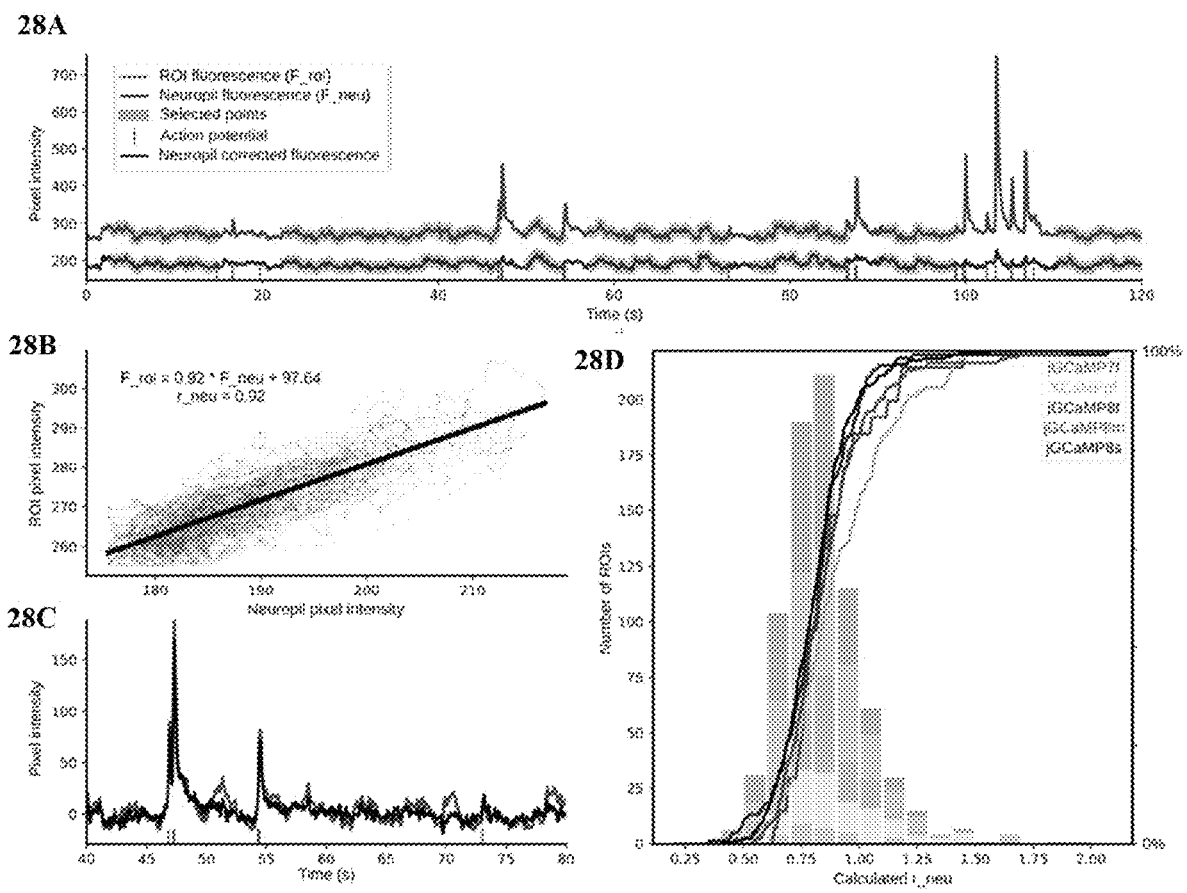

FIG. 28A-28D are experimental results. FIG. 28A shows a representative fluorescence trace for a cellular ROI (green) and its surrounding neuropil (blue) with simultaneous loose-seal recording. For calculating the distribution of neuropil contamination coefficients (r_neu), we didn't include time points during the 3 seconds after an electrophysiologically recorded action potential (red vertical bars). Time points that are included in the analysis are highlighted in red. Note the correlation between cellular and neuropil ROI. Traces were high-pass filtered using a 10-second-long minimum filter and low-pass filtered with a gaussian filter (σ=10 ms). FIG. 28B shows cellular ROI pixel intensity values plotted against their corresponding neuropil pixel intensity values (time points highlighted with red on FIG. 28A), and their linear fit. The neuropil contamination coefficient is defined as the slope of this fitted function. FIG. 28C shows raw and neuropil corrected trace from FIG. 28A, corrected with the neuropil contamination coefficient calculated in FIG. 28B. (F_corr=F_roi−r_neu*F_neu). FIG. 28D shows the distribution of r_neu values, each calculated on 3-minute long simultaneous optical and electrophysiological recordings as shown in FIG. 28A-28B. We included r_neu values only with a Pearson's correlation coefficient >0.7. Colors represent different GECIs.

Figures 29A, 29B, 29C, 29D, 29E, 29F:
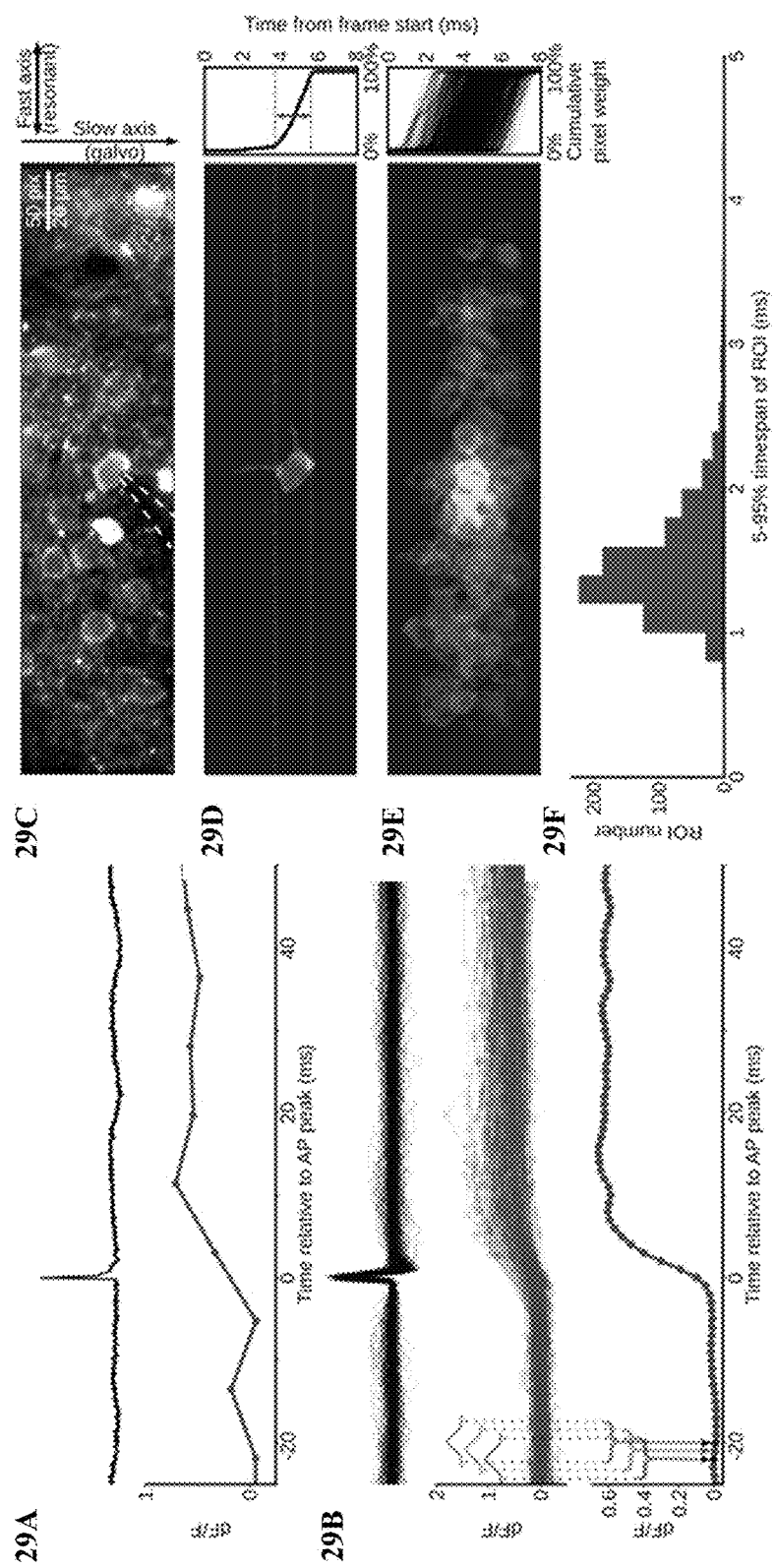

FIG. 29A-29F shows super-resolution imaging of jGCaMP8 activity in vivo in mouse visual cortex. FIG. 29A shows an example isolated action potential during a simultaneous loose-seal recording at 50 kHz (top panel) and imaging at 122 Hz (bottom panel) of a jGCaMP8s expressing neuron. FIG. 29B shows the same as in FIG. 29A but 250 isolated action potentials are aligned to the peak of the action potential and overlaid. Note that the timing of the frames (green dots on middle panel) are uniformly distributed in time. Bottom panel shows the construction of the high-resolution resampled trace. Each point in the resampled trace is generated by averaging the surrounding time points across the population of calcium transients with a Gaussian kernel. Three example points are highlighted with black, red and blue colors, together with the time span and weight used for the calculation of each point. FIG. 29C shows the mean intensity projection of a representative field of view during cell attached loose-seal recording. Recording pipette is highlighted with dashed white lines. The right panel shows how each frame is generated: the horizontal axis is scanned with a resonant scan mirror, the speed of which can be considered instantaneous compared to the vertical axis. The vertical axis is scanned with a slower galvanometer mirror, the speed of which determines the frame rate. FIG. 29D shows the cellular ROI of the loose-seal recorded cell on FIG. 29C. Color seale show pixel weights for ROI extraction. Right panel shows cumulative pixel weight over the generation of a frame. We defined the timespan of the ROI as the 5-95% time of the cumulative pixel weight function. The timespan of the ROI is denoted with a red two-headed arrow. FIG. 29E shows all loose-seal recorded ROIs weights overlaid as on FIG. 29D. A ROI was defined on three minutes long movies, so one recorded cell can have multiple overlapping ROIs on this image. FIG. 29F shows distribution of 5-95% timespans of all recorded ROIs. The timespan of the majority of the ROIs are under two milliseconds, thus the upper bound of the temporal resolution is 500 Hz.

Figures 30A, 30B, 30C, 30D:
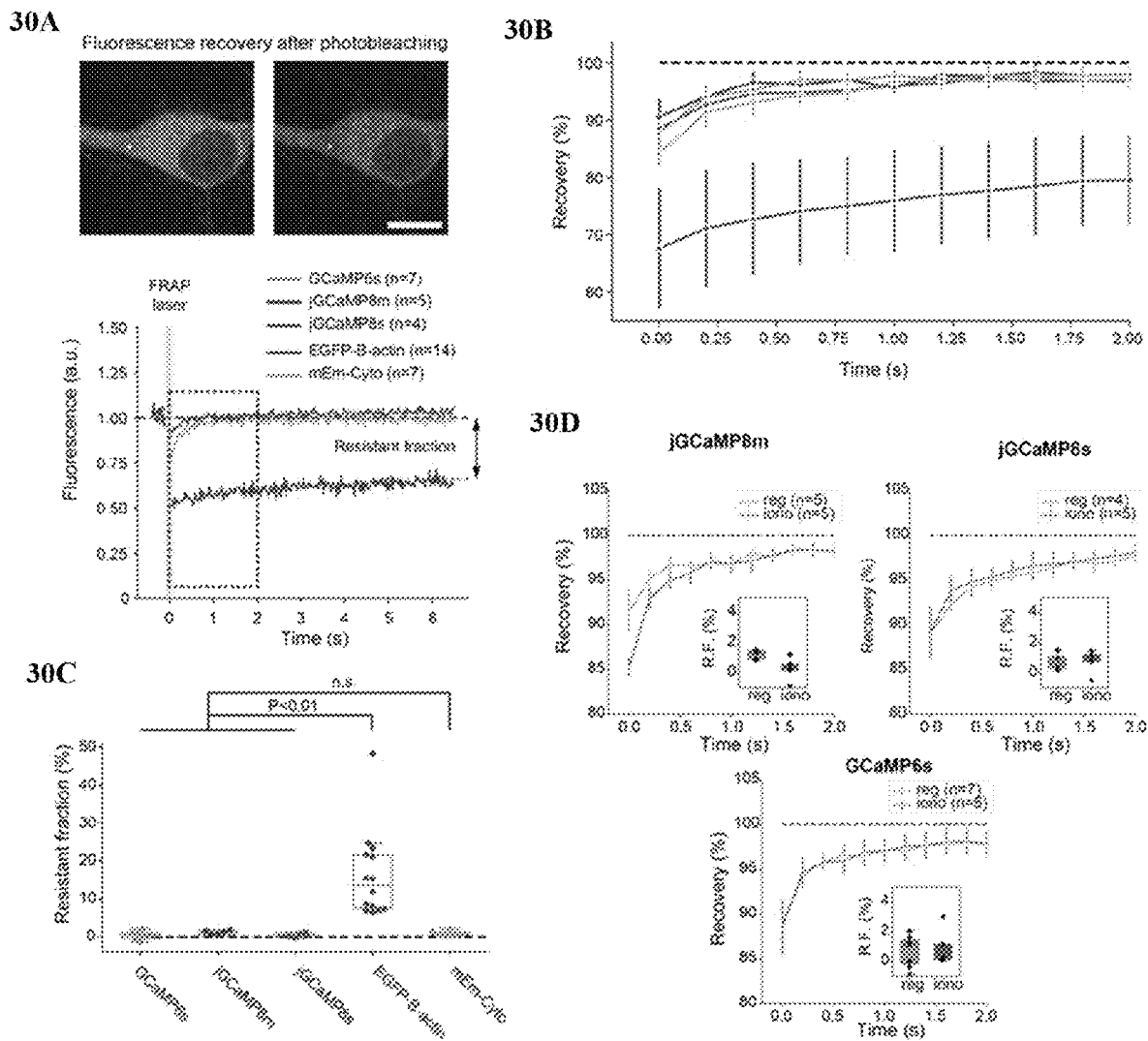

FIG. 30A-30D shows fluorescence recovery after photobleaching (FRAP) measurements of the jGCaMP8 sensors. FIG. 30A (top) shows cellular images of expressing neuron before (left) and after (right) focal photobleaching of the jGCaMP8 sensor and (bottom) quantification of cytoplasmically expressed jGCaMP8m, jGCaMP8s, GCaMP6s, and mEmerald, as well as GFP fused to b-actin. FIG. 30B shows average data over 5 replicates of each sensor or fluorescent protein. FIG. 30C shows quantification of the fit data from FIG. 30B, showing that only EGFP fused to b-actin shows a substantial fraction of protein that is resistant to replacement following photobleaching. All GCaMP sensors behave similarly. FIG. 30D shows that treatment of the neurons with the Ca2+ ionophore ionomycin does not significantly affect the photobleaching time.

Figures 31A, 31B, 31C, 31D, 31E, 31F, 31G, 31H, 31I, 31J, 31K, 31L:
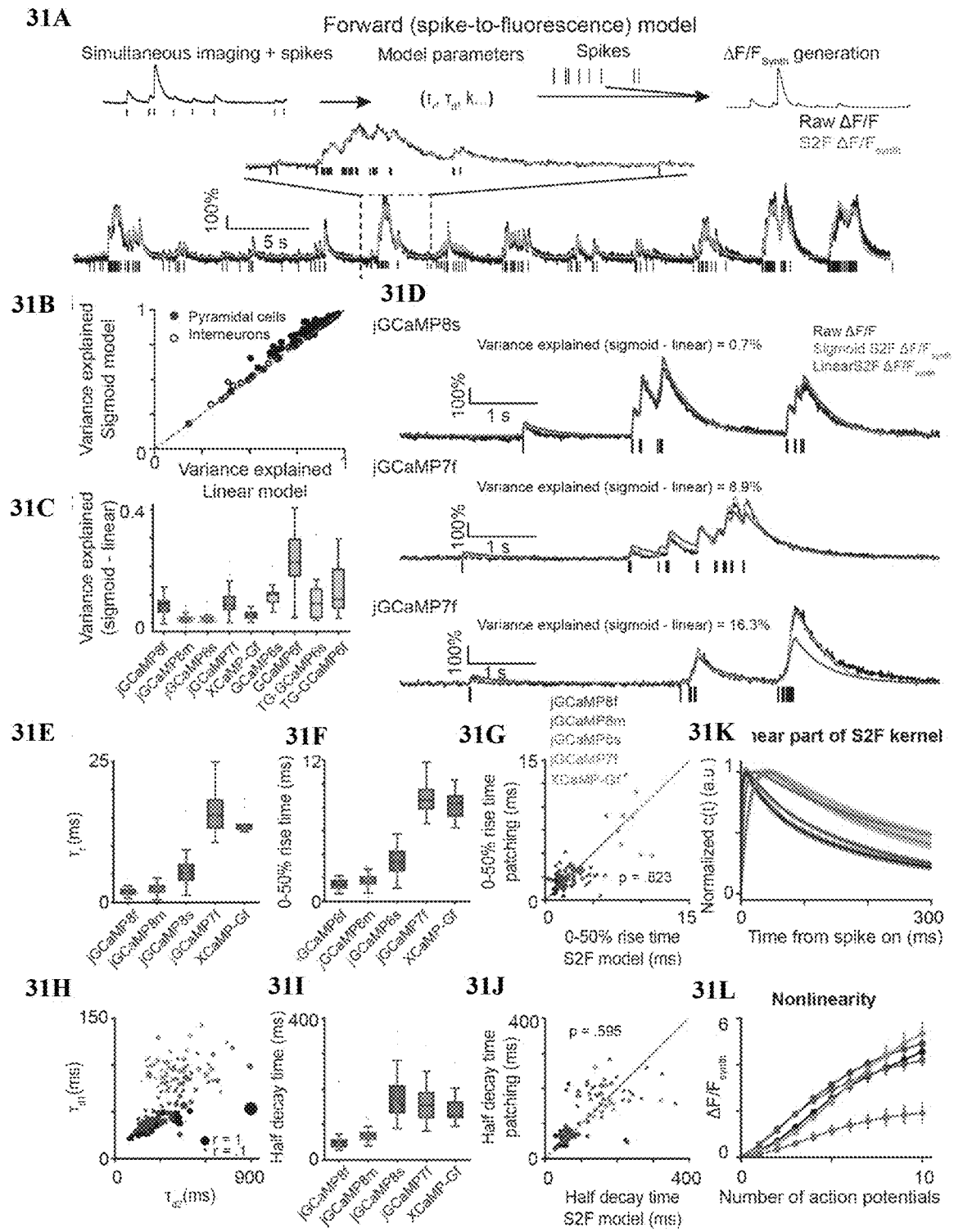

FIG. 31A-31L shows experimental results. FIG. 31A shows a spike-to-fluorescence model. Top: schematic plot of the spike-to-fluorescence (S2F) forward model that generates a synthetic fluorescence trace (ΔF/FSynth) from an input spike train. Bottom: example fit and data of a cell. Experimental, measured ΔF/F (black) is overlaid with the simulated ΔF/FSynth (gray) from the S2F model. The input to the model, the simultaneously recorded spikes (black), is shown below the traces. FIG. 31B shows the comparison of goodness of fits (measure by variance explained) of jGCaMP8 sensors using sigmoid model versus linear model (sigmoid model is better, paired t-test: pyramidal cells, black close dots, N=120, t=9.87, p<. 0001; interneurons, open dots, N=13, t=3.70, p=. 0031). Red line is the diagonal line. FIG. 31C shows the degree of nonlinearity (measured by the difference of variance explained used sigmoid fit from that used linear fit). Nonlinearity is weak in jGCaMP8 sensors (see Table 4 for more details) and that is strong in GCaMP6 sensors. FIG. 31D shows exemplary cell dynamics with different degrees of nonlinearities. Black lines, measured ΔF/F; gray lines, simulated ΔF/FSynth from the S2F sigmoid model; magenta lines, simulated ΔF/FSynth from the S2F linear model. FIG. 31E-31J shows statistics of S2F fits in the different imaging conditions (See Table 5 for more details). Blue, jGCaMP8f; red, jGCaMP8m; dark gray, jGCaMP8s; green, jGCaMP7f; cyan, XCaMP-Gf. FIG. 31E shows boxplots of rise time, tr. FIG. 31F shows boxplots of 0-80% peak rise time derived from S2F fits. FIG. 31G shows comparison between 0-80% peak rise time derived from S2F fits (x-axis) with that measured by super-resolution patch data (y-axis; see FIG. 22E for more details). Red dash line is the diagonal line. FIG. 31H shows scatter plots of decay times. X-axis, the slow decay time, rd2; y-axis, the fast decay time, τd1; size of dots, the ratio of the weight for fast kinetic to that for the slow one, r. FIG. 31I shows boxplots of half decay time derived from S2F fits. FIG. 31J shows comparison between half decay time derived from S2F fits (x-axis) with that measured by super-resolution patch data (y-axis; see FIG. 22E for more details). Red dash line is the diagonal line. FIG. 31K-31L show the simulated ΔF/FSynth predicted from the S2F models of different sensors. FIG. 31K shows normalized synthetic calcium latent dynamics, c(t); solid lines, mean; shaded area, s.e.m. FIG. 31L shows simulated peak nonlinearity, i.e., synthetic fluorescence response to different numbers of action potentials. Error bars, s.e.m. across cells.

DETAILED DESCRIPTION

Genetically encoded calcium indicators (GECIs) (also called fluorescent calcium indicator proteins; FCIPs) provide an alternative to synthetic indicators. GECIs can be easily targeted to specific cell types or sub-cellular compartments, and are compatible with long-term, repeated in vivo measurements. GECIs consist of a calcium-binding domain such as calmodulin or troponin C, fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs and multiple-FP GECIs, calcium binding modulates fluorescence resonance energy transfer (FRET) between FPs.

Among single-FP based GECIs, the GCaMP family has found the broadest use across multiple model organisms. The properties of GCaMP variants are superior to synthetic indicators in terms of signal-to-noise ratio (SNR) but are still inferior to synthetic indicators in terms of response linearity.
Nucleic Acid and Polypeptide Compositions As described herein, improved GCaMP variants, referred to as "GCaMP8" variants (or "jGCaMP8" variants) were developed and characterized. The sequence of GCaMP includes a peptide that binds to calmodulin, a circularly permuted GFP, and calmodulin. In previous GCaMP constructs, the calmodulin-binding peptide was RS20, a fragment of smooth muscle myosin light chain kinase. The novelty of the jGCaMP8 variants stems from the substitution of RS20 with a number of other calmodulin-binding peptides that have not previously been used in GECIs (see, e.g., SEQ ID NOs: 25-55 or residues 10-29 of any of SEQ ID NO:1, SEQ ID NO:3, SEQ ID NO:5, SEQ ID NO:7, SEQ ID NO:9, SEQ ID NO: 11, SEQ ID NO:13, SEQ ID NO:15, SEQ ID NO:17, SEQ ID NO: 19, or SEQ ID NO:21). The most successful peptides were derived from endothelial nitric oxide synthase and death-associated protein kinase 1. In particular, GCaMP variants that included the peptide from endothelial nitric oxide synthase showed much faster rise and decay kinetics resulting from exposure to Ca2+ in purified protein, in cultured neurons following elicitation of action potentials with electrical stimuli, and in living animals following behavioral stimuli.

As described herein, the jGCaMP8 variants described herein show a reduction in half-rise time, a reduction in peak time, an increase in ΔF/F$_0$, and an increase in signal-to-noise ratio (SNR) in response to 1 AP stimulation compared to jGCaMP7f (Table 2). Overall, the sensors described herein are optimized for detecting single action potentials with fast kinetics and high sensitivity. The rise and decay kinetics and the SNR of the disclosed variants are superior to all existing GECIs.

Provided herein are nucleic acid sequences encoding genetically encoded calcium indicators (GECIs) such as those designated jGCaMP8f, jGCaMP8s, and jGCaMP8m. In some embodiments, the encoded jGCaMP8 polypeptide having the amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21, or a calmodulin-binding peptide having the amino acid sequence shown in SEQ ID NOs: 25-55 or having residues 10-29 of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21, optionally includes one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 or any of SEQ ID NOs: 25-55 is expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, or any of SEQ ID NOs: 25-55 can be substituted with a conservative amino acid(s), so long as the desired function of the peptide is maintained (e.g., substantially maintained). For example, in some instances, the nucleic acid sequence can comprise SEQ ID NO:2, SEQ ID NO:4, SEQ ID NO:6, SEQ ID NO:8, SEQ ID NO:10, SEQ ID NO: 12, SEQ ID NO: 14, SEQ ID NO:16, SEQ ID NO: 18, SEQ ID NO:20, SEQ ID NO:22, or any of SEQ ID NOs: 25-55. In some embodiments, the nucleic acid sequence can consist or consist essentially of SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO:18, SEQ ID NO:20, SEQ ID NO:22, or any of SEQ ID NOs: 25-55.

Also provided are jGCaMP8 polypeptides and calmodulin-binding peptides. For example, a jGCaMP8 polypeptide can have a sequence that includes SEQ ID NO:1, SEQ ID NO:3, SEQ ID NO:5, SEQ ID NO: 7, SEQ ID NO:9, SEQ ID NO:11, SEQ ID NO: 13, SEQ ID NO:15, SEQ ID NO:17, SEQ ID NO:19, or SEQ ID NO:21, and a calmodulin-binding peptide can have a sequence that includes SEQ ID NOs: 25-55 or residues 10-29 of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21, and can optionally include one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, or any of SEQ ID NOs: 25-55 is expressed as a percentage of the total number of amino acids present. For example, about 0.5%, 1.0%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, or 30% (or a range between any of the aforementioned numbers) of the amino acids present in SEQ ID NO:1, SEQ ID NO:3, SEQ ID NO:5, SEQ ID NO:7, SEQ ID NO:9, SEQ ID NO: 11, SEQ ID NO:13, SEQ ID NO:15, SEQ ID NO: 17, SEQ ID NO:19, SEQ ID NO:21, or any of SEQ ID NOs: 25-55 can be substituted with a conservative amino acid(s), so long as the desired function of the peptide is maintained (e.g., substantially maintained)). In addition to a substitution, an insertion or a deletion can be introduced into a jGCaMP8 polypeptide. Insertions include the introduction of single or multiple amino acid residues, while deletions are characterized by the removal of one or more amino acid residues. Methods for predicting tolerance to protein modification are known in the art (see, e.g., Guo et al., 2004, PNAS USA, 101(25):9205-9210).

Nucleic acids that encode the polypeptide sequences, variants, and fragments thereof are disclosed. These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every nucleic acid sequence is in fact disclosed and described herein through the disclosed polypeptide sequences.

A GECI polypeptide, a calmodulin-binding peptide therefrom, or a nucleic acid encoding such a GECI polypeptide, all provided herein, can have at least 70% sequence identity (e.g., at least 71%, 72%, 73%, or 74% sequence identity), at least 75% sequence identity (e.g., at least 76%, 77%, 78%, or 79% sequence identity), at least 80% sequence identity (e.g., at least 81%, 82%, 83%, or 84% sequence identity), at least 85% sequence identity (e.g., at least 86%, 87%, 88%, or 89% sequence identity), at least 90% sequence identity (e.g., at least 91%, 92%, 93%, or 94% sequence identity), at least 95% sequence identity (e.g., at least 96%, 97%, 98%, or 99% sequence identity) to a GECI polypeptide disclosed herein (e.g., SEQ ID NO:1, SEQ ID NO:3, SEQ ID NO:5, SEQ ID NO:7, SEQ ID NO:9, SEQ ID NO: 11, SEQ ID NO: 13, SEQ ID NO:15, SEQ ID NO: 17, SEQ ID NO: 19, or SEQ ID NO:21), to a nucleic acid molecule disclosed herein that encodes for a GECI polypeptide (e.g., SEQ ID NO:2, SEQ ID NO:4, SEQ ID NO:6, SEQ ID NO:8, SEQ ID NO:10, SEQ ID NO: 12, SEQ ID NO:14, SEQ ID NO:16, SEQ ID NO: 18, SEQ ID NO:20, or SEQ ID NO:22), or to a calmodulin-binding peptide disclosed herein (e.g., SEQ ID NOs: 25-55 or residues 10-29 of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21).

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence disclosed herein (e.g., any of SEQ ID NOs: 1-22 and 25-55) and another sequence, the default parameters of the respective programs are used.

TABLE 1

Representative Conservative Amino Acid Substitutions

| Amino Acid | Representative Conservative Amino Acids |
| --- | --- |
| Ala | Ser, Gly, Cys |
| Arg | Lys, Gin, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

Modifications, including substitutions, insertions or deletions are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

As described above, the jGCaMP8 variants provided herein have the same or better characteristics than jGCaMP7 (see, for example, US 2019/0153967). For example, the jGCaMP8 variants have one or more of the following characteristics: a 2- to 3.5-fold reduction in half-rise time, a 1.2- to 3.7-fold reduction in peak time, a 1.75- to 5.2 increase in ΔF/F0, and a 1.7- to 8-fold increase in signal-to-noise ratio (SNR) in response to 1AP stimulation compared to jGCaMP7f (Table 2). Overall, the jGCaMP8 group of sensors is optimized for detecting single action potentials with fast kinetics and high sensitivity. The fast kinetics are necessary for detecting action potentials of fast-spiking neurons. Individual constructs are further optimized for different applications requiring exceptionally fast kinetics (jGCaMP8f), high sensitivity (e.g. jGCaMP8s), high dynamic range of the response (e.g. jGCaMP8.712), or high baseline fluorescence (e.g. jGCaMP8.707). The jGCaMP8 variants described herein can be compared to GCaMP5, GCaMP6, and/or jGCaMP7 using the methods described herein.

Also provided are vectors that include the GECI-encoding nucleic acid sequences disclosed herein or nucleic acid sequences encoding the calmodulin-binding peptides disclosed herein (e.g., any of SEQ ID NOs: 25-55 or residues 10-29 of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21). The GECI-encoding nucleic acid sequences can include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, or SEQ ID NO:22, or sequences with identity thereto, as noted above. Similarly, the GECI polypeptide can include SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO:17, SEQ ID NO:19, SEQ ID NO:21, or sequences with identity thereto, as noted above. Examples of suitable vectors include, but are not limited to, plasmids, artificial chromosomes such as BACs, YACs, or PACs, and any of a number of viral vectors (e.g., retroviral vectors, replication-defective adenoviruses).

Vectors typically contain an origin of replication and one or more regulatory regions. Regulatory regions include, without limitation, promoters, enhancers, inducible elements, protein binding sequences, 5' or 3' untranslated regions (UTRs), transcriptional start sites, termination sequences, and polyadenylation sequences.

Promoters may be obtained from various sources including, for example, viruses such as polyoma, Simian Virus 40 (SV40), adenovirus, retroviruses, hepatitis B virus, and cytomegalovirus (CMV), or promoters from mammalian cells, e.g. beta-actin promoter or EF1-alpha promoter. In addition, promoters native to the host cell also are useful herein.

Enhancers refer generally to nucleic acid sequences that affect transcription of a sequence. Enhancers typically are able to act at a distance from the transcribed sequence, be 5' or 3' to, or within an intron of, the transcribed sequence, and/or can be in cis orientation to the transcribed sequence. Many enhancer sequences are known from mammalian genes (globin, elastase, albumin, fetoprotein, and insulin), as well as from viruses (e.g., the SV40 enhancer on the late side of the replication origin, the cytomegalovirus early promoter enhancer, the polyoma enhancer on the late side of the replication origin, and adenovirus enhancers).

A promoter and/or an enhancer can be inducible (e.g. chemically or physically regulated). A chemically-induced promoter and/or enhancer can be regulated by the presence of, for example, alcohol, tetracycline, a steroid, or a metal. A physically-induced promoter and/or enhancer can be regulated by, for example, environmental factors such as temperature or light. On the other hand, a promoter and/or enhancer can be constitutive. In addition, certain promoters and/or enhancers can be active in a cell type-specific manner.

Vectors also can include a selectable marker. A selectable marker typically confers a phenotype on a cell and allows the cell to survive when placed under selective pressure. The product of the selectable marker can be used to confirm that the vector has been delivered to the cell and is being expressed. Examples of selectable markers include, without limitation, dihydrofolate reductase (DHFR), thymidine kinase, neomycin, neomycin analog G418, hygromycin, puromycin, blasticidin, beta-galactosidase, beta-glucuronidase, green fluorescent protein (GFP), and luciferase.

In addition, a vector can include a sequence encoding a tag, which is designed to facilitate manipulation or detection (e.g., purification or localization) of the expressed polypeptide. Sequences encoding tags such as GFP, glutathione S-transferase (GST), poly-histidine, c-myc, hemagglutinin, or FLAG™ tag (Kodak; New Haven, CT) typically are expressed as a fusion with the encoded polypeptide (e.g., at either the carboxyl or amino terminus or within the polypeptide).

Cells comprising the GECIs, the GECI-encoding nucleic acid sequences or vectors comprising the GECI-encoding nucleic acid sequence are provided. The cell can be, for example, a eukaryotic or prokaryotic cell. Suitable cells include, but are not limited to cells of *E. coli*, *Pseudomonas*, *Bacillus*, *Streptomyces*; fungal cells such as yeasts (*Saccharomyces*, and methylotrophic yeast such as *Pichia*, *Candida*, *Hansenula*, and *Torulopsis*); and animal cells, such as CHO, RI.1, B—W and LM cells, African Green Monkey kidney cells (for example, COS 1, COS 7, BSC1, BSC40, and BMT10), and insect cells (for example, Sf9). Suitable cells also include, but are not limited to, human cells and plant cells. Representative human cells include, for example, HeLa cells or human embryonic kidney (HEK) cells. Cells that can be used herein are commercially available from, for example, the American Type Culture Collection (ATCC; PO Box 1549, Manassas, VA 20108). See also Ausubel et al., 1998, Current Protocols in Molecular Biology, John Wiley & Sons, New York, NY. In some instances, the GECI-encoding nucleic acid sequence can be located in the genome of the cell. In some embodiments, the cell also includes a nucleic acid encoding a G-protein coupled receptor (GPCR) or an ion channel. Such a nucleic acid encoding a GPCR or an ion channel can be heterologous or endogenous to the cell.

Methods of introducing nucleic acids into cells are known and the method of transformation and choice of expression vector will depend on the host system selected. Transformation and transfection methods are described, e.g., in Ausubel et al. (1998, Current Protocols in Molecular Biology, John Wiley & Sons, New York, NY, (1998)), and, as described above, expression vectors may be chosen from examples known in the art. There are a number of compositions and methods that can be used to deliver the nucleic acid molecules and subsequently encoded polypeptides to cells, either in vitro or in vivo. These methods and compositions can largely be broken down into two classes: viral-based delivery systems and non-viral-based delivery systems. Such delivery systems are well known in the art and are readily adaptable for use with the compositions and methods described herein.

Simply by way of example, polypeptides and/or nucleic acid molecules can be delivered via virus-like particles. Virus-like particles (VLPs) consist of viral protein(s) derived from the structural proteins of a virus. Methods for making and using virus-like particles are described in, for example, Garcea and Gissmann (2004, Current Opinion in Biotechnology, 15:513-7). Polypeptides also can be delivered by subviral dense bodies (DBs). DBs transport proteins into target cells by membrane fusion. Methods for making and using DBs are described in, for example, Pepperl-Klindworth et al. (2003, Gene Therapy, 10:278-84). In addition, polypeptides can be delivered by tegument aggregates. Methods for making and using tegument aggregates are described in WO 2006/110728.

Also provided are transgenic animals that include a GECI-encoding nucleic acid sequences described herein. "Animal" refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal in which one or more of the cells of the animal contain a heterologous nucleic acid. Methods for making transgenic animals have been described, for example, in Wagner et al. (1981, PNAS USA, 78:5016-5020); Stewart et al. (1982, Science, 217:1046-1048); Constantini et al. (1981, Nature, 294:92-94); Lacy et al. (1983, Cell, 34:343-358); McKnight et al. (1983, Cell, 34:335-341); Brinstar et al. (1983, Nature, 306:332-336); Palmiter et al. (1982, Nature, 300:611-615); Palmiter et al. (1982, Cell, 29:701-710); and Palmiter et al. (1983, Science, 222:809-814). Methods for making transgenic animals also are described in U.S. Pat. Nos. 6,175,057; 6,180,849; and 6,133,502.

One or more of the nucleic acid sequences, polypeptides, vectors or cells described herein, or combinations thereof, can be packaged into an article of manufacture (i.e., a kit) using containers, vials, or the like. For example, an article of manufacture can include (i) a nucleic acid sequence encoding a GECI, where the GECI has a sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, or SEQ ID NO:21, or a variant of those sequences as discussed above; (ii) a GECI polypeptide having a sequence shown in SEQ ID NO:1, SEQ ID NO:3, SEQ ID NO:5, SEQ ID NO:7, SEQ ID NO:9, SEQ ID NO: 11, SEQ ID NO: 13, SEQ ID NO:15, SEQ ID NO: 17, SEQ ID NO: 19, or SEQ ID NO:21, or a variant of those sequences as discussed above; (iii) a calmodulin-binding peptide having any of the sequences shown in SEQ ID NOs: 25-55 or residues 10-29 of any of SEQ ID NO:1, SEQ ID NO:3, SEQ ID NO:5, SEQ ID NO:7, SEQ ID NO:9, SEQ ID NO: 11, SEQ ID NO:13, SEQ ID NO:15, SEQ ID NO:17, SEQ ID NO:19, or SEQ ID NO:21; (iv) a vector comprising (i); (v) a cell comprising (i); (vi) a cell comprising (ii); (vii) a cell comprising (iii); (viii) a cell comprising (iv); (ix) a transgenic animal comprising any of (i)-(viii). An article of manufacture as described herein can include any combination of (i)-(ix).

In addition, an article of manufacture as described herein can include one or more reagents, buffers, culture medium, neuronal or other type of cell, a G-protein coupled receptor (GPCR) polypeptide or a nucleic acid encoding a GPCR polypeptide, or an ion channel polypeptide or a nucleic acid encoding an ion channel polypeptide. An article of manufacture also can include instructions for use.

Methods of Using the Nucleic Acid and Polypeptide Compositions

The nucleic acid and polypeptide compositions described above, including, for example, vectors and cells containing such vectors, can be used in methods of screening for G-protein coupled receptor (GPCR) or ion channel agonists and antagonists. For example, a cell that expresses both a GPCR and one of the genetically encoded calcium indicators (GECI) described herein (e.g., a nucleic acid having the sequence shown in SEQ ID NO:2, SEQ ID NO:4, or SEQ ID NO:6, SEQ ID NO:8, SEQ ID NO:10, SEQ ID NO:12, SEQ ID NO:14, SEQ ID NO:16, SEQ ID NO:18, SEQ ID NO:20, or SEQ ID NO:22 encoding a polypeptide having the sequence shown in SEQ ID NO:1, SEQ ID NO:3, or SEQ ID NO:5, SEQ ID NO:7, SEQ ID NO:9, SEQ ID NO:11, SEQ ID NO: 13, SEQ ID NO: 15, SEQ ID NO:17, SEQ ID NO:19, or SEQ ID NO:21 respectively) or a cell that expresses both an ion channel and one of the GECIs described herein can be contacted with an agent to be tested, and the level of fluorescence determined.

Generally, using the methods described herein, an increase in fluorescence indicates that the agent is a GPCR or ion channel agonist, while a decrease in fluorescence indicates that the agent is a GPCR or ion channel antagonist. As indicated herein, the GPCR or ion channel can be endogenous to the cell, or can be heterologous to the cell. If the GPCR or ion channel is heterologous to the cell, the nucleic acid encoding the GPCR or ion channel can be on the same or a different vector from the nucleic acid encoding the GECI or ion channel. Fluorescence is routinely determined in laboratories, and the level of fluorescence can be determined using any type of fluorometer.

Those skilled in the art understand that a determination of an increase or a decrease in fluorescence in the presence of an agent requires the use of an appropriate control. By way of example, one appropriate control can be measuring the level of fluorescence in a cell before and/or after a treatment (i.e., contact with an agent); another appropriate control can be measuring the level of fluorescence in the absence of a treatment (i.e., contact with an agent).

As used herein, an agent that can be screened in the methods described herein includes, for example, a polypeptide, an antibody (e.g., polyclonal or monoclonal; human or humanized) a small molecule, a nucleic acid molecule, a peptidomimetic, or any combination thereof. Nucleic acid molecules used in a method of screening as described herein can be, for example, an inhibitory nucleic acid molecule. Inhibitory nucleic acid molecules include, for example, a triplex forming oligonucleotide, an aptamer, a ribozyme, a short interfering RNA (siRNA), a micro-RNA (miRNA), or antisense nucleic acid. These types of inhibitory nucleic acid molecules are well known in the art and methods of designing them and making them also are well known in the art.

As is understood in the art, a G-protein coupled receptor (GPCR) refers to any member of a superfamily of receptors that mediates signal transduction by coupling with a G protein and is associated with a change in Ca2+ signaling and/or concentration. This class of GPCRs acts through the Gq type of G proteins, which activate a phospholipase C (PLC) pathway, resulting in the hydrolysis of phosphoinositides to generate two classes of different second messengers, diacylglycerol and inositol phosphates. Diacylglycerol activates certain protein kinase Cs (PKCs) and certain inositol phosphates stimulate the mobilization of calcium from intracellular stores.

Exemplary GPCRs include, but are not limited to alpha-1 adrenergic receptors (a1-AR), urotensin (UT) receptors, 5-HT2 and 5-HT6 serotonin receptors, hypocretin (orexin) receptors, histamine H1 receptors, bradykinin B1 and B2 receptors, bombesin BB2 receptors, P2Y purinergic receptors, acetylcholine receptors (e.g., M1, M3 and M5), mGluR5 glutamate receptors, vasopressin V2 and V1 receptors, angiotensin AGTRI receptors, cholecystokinin CCKAR and CCKBR receptors, endothelin ENDRA receptors, ghrelin GHSRla receptors, melatonin MTNRIA receptors, neurotensin NTSR1 receptors, platelet-activating factor PTAFR receptors, and prolactin releasing peptide receptor PRLHR receptors.

It is also possible to study Gs- and Gi-coupled receptors by co-expressing a cAMP-gated Ca2+ channel (Airan et al., 2009, Nature, 458(7241): 1025-1029). This is carried out by taking advantage of the promiscuous G-protein G15/16 (Zhang et al., 2003, J Biomol Screen, 8(5):571-577), or by using chimeric G-proteins (Hsu and Luo, 2007, Am J Physiol Endocrinol Metab., 293(4):E1021-E1029). Such receptors include, but are not limited to, G-coupled 5-HT6 and 5-HT7 serotonin receptors, Gi-coupled GABA-B, histamine H3, and mGluR2/4 glutamate receptors.

As is understood in the art, an ion channel refers to any member of a superfamily of proteins that mediate cation or anion conductance into a cell, either through molecule binding (ligand-gated ion channels), membrane depolarization (voltage-gated ion channels), temperature stimulus (temperature-gated ion channels), force stimulus (force-gated ion channels), light stimulus (light-gated ion channels), pressure stimulus (pressure-gated ion channels), or other stimuli. Suitable ion channels for use with the GECIs described herein typically are calcium ion channels.

Exemplary ligand-gated calcium channels include, but are not limited to, AMPA (a-amino-3-hydroxy-5-methyl-4-isoxazolepropionic acid) receptors including iGluR1, iGluR2, iGluR3, iGluR4; NMDA (N-methyl-D-aspartate) receptors including NR1 and NR2; kainate receptors including iGluR5, iGluR6, iGluR7, KA1, and KA2; nicotinic acetylcholine receptors including alpha9, alpha10, alpha7, alpha8, alpha2, alpha3, alpha4, alpha6, beta2, beta4, beta3, alpha5, alpha1, beta1, gamma, delta, or epsilon nicotinic acetylcholine receptor subunits; P2X receptors; P2Y receptors; IP3 receptors; ryanodine receptors; two-pore calcium channels; and sperm cation channels. Representative voltage-gated calcium channels include, but are not limited to, L-type, N-type, P/Q-type, and R-type voltage-gated calcium channels such as CaV1.1, CaV1.2, CaV1.3, CaV1.4, CaV2.1, CaV2.2, CaV2.3, CaV3.1, CaV3.2, and CaV3.3. Exemplary temperature-gated calcium channels include, without limitation, transient receptor potential (TRP) channels including TRPC, TRPV, TRPA, TRPM, TRPP, TRPML, and TRPN channels. Representative light-gated calcium channels include channelrhodopsin-2 (ChR2) and mutants thereof. Some of these calcium ion channels, such as the TRP channels, respond to other stimuli such as force and/or pressure.

The nucleic acid and polypeptide compositions described above, including, for example, expression vectors and cells containing such expression vectors, can be used in methods of determining the calcium ion status of a cell. In addition, the nucleic acid and polypeptide compositions described above can be used in methods of monitoring neuronal activity. As discussed in more detail below, neuronal activity can be monitored in neuronal cells that are expressing a nucleic acid construct encoding a calmodulin-binding peptide as described herein (e.g., a nucleic acid encoding any of SEQ ID NOs: 25-55 or residues 10-29 of any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, or SEQ ID NO:21) or a nucleic acid encoding a GECI polypeptide as described herein (e.g., a nucleic acid encoding a polypeptide having the sequence shown in SEQ ID NO:1, SEQ ID NO:3, or SEQ ID NO:5, SEQ ID NO:7, SEQ ID NO:9, SEQ ID NO:11, SEQ ID NO: 13, SEQ ID NO:15, SEQ ID NO:17, SEQ ID NO:19, or SEQ ID NO:21), and detecting the fluorescence emitted by the cells. Neuronal activity can be natural (e.g. neurons in the brain of an animal that is behaving, or a brain slice exhibiting spontaneous activity), or can be elicited by a chemical stimulus, an electrical stimulus, or another type of stimulus. A chemical stimulus can include a drug or combination of drugs, a toxin, a neurotransmitter, or any other compound. An electrical stimulus can be delivered, for example, from an extracellular electrode, or from an intracellular electrode, a magnetic resonance imaging (MRI) device, or any other type of electrical stimulus.

The neuronal cells can be contacted with the stimulus in vitro (e.g., in cell culture) or in vivo (e.g., in an animal such as, without limitation, a mouse, a worm, a rat, or a fly). Neuronal activity is used herein as an example, but those skilled in the art would understand that the activity of other cells types can be examined. For example, the activity of muscle cells, cardiomyocytes, or astrocytes and other glial cells can be evaluated using the compositions and methods described herein. Other cell types that can evaluated using the compositions and methods described herein include bacteria, single-cell pathogens, or cells in nematodes, insects, arachnids, and other animals.

The jGCaMP8 sensors described herein can be use, for example, in the following in vivo applications:

Imaging jGCaMP8 sensors expressed in neurons in mouse brain in vivo and recording neuronal response to sensory stimuli or behavioral perturbations Imaging jGCaMP8 sensors expressed in neurons in vivo while simultaneously performing cell-attached recordings Using jGCaMP8 to improve the ability to discriminate single action potentials in vivo. The fast kinetics and high SNR of the sensor make it possible to dramatically improve spike deconvolution Using jGCaMP8 sensors to recover single action potential activity from fast-spiking interneurons in vivo Imaging jGCaMP8 sensors expressed in neurons of *Drosophila* larva neuromuscular junction Imaging jGCaMP8 sensors expressed in L2 neurons of adult *Drosophila* to record the response of neurons to high-frequency light pulses which was not possible before due to the slow kinetics of other sensors Imaging jGCaMP8 sensors expressed in L2 neurons of adult *Drosophila* to identify the response of neurons to odors Imaging jGCaMP8 sensors expressed in zebrafish Imaging jGCaMP8 sensors expressed in *C. elegans*

Imaging jGCaMP8 activityin axons, dendrites, spins, and terminals

Functional screening of action potentials in iPSC-derived cardiomyocytes and neurons in response to application of small molecule or biological drug candidates Detecting seizure-like neuronal activity (high-frequency firing) in cultured cells, brain organoids, or in vivo, and helping in developing drugs and treatments Screening for drugs that modify interneuron activity Probing Ca2+ dynamics in immune cells such as T cells during viral infection to screen for viral entry blockers In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1-Mutagenesis

Culture Screening Results 767 variants of GCaMP were screened in a cultured neuron screen as previously described (Chen et al. (2013, Nature, 499:295-300); Dana et al. (2019, Nat. Methods, 16:649-657); Wardill et al. (2013, PLOS ONE, 8:e77728)). In addition to the variants being tested, every screening plate contained known controls: GCaMP6s, GCaMP6f, and jGCaMP7f. The best-performing variants were additionally compared to the rest of the jGCaMP7 sensor family (jGCaMP7s/f/c/b), as well as the green XCaMP sensors (XCaMP-G, XCaMP-Gf, XCaMP-Gf0) (Inoue et al. 2019, Cell, 177:1346-60).

Figure 1:
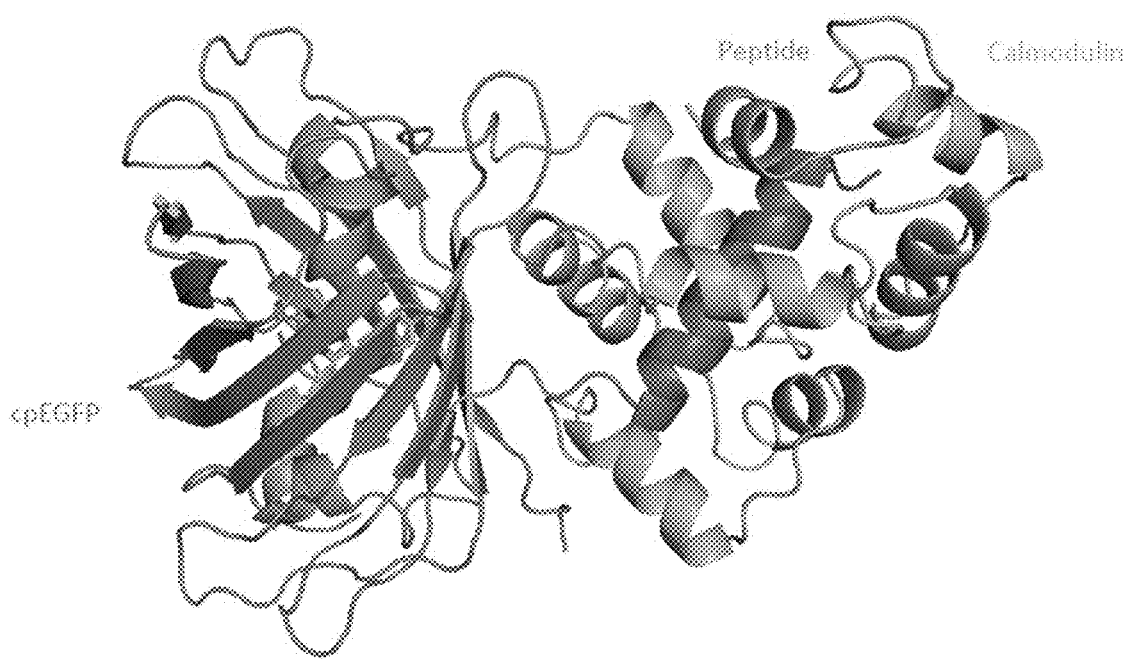
Figure 2:
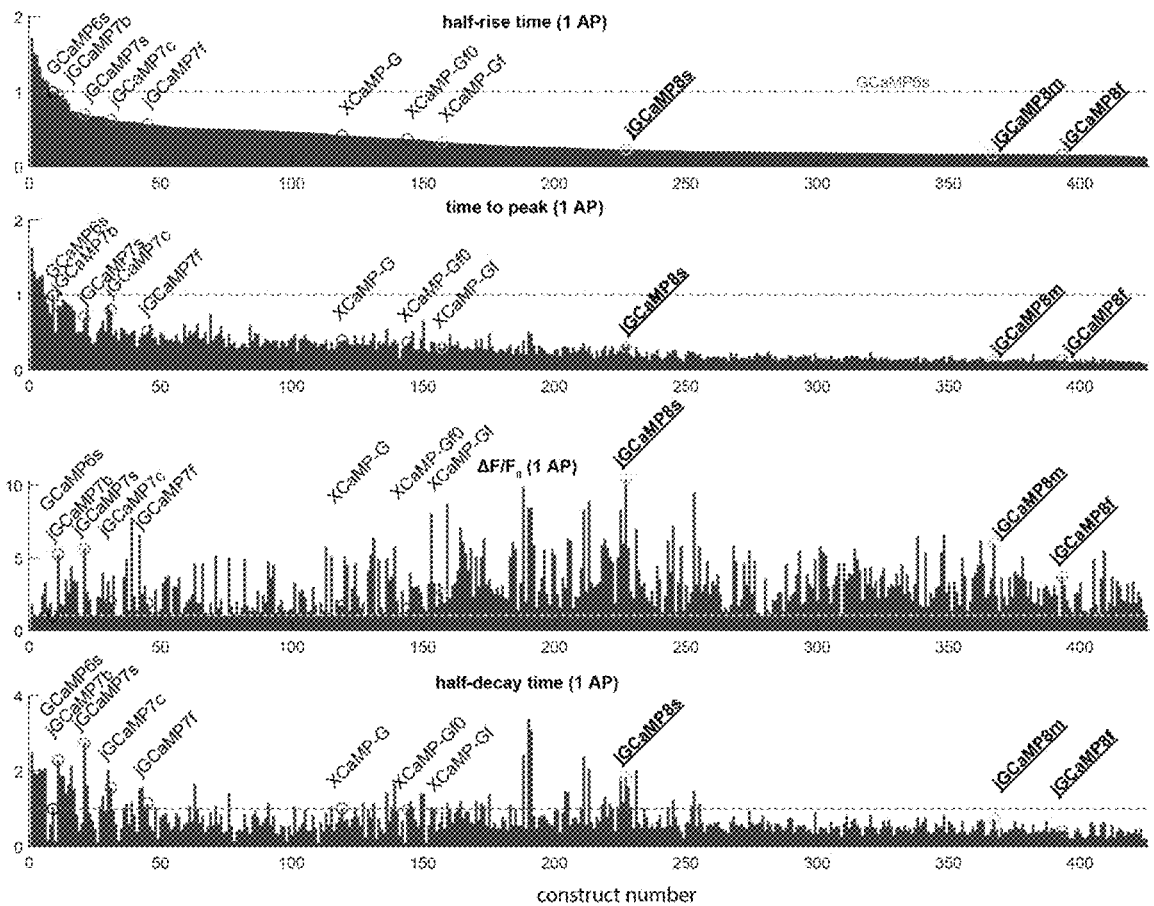
Figure 3A:
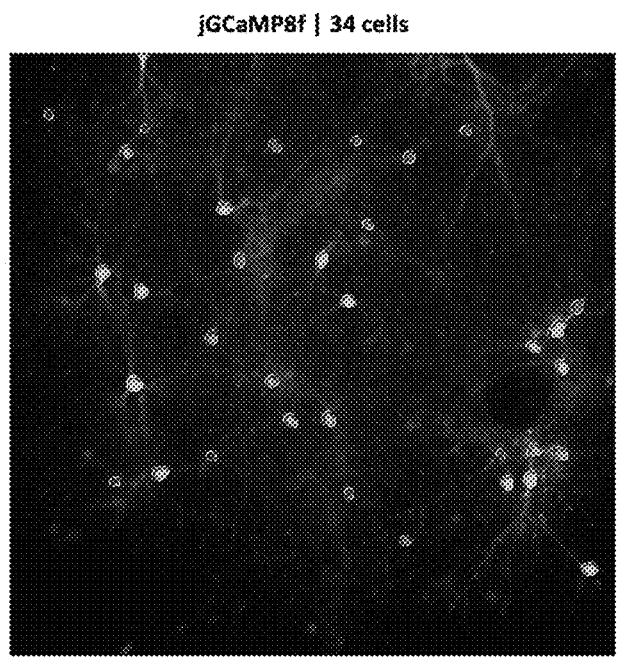
Figure 3B:
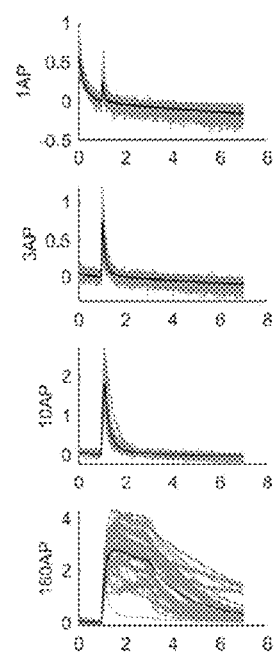
Figure 3C:
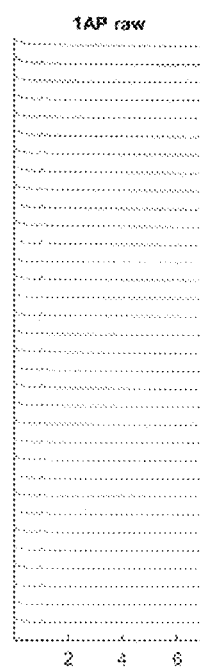
Figure 4A:
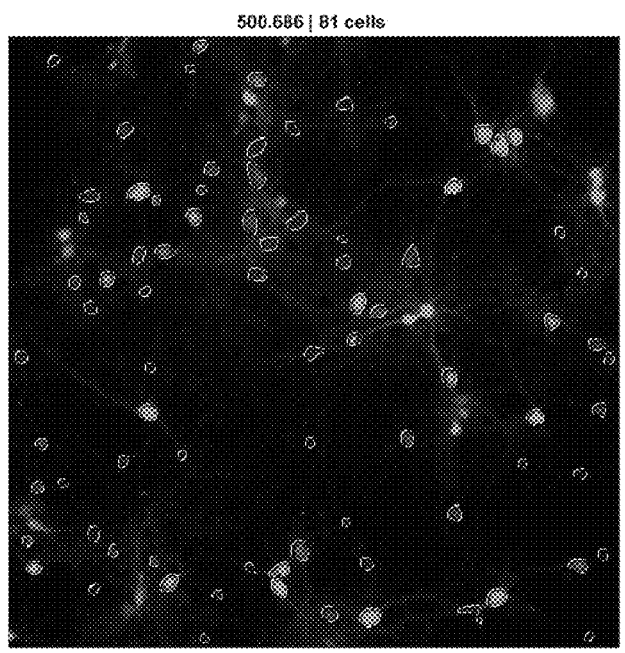
Figure 4B:
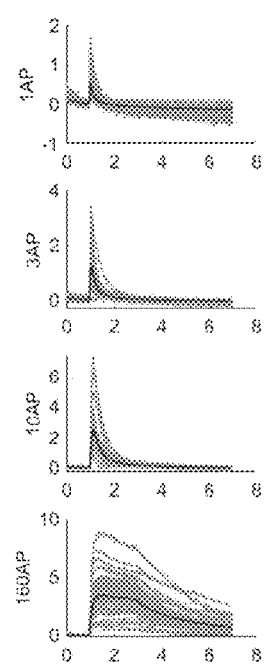
Figure 4C:
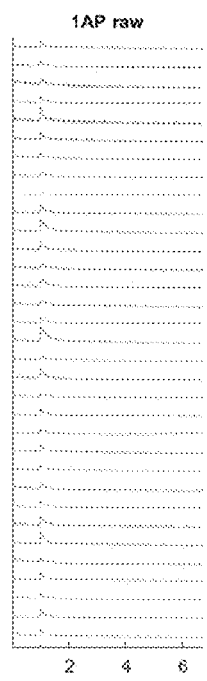
Figure 5A:
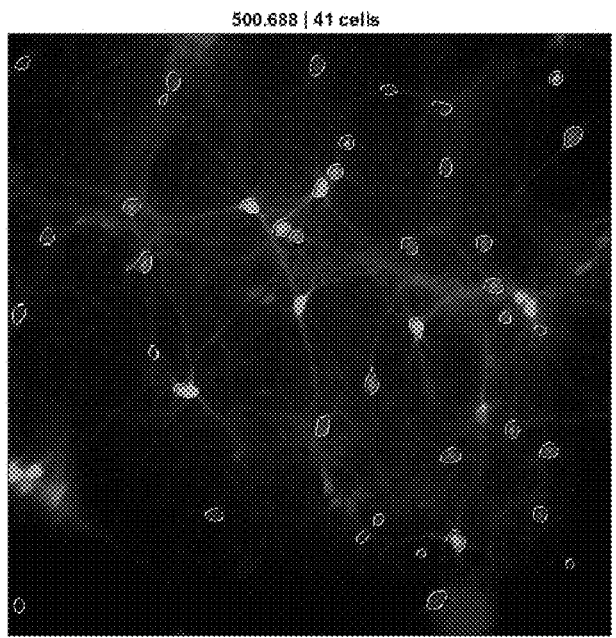
Figure 5B:
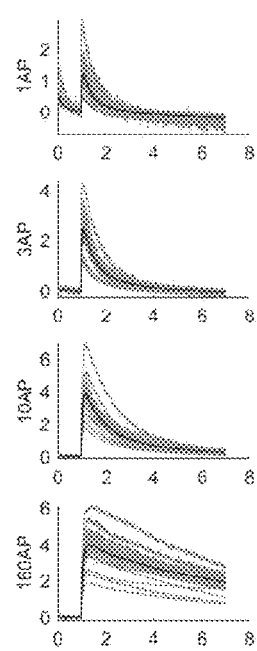
Figure 5C:
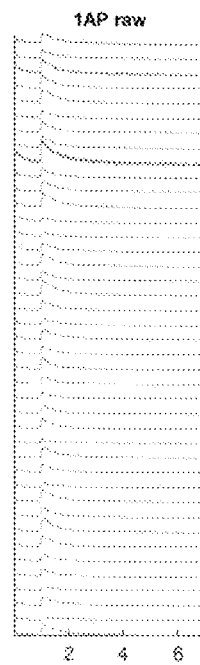
Figure 6A:
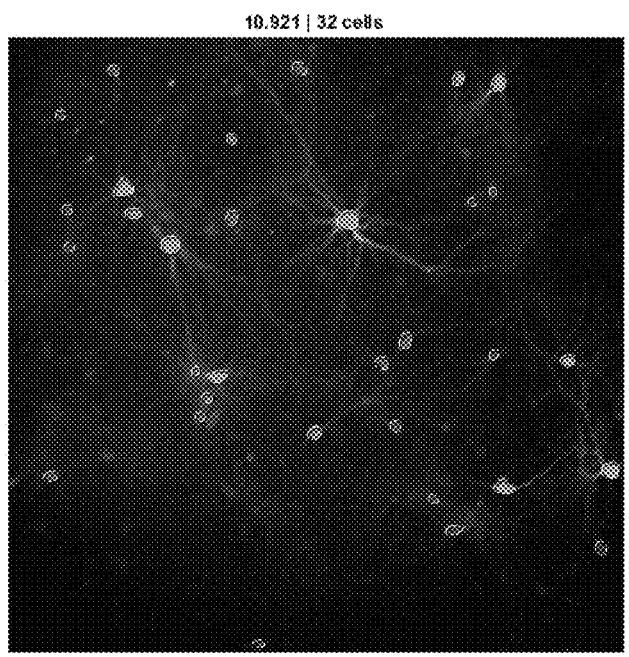
Figure 6B:
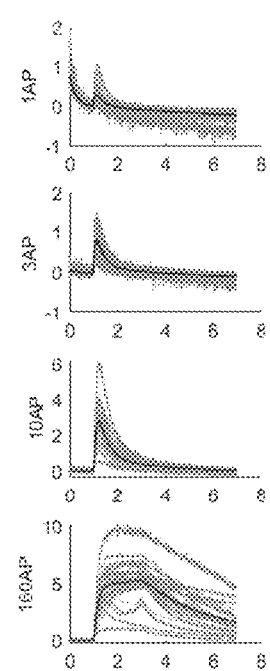
Figure 6C:
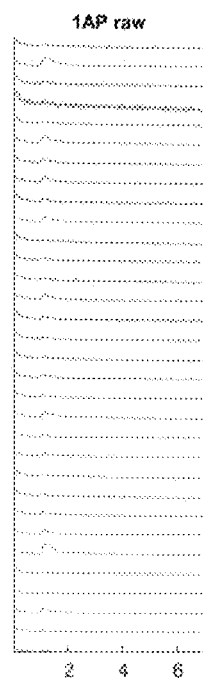

Of all the screened variants, those with peak $\Delta F/F0$ for 1 AP stimulation less than that of GCaMP6s ($\Delta F/F0=0.12$) were eliminated. The remaining 450 variants were sorted according to 1 AP half-rise time to find variants with the fastest onset kinetics (FIG. 2). Three variants with favorable combinations of on and off kinetics as well as high $\Delta F/F0$ for 1 AP were identified. These variants were named jGCaMP8f (Janelia GCaMP 8 fast), jGCaMP8s (sensitive), and jGCaMP8m (medium), and the sequences of each are shown below. Representative raw results from single wells for these new sensors as well as the jGCaMP7f control are shown in FIGS. 3-6.

Figures 7A, 7B, 7C, 7D, 7E, 7F:
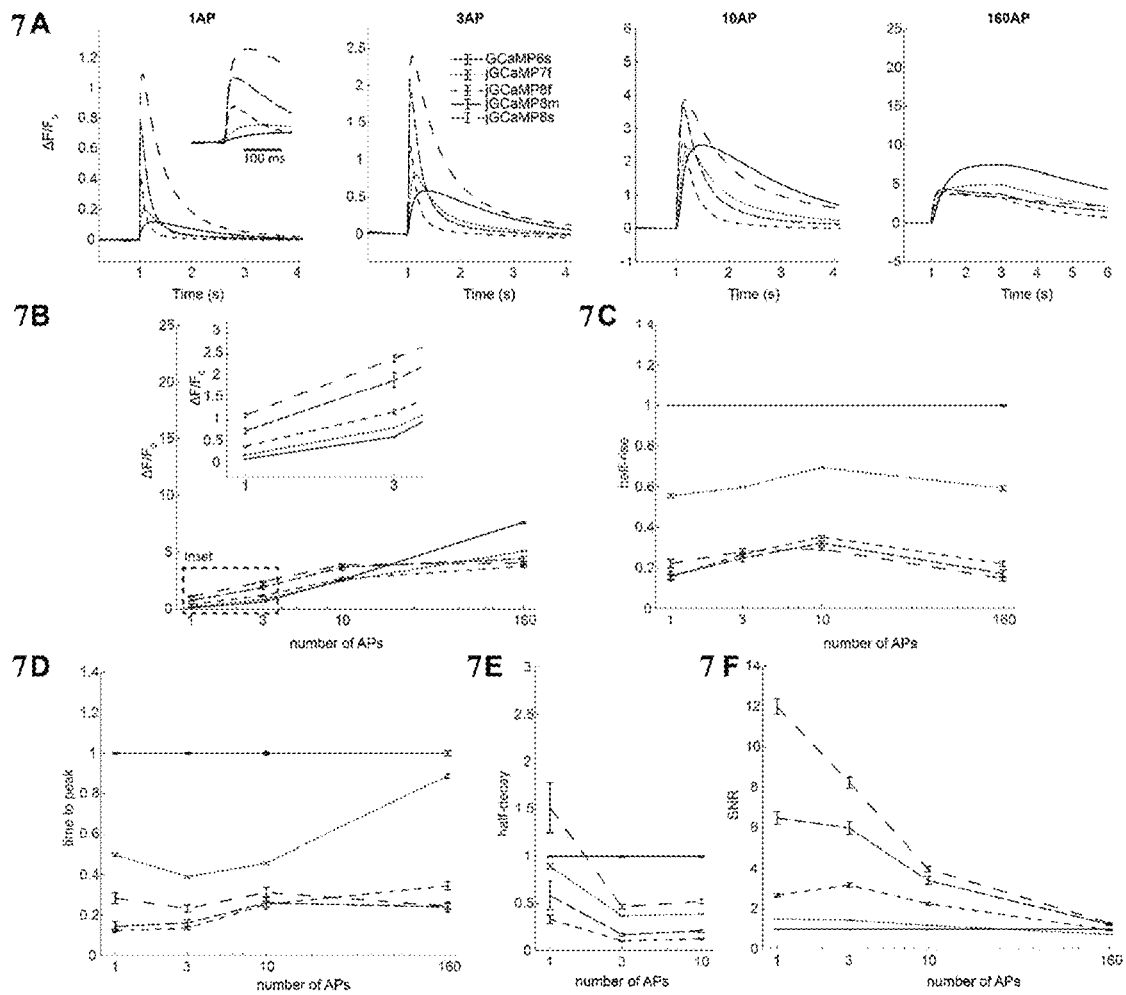
Figure 8:
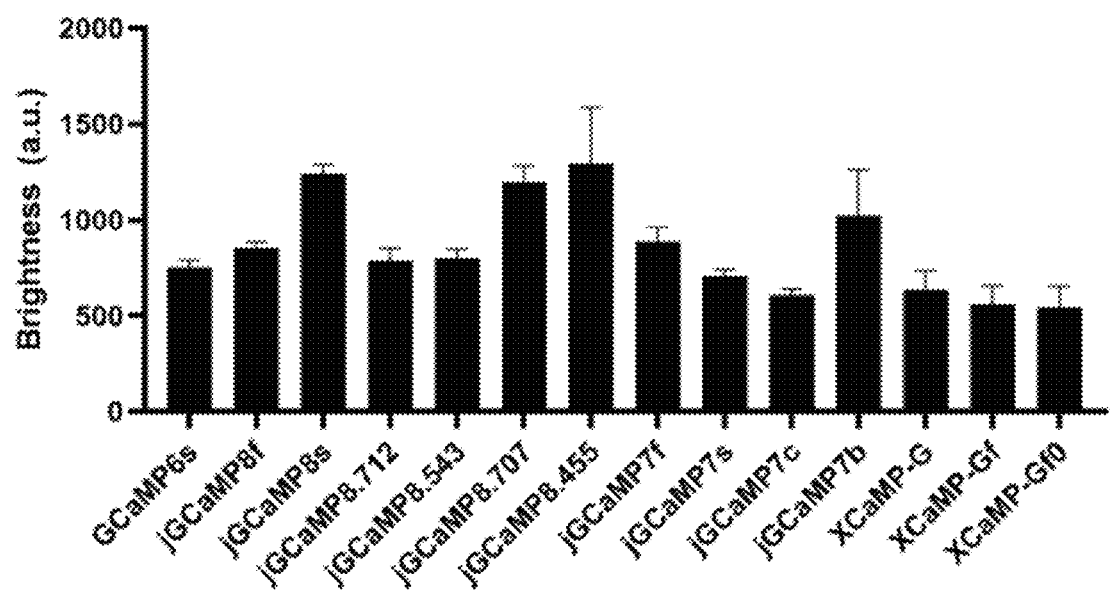

Average traces of the jGCaMP8 series of GECIs confirm that the 1 AP kinetics and sensitivity of these sensors are considerably improved over previous variants, including GCaMP6s and jGCaMP7f (FIG. 7A, Table 2). To minimize batch-to-batch variability in cell culture, variant responses were normalized to mean GCaMP6s responses from the same batch of neurons (FIG. 7B-7F). In a separate batch of cultured neurons, the resting fluorescence (F0) of jGCaMP8f and jGCaMP8s were evaluated and compared to GCaMP6s, the jGCaMP7 series, and the green XCaMP sensors (FIG. 8).

TABLE 2

1-AP sensitivity and kinetics parameters for jGCaMP8 series of sensors and controls (GCaMP6s, jGCaMP7f)

| construct | $\Delta F/F_0$ | half-rise time (ms) | time to peak (ms) | half-decay time (ms) | SNR |
| --- | --- | --- | --- | --- | --- |
| GCaMP6s (control) | 0.12 ± 0.70 | 45.3 ± 20.6 | 201 ± 80.6 | 203.4 ± 175 | 4.1 ± 3.8 |
| jGCaMP7f (control) | 0.21 ± 0.10 | 24.8 ± 6.6 | 99.5 ± 30.2 | 181.9 ± 76 | 6.2 ± 5.5 |
| jGCaMP8f (fast) | 0.41 ± 0.12 | 7.1 ± 0.7 | 24.8 ± 6.1 | 67.4 ± 11.2 | 11.0 ± 9.4 |
| jGCaMP8m (medium) | 0.76 ± 0.22 | 7.3 ± 0.6 | 29.0 ± 11.2 | 118.3 ± 13.2 | 26.6 ± 12.8 |
| jGCaMP8s (sensitive) | 1.11 ± 0.2 | 10.1 ± 0.9 | 57.0 ± 12.9 | 306.7 ± 32.2 | 49.4 ± 27.5 |
| jGCaMP8.333 (parent construct) | 0.38 ± 0.12 | 7.5 ± 1.1 | 27 ± 7.2 | 81 ± 17.4 | 10.9 ± 9.1 |
| jGCaMP8.640 (sensitive) | 0.56 ± 0.13 | 13.5 ± 1.9 | 81.1 ± 21.3 | 202 ± 34 | 22.3 ± 16.0 |
| jGCaMP8.712 (high dynamic range) | 0.66 ± 0.18 | 10.9 ± 1.2 | 41.6 ± 8.1 | 95 ± 13 | 20.3 ± 14.6 |
| jGCaMP8.543 (high dynamic range) | 0.56 ± 0.09 | 1.11 ± 0.8 | 52.6 ± 9.3 | 158 ± 25 | 19.9 ± 12.5 |
| jGCaMP8.707 (high baseline brightness) | 0.66 ± 0.07 | 7.3 ± 0.7 | 32.5 ± 7.9 | 119 ± 15 | 26.6 ± 15.5 |
| jGCaMP8.455 (high baseline brightness) | 0.56 ± 0.08 | 7.4 ± 0.9 | 32.1 ± 7.0 | 146 ± 46 | 18.9 ± 11.2 |

Data shown as mean ± standard deviation.

Figure 9:
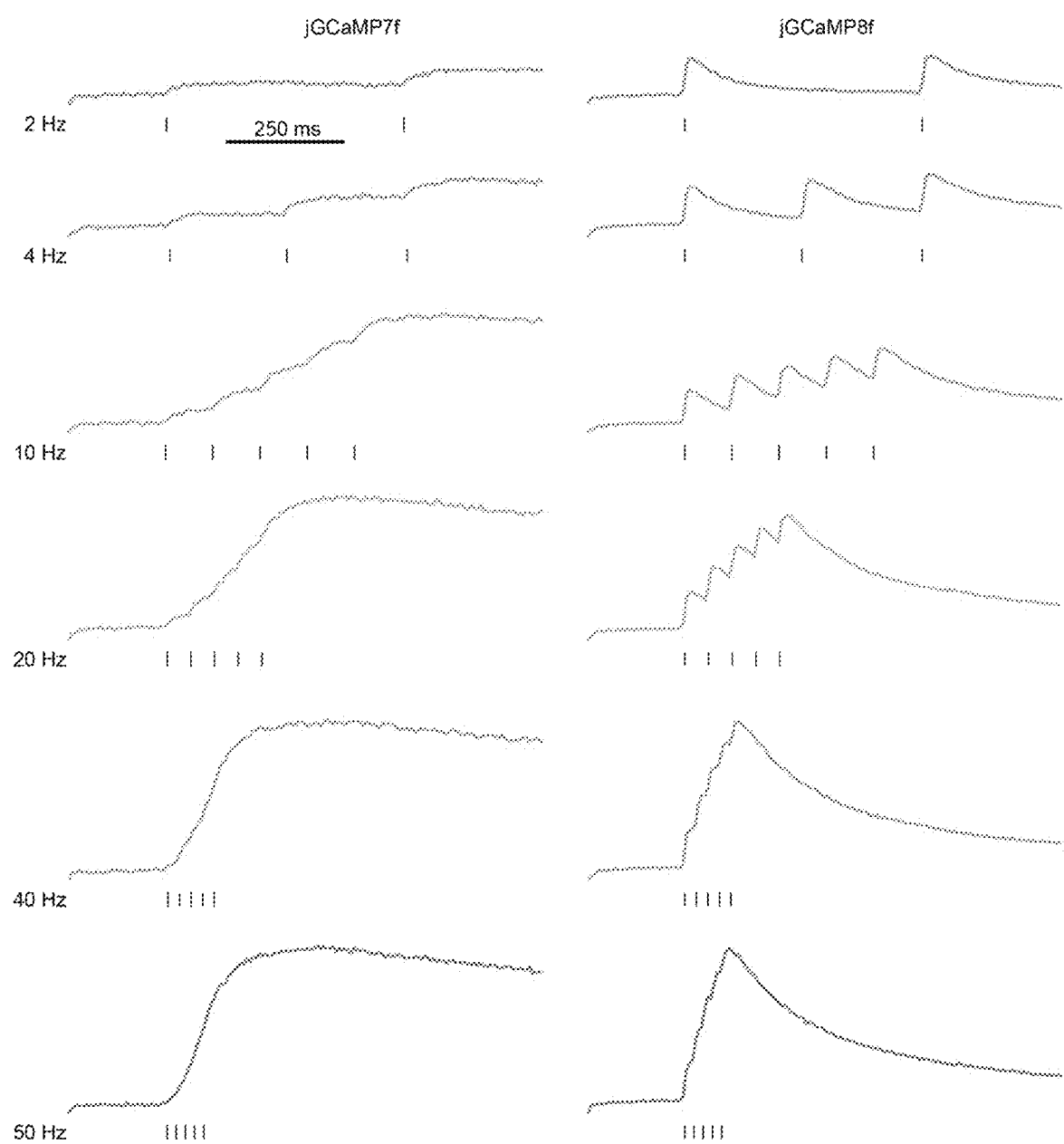
FIG. 9 are traces showing the response of jGCaMP7f and jGCaMP8f to field stimulation (2-50 Hz) under 2-photon illumination. Data from single trials in cultured neurons is shown.

A key motivation behind the development of GCaMP sensors with faster kinetics is the ability to discern action potentials firing at high frequencies. In a set of cell culture experiments, it was confirmed that jGCaMP8f can discern APs firing up to a frequency of ~40 Hz, whereas jGCaMP7f can only discern APs up to a frequency of ~4-10 Hz (FIG. 9).

Cell Culture

Experiments were conducted in accordance with guidelines for animal research approved by the Janelia Research Campus Institutional Animal Care and Use Committee. Neonatal rat pups were euthanized, and neocortices were isolated. Tissue was dissociated using papain (Worthington) in 10 mM HEPES (pH 7.4) in Hanks' Balanced Salt Solution for 30 min at 37° C. Suspensions were triturated with a Pasteur pipette and passed through a 40-μm strainer. Cells were transfected by combining 5×10^5 viable cells with 400 ng plasmid DNA and nucleofection solution in a 25-μL electroporation cuvette (Lonza). Cells were electroporated according to the manufacturer's protocol.

For the field stimulation screen, neurons were plated onto poly-D-lysine (PDL) coated, 96-well, glass bottom (#1.5 cover glass) plates (MatTek) at ~1×10^5 cells per well in 100 μL of a 1:2 mixture of NbActiv4 (BrainBits) and plating medium (28 mM glucose, 2.4 mM NaHCO3, 100 μg/mL transferrin, 25 μg/mL insulin, 2 mM L-glutamine, 100 U/mL penicillin, 10 μg/mL streptomycin, 10% FBS in MEM). The next day, 200 μL of NbActiv4 medium was added to each well. Plates were incubated at 37° C. and 5% $CO_2$, to be imaged after 14-18 days in culture.

Field Stimulation Screen

Neurons were first rinsed twice with imaging buffer (in mM: 140 NaCl, 0.2 KCl, 10 HEPES, 30 Glucose, pH 7.3-7.4) and subsequently left in a solution containing imaging buffer with added receptor blockers (10 μM CNQX, 10 μM (R)-CPP, 10 μM gabazine, 1 mM (S)-MCPG, Tocris) to increase signal fidelity and reduce spontaneous activity (Wardill et al., 2013, PLOS ONE, 8:e77728).

GCaMP fluorescence was excited with a 470 nm LED (Cairn Research) through an ET-GFP filter cube (Chroma) and imaged using a 10× 0.4 NA objective (Olympus) with an EMCCD (Ixon Ultra DU897, Andor). Images (128×128 px, 860×860 μm) were acquired at 200 Hz. During imaging, action potential (AP) trains were induced (45 V, 1 ms pulse duration, 83 Hz) using an S48 stimulator (Grass). For mCherry excitation, a 590 nm LED was used through an ET-mCherry filter cube (Chroma).

Cell somata were segmented automatically from reference images using ilastik (Berg et al. 2019). The ΔF/F0 trace of each well was calculated by taking the median ΔF/F0 of each segmented cell. The baseline fluorescence (F0) of sensors was calculated as follows: F0 of each cell in a well was calculated as the mean fluorescence of a cell in the 5 ms period before field stimulation and averaged across the four stimulation conditions. Analysis scripts were written in MATLAB and run in parallel on a high-performance computing cluster.

Example 2-Fast and Sensitive GCaMP Calcium Indicators for Imaging Neural Populations Part A-Methods All surgical and experimental procedures were conducted in accordance with protocols approved by the Institutional Animal Care and Use Committee and Institutional Biosafety Committees of Howard Hughes Medical Institute (HHMI) Janelia Research Campus, and of the corresponding committees at the other institutions.

Sensor Screen and Characterization in Solution

Cloning, expression, and purification of sensor variants in *E. coli*, calcium titrations, pH titrations, kinetic assay, and photophysical analysis were performed essentially as described before (Akerboom et al., 2012, J. Neurosci., 32(40): 13819-40).

In this study, the RSET tag (His6 tag-Xpress epitope-enterokinase cleavage site), which had been carried over from the pRSETa cloning vector in earlier work, was removed from all sensors: constructs encode Met-His6 tag-peptide-linker 1-cpGFP-linker 2-CaM. For the screen of linkers replacing RS20 (previously mistakenly referred to as "M13"), libraries of sensors in the pRSETa bacterial expression vector were generated using primers containing degenerate codons (NNS) with Q5 site-directed mutagenesis (New England BioLabs) and transformed into T7 Express competent cells (New England BioLabs). A sequence encoding six repeats of the Gly-Gly-Ser tripeptide was designed as a highly flexible, presumably non-CaM-binding negative control. We expressed the new variants, as well as the presumptive Gly-Gly-Ser negative control and GCaMP6s as a positive control, in *Escherichia coli* T7 Express. Single colonies were picked and grown in 800 μL ZYM-5052 autoinduction medium containing 100 μg/mL ampicillin in 96 deep-well blocks for 48 hours at 30° C. Cells were collected by centrifugation, frozen, thawed, and lysed. Clarified lysate was used to estimate the dynamic range by measuring fluorescence in the presence of 1 mM $Ca^{2+}$ or 1 mM EGTA.

For protein purification, T7 Express cells containing sensors were grown at 30° C. for 48 hours in ZYM-5052 autoinduction medium with 100 μg/mL ampicillin. Collected cells were lysed in 1/50 volume of B-PER (Thermo Fisher) with 1 mg/mL lysozyme and 20 U/mL Pierce Uni-

TABLE 3

Mutations of jGCaMP8 Sensors

| Construct | SEQ ID NO | Mutations (relative to jCGaMP6s_ENOSP_linker1) |
|---|---|---|
| jGCaMP8f (fast) | 1 | N19T_S24I_S26R_Q88E_Q315L |
| jGCaMP8s (sensitive) | 3 | N19T_S24I_S26M_Q88E_F286Y_Q315H |
| jGCaMP8m (medium) | 5 | N19T_S24I_A25G_S26R_Q88E_F286Y |
| jGCaMP8.333 (parent construct) | 7 | N19T_S24I_S26R_Q88E |
| jGCaMP8.640 (sensitive) | 9 | N19T_S24I_S26R_Q88E_M419S |
| jGCaMP8.712 (high dynamic range) | 11 | (T19N) (I24S) S26R_M28S_Q88E |
| jGCaMP8.543 (high dynamic range) | 13 | N19T_S24I_S26R_Q88E_M346Q |
| jGCaMP8.707 (high baseline brightness) | 15 | N19T_S24I_S26R_Q88E_F286Y_E288Q_Q315H |
| jGCaMP8.455 (high baseline brightness) | 17 | N19T_S24I_S26R_Q88E_Q315K |
| jGCaMP6s_ENOSP | 19 | RS20 peptide replaced with ENOSP |
| jGCaMP6s_ENOSP_linker1 | 21 | Linker 1 mutated in jGCaMP6s_ENOSP |
| jGCaMP7f | 22 | (previous scaffold) | versal Nuclease (Thermo Fisher) and subsequently centrifuged. Supernatants were applied to HisPur Cobalt Resin (Thermo Fisher). The resin was washed with 20 column volumes of 20 mM Tris, pH 8.0, 300 mM NaCl, 1 mM imidazole, followed by 10 column volumes of 20 mM Tris, pH 8.0, 500 mM NaCl, 5 mM imidazole. Proteins were eluted into 20 mM Tris, pH 8.0, 100 mM NaCl, 100 mM imidazole.

For calcium titrations, sensors were diluted 1:100 in duplicate into 30 mM MOPS, pH 7.2, 100 mM KCl containing either 10 mM CaEGTA (39 μM free calcium) or 10 mM EGTA (0 μM free calcium). As before, these two solutions were mixed in different amounts to give 11 different free calcium concentrations. GCaMP fluorescence (485 nm excitation, 5 nm bandpass; 510 nm emission, 5 nm bandpass) was measured in a Tecan Safire2 plate reader (Tecan). The data was fit with a sigmoidal function using KaleidaGraph (Synergy Software) to extract the $K_d$ for $Ca^{2+}$, the Hill coefficient, and dynamic range.

$k_{off}$ was determined at room temperature using a stopped-flow device coupled to a fluorometer (Applied Photophysics). Each sensor variant in 1 μM $Ca^{2+}$ in 30 mM MOPS, pH 7.2, 100 mM KCl was rapidly mixed with 10 mM EGTA in 30 mM MOPS, pH 7.2, 100 mM KCl. Fluorescence decay data was fit with a single or double exponential decay function.

For pH titrations, purified proteins were diluted into pH buffers containing 50 mM citrate, 50 mM Tris, 50 mM glycine, 100 mM NaCl and either 2 mM $CaCl_2$) or 2 mM EGTA, which were pre-adjusted to 24 different pH values between 4.5 and 10.5 with NaOH. A sigmoidal function was used to fit fluorescence versus pH, and the $pK_a$ value was determined from the midpoint.

Sequence and Structural Analysis of Variants

Linker1 encodes Leu-Glu in GCaMP6s (and indeed, in all previous RS20-based GCaMP sensors—this linker was extensively mutated in the GCaMP5 screen (Akerboom et al., 2012, J. Neurosci., 32(40):13819-40), but the best variant, GCaMP5G, retained Leu-Glu); we first mutated Leu-Glu to fully degenerate 2-amino acid (aa) sequences and screened for variants with both high signal change and retained fast kinetics. Following selection of the best 2-aa linkers, these variants were expanded to libraries of 3-aa linkers by addition of fully degenerate residues.

All promising variants contain, in addition to the Leu-Lys-Ile linker 1, additional mutations to the ENOSP peptide: Asn19Thr and Ser24Ile appear in every variant except 712, Ser26Arg appears in every variant but jGCaMP8s (with Ser26Met), jGCaMP8m has Ala25Gly, and 712 has Met28Ser. Every variant contains the Gln88Glu mutation at the CaM-GFP interface. Further mutations include Phe286Tyr (8s, 8m, and 707); Glu288Gln (707); Gln315Leu (8f), Gln315His (8s, 707), Gln315Lys (455); Met346Gln (543); and Met419Ser (640). Of these, Phe286Tyr derives from the FGCaMP sensor; all others are unique to this work. Importantly, GCaMP6s data from both purified protein and cultured neurons are essentially identical between this work (lacking the RSET tag) and previous work (with it) (data not shown), implying that the RSET tag does not noticeably modulate GCaMP function in protein and neuronal culture and that observed jGCaMP8 improvements stem from the peptide substitution and other mutations.

Screening in Neuronal Cell Culture

GCaMP variants were cloned into an hSynI-GCaMP-NLS-mCherry-WPRE expression vector, and XCaMP variants (XCaMP-G, XCaMP-Gf, XCaMP-Gf0) were cloned into an AAV-hSynI-XCaMP-NES vector. We used the nuclear export sequence (NES) for the XCaMP sensors, as this was how they were characterized in Inoue et al. (2019, Cell, 177(5): 1346-60). As this excludes the XCaMP sensors from the nucleus, where $Ca^{2+}$ signals are slower, whereas the variants developed here were not excluded, this will make the XCaMPs appear faster than they really are compared to the GCaMP indicators.

The primary rat culture procedure was performed as described (Dana et al., 2019, Nat. Methods, 16(7):649-57). Briefly, neonatal rat pups (Charles River Laboratory) were euthanized, and neocortices were dissociated and processed to form a cell pellet. Cells were resuspended and transfected by combining $5 \times 10^5$ viable cells with 400 ng plasmid DNA and nucleofection solution in a 25-μL electroporation cuvette (Lonza). Electroporation of GCaMP mutants was performed according to the manufacturer's protocol.

Neurons were plated onto poly-D-lysine (PDL) coated, 96-well, glass bottom plates (MatTek) at $\sim 1 \times 10^5$ cells per well in 100 L of a 1:2 mixture of NbActiv4 (BrainBits) and plating medium (28 mM glucose, 2.4 mM NaHCO3, 100 μg/mL transferrin, 25 μg/mL insulin, 2 mM L-glutamine, 100 U/mL penicillin, 10 μg/mL streptomycin, 10% FBS in MEM). Typically, each plate included GCaMP6s (8 wells), GCaMP6f (8 wells), jGCaMP7f (8 wells). Other wells were electroporated with mutated variants (4 wells per variant), for a total of 80 wells (the first and last columns in the plate were not used). Plates were left in the incubator at 37° C. and 5% $CO_2$.

On DIV 14-19, neurons underwent field stimulation and imaging (Dana et al., 2019, Nat. Methods, 16(7):649-57; Wardill et al., 2013, PLOS One, 8(10):e77728). Fluorescence time-lapse images (200 Hz; total of 7 seconds) were collected on an Olympus IX81 microscope using a 10×, 0.4 NA objective (UPlanSApo, Olympus) and an ET-GFP filter cube (Chroma #49002). A 470 nm LED (Cairn Research) was used for excitation (intensity at the image plane, 0.34 mW/mm$^2$). Images were collected using an EMCCD camera (Ixon Ultra DU897, Andor) with 4×4 binning, corresponding to a 0.8 mm×0.8 mm FOV. Reference images (100 ms exposure) were used to perform segmentation. Red illumination for variants co-expressing mCherry was performed with a 590 nm LED (Cairn Research) through a ET-mCherry filter cube (Chroma #49008) with an intensity of 0.03 mW/mm$^2$. Trains of 1, 3, 40, and 160 field stimuli were delivered with a custom stimulation electrode. For sensor linearity measurements, 1, 2, 3, 5, 10, and 40 field stimuli were delivered.

The responses of individual variants were analyzed as described (Chen et al., 2013, Nature, 499:295-300; Dana et al., 2019, Nat. Methods, 16(7):649-57). The Ilastik toolkit (Berg et al., 2019, Nat. Methods, 16(12):1226-32) was used to segment cell bodies in the reference images. Wells with fewer than five detected neurons and wells with poor neuronal proliferation were discarded. Plates with more than four discarded control (GCaMP6s) wells were discarded and re-screened. The $\Delta F/F_0$, SNR, and kinetics (half-rise, half-decay, time to peak) metrics were computed for each cell. Median values from each well are reported to quantify performance. Each observation was normalized to median GCaMP6s from the same experimental batch. Baseline brightness for constructs co-expressing mCherry (Table 4) was calculated by dividing the GFP cellular fluorescence in the beginning of the 3 AP stimulation epoch by the mCherry cellular fluorescence (for a ratiometric measurement). For comparison with XCaMP variants (in FIG. 19), no mCherry normalization was performed, but all baseline brightness values were still normalized to GCaMP6s in the same transfection week. To determine significant differences in observations between constructs, a two-tailed Mann-Whitney U-test was performed between constructs and controls (GCaMP6s or jGCaMP7f). A median $\Delta F/F_0$ trace was computed across all detected cell bodies in a well for each stimulus. Photobleaching was corrected in the 1 AP recordings by fitting a double exponential to the beginning and end segments of the fluorescence trace.

Baseline Fluorescence Measurements

In a separate round of measurements from those measuring $\Delta F/F_0$, SNR, and kinetics, the baseline fluorescence of jGCaMP8 series was compared to jGCaMP7f and the XCaMP series. Due to significant week-to-week variability in baseline fluorescence, all constructs for this experiment were transfected side-by-side (2 consecutive transfection weeks, 5 96-well plates). To eliminate possible plate-to-plate variability within the transfected batch, the baseline fluorescence of each construct was normalized to in-plate GCaMP6s. Displayed in FIG. 20.

We then characterized the photobleaching properties of jGCaMP8 and associated controls (FIG. 20). After continuous illumination for 10 minutes, neurons transfected with jGCaMP8 GECIs lost on average 13-28% of their initial fluorescence. jGCaMP8m exhibited biphasic bleaching: a rapid phase consisting of ~15% fluorescence loss within 10 s followed by a slower phase (10% within 10 minutes). Of the other variants, jGCaMP7c also exhibited this property. We noticed considerable variability in the photobleaching rates within individual neurons, possibly stemming from differences in baseline brightness in each neuron as a function of intracellular resting $[Ca^{2+}]$.

Fluorescence Recovery After Photobleaching

FRAP experiments were carried out on a Nikon Ti-E inverted microscope outfitted with a Yokogowa CSU-X1 spinning disk and an Andor DU-897 EMCCD camera. Excitation for fluorescence imaging was carried out using a solid-state laser line at 488 nm, and emission was collected with 100× 1.49NA objective (Nikon Instruments) through a standard GFP filter set. Photobleaching was performed using a Bruker Mini-Scanner by focusing a 405 nm laser to a single, diffraction-limited point spread function at a defined location for 100 ms. Cultured neurons plated in 35 mm glass-bottom dishes (MatTek) were immersed in regular imaging buffer with the addition of synaptic blockers (same as used for neuronal culture field stimulation) and 1 µM TTX to block AP generation. In a subset of experiments, the buffer was supplemented with 5 µM ionomycin. Bleaching spots were chosen to be on the soma of the neuron but distant from the nucleus. A spot was photobleached 10 times (0.1 Hz) as the cell was concurrently imaged at 25 or 50 FPS.

For analysis, pixels within a 1.5 µm radius around the bleach spot were averaged in each frame. The resulting fluorescence trace was normalized to the mean fluorescence of an identically sized spot on the opposite side of the soma, outside the nucleus. The trace was then split into 10 epochs (each corresponding to a bleaching event) and the fluorescence fi (t) of each epoch i was normalized by dividing by the fluorescence value immediately preceding the bleaching pulse fi ($t_{pre}$)) as follows:

$$\bar{f}i(t) = \frac{fi(t)}{fi(t_{pre})}$$

The resistant fraction was calculated as follows:

$$RF(\%) = 100 \left(1 - \bar{f}_1(t_{fin}) - \frac{1}{9}\sum_{i=2}^{10}(1 - \bar{f}_i(t_{fin}))\right)$$

where $\bar{f}i$ ($t_{fin}$) is the final fluorescence value at the end of epoch i and the final term in the equation is the averaged fluorescence loss of all epochs after the first. This term is subtracted to account for the overall fluorescence loss with each bleaching pulse.

Crystal Structure Determination

All GCaMP samples for crystallization were in 20 mM Tris, 150 mM NaCl, pH 8, 2 mM $CaCl_2$). All crystallization trials were carried out at 22° C. with the hanging-drop vapor diffusion method. Commercial sparse-matrix screening solutions (Hampton Research) were used in initial screens. 1 µL of protein solution was mixed with 1 µL of reservoir solution and equilibrated against 300 µL of reservoir solution. Diffraction data were collected at the beamline 8.2.1 at Berkeley Center for Structural Biology and processed with XDS (Kabsch, 2010, Acta Crystallogr. D. Biol. Crystallogr., 66(Pt 2):125-32). The phase was determined by molecular replacement using MOLREP (Vagin & Teplyakov, 2010, Acta Crystallorg. D. Biol. Crystallorg., 66(Pt 1):22-5), and the structure of GCaMP2 (PDB 3EK4) without the RS20 peptide as the starting model. Refinement was performed using REFMAC (Winn et al., 2003, Methods Enzymol., 374:300-21), followed by manual remodeling with Coot (Emsley & Cowtan, 2004, Acta Crystallogr. D. Biol. Crystallorg., 60(Pt 12 Pt 1):2126-32).

Mouse Surgeries

Young adult (postnatal day 50-214) male C57BL/6J (Charles River) mice were anesthetized using isoflurane (2.5% for induction, 1.5% during surgery). A circular craniotomy (3 mm diameter) was made above VI (centered 2.5 mm left and 0.5 mm anterior to the Lambda suture). Viral suspension (30 nL) was injected in 4-5 locations on a 500 µm grid, 300-400 µm deep (AAV2/1-hSynapsin-1-jGCaMP8 constructs (pGP-AAV-syn1-jGCaMP8f-WPRE, Addgene plasmid #162376, 4e12 GC/mL titer; pGP-AAV-syn1-jGCaMP8m-WPRE, Addgene plasmid #162375, 2.2e12 GC/mL titer; pGP-AAV-syn1-jGCaMP8s-WPRE, Addgene plasmid #162374, 2.1e12 GC/mL titer). A 3 mm diameter circular coverslip glued to a donut-shaped 3.5 mm diameter coverslip (No. 1 thickness, Warner Instruments) was cemented to the craniotomy using black dental cement (Contemporary Ortho-Jet). A custom titanium head post was cemented to the skull. An additional surgery was performed for loose-seal recordings. 18-80 days after the virus injection, the mouse was anesthetized with a mixture of ketamine-xylazine (0.1 mg ketamine and 0.008 mg xylazine per gram body weight), and we surgically removed the cranial window and performed durotomy (Goldey et al., 2014, Nat. Protoc., 9(11):2515-38). The craniotomy was filled with 10-15 µL of 1.5% agarose, then a D-shaped coverslip was secured on top to suppress brain motion, but leaving access to the brain on the lateral side of the craniotomy.

2P Population Imaging

Mice were kept on a warm blanket)(37° C. and anesthetized using 0.5% isoflurane and sedated with chlorprothixene (20-30 µL at 0.33 mg/ml, intramuscular). Imaging was performed with a custom-built two-photon microscope with a resonant scanner. The light source was an Insight femtosecond-pulse laser (Spectra-Physics) running at 940 nm. The objective was a ×16 water immersion lens with 0.8 numerical aperture (Nikon). The detection path consisted of a custom filter set (525/50 nm (functional channel), 600/60 nm (cell targeting channel) and a 565 nm dichroic mirror) ending in a pair of GaAsP photomultiplier tubes (Hamamatsu). Images were acquired using ScanImage (vidriotechnologies.com) (Pologruto et al., 2003, Biomed. Eng. Online, 2:13). Functional images (512×512 pixels, 215×215 µm$^2$; or 512×128 pixels, 215×55 µm$^2$) of L2/3 cells (50-250 µm under the pia mater) were collected at 30 Hz or 122 Hz. Laser power was up to 50 mW at the front aperture of the objective unless stated otherwise for the XCaMPgf experiments.

Loose-Seal Recordings

Micropipettes (3-9 MΩ) were filled with sterile saline containing 20 µM Alexa-594. Somatic cell attached recordings were obtained from upper layer 2 neurons (50-200 µm depth from brain surface) visualized with the shadow patching technique (Kitamura, 2008, Nat. Methods, 5(1):61-7). Spikes were recorded either in current clamp or voltage clamp mode. Signals were filtered at 20 kHz (Multiclamp 700B, Axon Instruments) and digitized at 50 kHz using Wavesurfer (available at wavesurfer.janelia.org/). The frame trigger pulses of ScanImage were also recorded and used offline to synchronize individual frames to electrophysiological recordings. After establishment of a low-resistance seal (15-50 MOhm), the randomized visual stimulation was delivered to increase the activity of the cells in the field of view. In a small subset of recordings, we microstimulated the recorded neuron in voltage clamp recording mode by applying DC current to increase its firing probability.

Visual Stimulation

Visual stimuli (applying DC current to increase its firing probability (Perkins, 2006)) were moving gratings generated using the Psychophysics Toolbox in MATLAB (Mathworks), presented using an LCD monitor (30×40 cm$^2$), placed 25 cm in front of the center of the right eye of the mouse. Each stimulus trial consisted of a 2 s blank period (uniform gray display at mean luminance) followed by a 2 s drifting sinusoidal grating (0.05 cycles per degree, 1 Hz temporal frequency, eight randomized different directions). The stimuli were synchronized to individual image frames using frame-start pulses provided by ScanImage.

Post hoc Anatomy

After the loose-seal recording sessions, mice were deeply anesthetized with a mixture of ketamine-xylazine (0.1 mg ketamine and 0.008 mg xylazine per gram body weight) and were transcardially perfused with 4% PFA in 1X DPBS. The brains were extracted and post-fixed overnight in the perfusing solution. The brains were sectioned at 50 µm thickness, blocked with 2% BSA+0.4 triton-100 (in PBS) for 1 h at room temperature, incubated with primary antibody (Rb-anti-GFP, 1:500, Invitrogen, #G10362) for 2 days at 4° C., secondary antibody (Alexa 594 conjugated goat anti-Rb, 1:500, Invitrogen, #A-11012) overnight at 4° C. The sections were mounted on microscope slides in Vectashield hard-set antifade mounting medium with DAPI (H-1500, Vector). Samples were imaged using a TissueFAXS 200 slide scanner (TissueGnostics, Vienna, Austria) comprising an X-Light V2 spinning disk confocal imaging system (CrestOptics, Rome, Italy) built on an Axio Imager.Z2 microscope (Carl Zeiss Microscopy, White Plains, NY) equipped with a Plan-Apochromat 20×/0.8 M27 objective lens.

Data Analysis

The acquired data was analyzed using MATLAB (population imaging) or Python (imaging during loose-seal recordings). In the MATLAB pipeline, for every recorded FOV, we selected ROIs covering all identifiable cell bodies using a semi-automated algorithm, and the fluorescence time course was measured by averaging all pixels within individual ROIs, after correction for neuropil contamination (r=0.7), as described in detail in (Chen et al., 2013, Nature, 499:295-300). We used one-way ANOVA test (P=0.01) for identifying cells with significant increase in their fluorescence signal during the stimulus presentation (responsive cells). We calculated $\Delta F/F0=(F-F_0)/F_0$, where F is the instantaneous fluorescence signal and F0 is the average fluorescence 0.7 s before the start of the visual stimulus. For each responsive cell, we defined the preferred stimulus as the stimulus that evoked the maximal $\Delta F/F_0$ amplitude (averaging the top 25% of $\Delta F/F0$ values during the 2 s of stimulus presentation). The half-decay time was calculated as follows, for each responsive cell, we averaged its $\Delta F/F_0$ response to the preferred stimulus over five trials. We also calculated the standard deviation of the averaged baseline signal during 0.7 s before the start of the stimulus. Only cells where maximal $\Delta F/F_0$ amplitude was higher than four standard deviations above the baseline signal were included in the analysis. The time required for each trace to reach half of its peak value (baseline fluorescence subtracted) was calculated by linear interpolation. The fraction of cells detected as responsive was calculated as the number of significantly responsive cells over all the cells that were analyzed. The cumulative distribution of peak $\Delta F/F_0$ responses included the maximal response amplitude from all analyzed cells, calculated as described above for each cell's preferred stimulus. The orientation sensitivity index (OSI) was calculated as before (Chen et al., 2013, Nature, 499: 295-300; Dana et al., 2019, Nat. Methods, 16(7):649-57), by fitting the fluorescence response from individual cells to the eight drifting grating stimuli with two Gaussians, centered at the preferred response angle (Rpref) and the opposite angle (Ropp). The OSI was calculated as $$OSI = \frac{R_{pref} - R_{orth}}{R_{pref} + R_{orth}}$$

where $R_{orth}$ is the orthogonal angle to the preferred angle.

The movies recorded during loose-seal recordings were motion corrected and segmented with the python implementation of Suite2p (github.com/MouseLand/suite2p) (Stringer et al., 2016, Elife, 5:e19695). The ROI corresponding to the loose-seal recorded cell was then manually selected from the automatically segmented ROIs. For this dataset, we calculated the neuropil contamination for most of the movies and got a distribution with a median of r_neu~0.8 (FIG. 29), so we used this value uniformly for neuropil correction. Calcium events were defined by grouping action potentials with a 20 ms inclusion window. Then we calculated $\Delta F/F0=(F-F0)/F0$, where F is the instantaneous fluorescence signal and F0 was defined separately for all calcium events as the mean fluorescence value of the last 200 ms before the first action potential in the group. We also calculated a global $\Delta F/F_0$ trace $(\Delta F/F_0)_{global}$ where we used the 20th percentile of the fluorescence trace in a 60 s long running window as the $F0_{global}$. In the analyses, we only included calcium events where this $(\Delta F/F_0)_{global}$ value was less than 0.5 right before the action potential, to include only events that start near baseline fluorescence values, in order to exclude non-linear summation and saturation.

*Drosophila* L2 Assay

GCaMP variants were tested by crossing males carrying the variant to a w+; 53G02-Gal4$^{AD}$ (in attP40); 29G11-Gal4$^{DBD}$ (in attP2) females. Flies were raised at 21° C. on standard cornmeal molasses media.

Females 3-5 days after eclosure were anesthetized on ice. After transferring to a thermoelectric plate (4° C.), legs were removed, and then facing down, the head was glued into a custom-made pyramid using UV-cured glue. The proboscis was pressed in and fixed using UV-cured glue. After adding saline (103 mM NaCl, 3 mM KCl, 1 mM NaH2PO4, 5 mM TES, 26 mM NaHCO$_3$, 4 mM MgCl2, 2.5 mM CaCl2, 10 mM trehalose and 10 mM glucose, pH 7.4, 270-275 mOsm) to the posterior side of the head, cuticle was cut away above the right side creating a window above the target neurons. Trachea and fat were removed. Muscles M1 and M6 were cut to minimize head movement.

Two photon imaging took place under a 40×N.A. 0.8 water-immersion objective (Olympus) on a laser scanning microscope (BrukerNano, Middleton, WI) with GaAsP photomulitplier tubes (PMTs). Laser power was kept constant at 8 mW using Pockel cells. No bleaching was evident at this laser intensity. The emission dichroic was 580 nm and emission filters 511/20-25 nm. Images were 32×128 pixels with a frame rate at 372 Hz.

A MATLAB script produced the visual stimulation via a digital micromirror device (DMD, LightCrafter) at 0.125 Hz onto a screen covering the visual field in front of the right eye. A blue led (474/23-25) emitting through a 474/23-25 bandpass filter provided illumination.

Light dimming produced a stereotypical calcium increase in L2 neurons (Behnia et al. 2014, Nature, 512(7515):427-30; Strother et al., 2017, Neuron, 94(1):168-182; Strother, Nern, and Reiser, 2014, Curr. Biol., 24(9):976-83). Intensity measurements were taken in medulla layer 2. A target region image was chosen by testing each consecutive layer with 0.5 Hz full field visual stimulation until a layer with maximum ΔF/F$_0$ was identified. Then 2-3 columns producing a maximum response were identified in the layer. Imaging then targeted this region over a protocol involving multiple tests (see Table 4).

TABLE 4

Describing the L2 Testing Protocol

| Cycle | Frequency Off | Frequency On | Trials | Volt (Lights) | Volt (Light Time (s)) | Descriptor |
|---|---|---|---|---|---|---|
| 1 | 0.5 | | 10 | 0 | 5 | 20Frequency |
| 2 | 25 | 500 | 25 | 0 | 5 | 14Dark Flash |
| 3 | 8 | 500 | 25 | 0 | 5 | 12Dark Flash |
| 4 | 4 | 500 | 25 | 0 | 5 | 12Dark Flash |
| 5 | 0.5 | | 10 | 0 | 5 | 20Frequency |
| 6 | 30 | | 600 | 0 | 5 | 20Frequency |
| 7 | 28 | | 560 | 0 | 5 | 20Frequency |
| 8 | 26 | | 520 | 0 | 5 | 20Frequency |
| 9 | 24 | | 480 | 0 | 5 | 20Frequency |
| 10 | 22 | | 440 | 0 | 5 | 20Frequency |
| 11 | 20 | | 400 | 0 | 5 | 20Frequency |
| 12 | 18 | | 360 | 0 | 5 | 20Frequency |
| 13 | 16 | | 320 | 0 | 5 | 20Frequency |
| 14 | 14 | | 280 | 0 | 5 | 20Frequency |
| 15 | 12 | | 240 | 0 | 5 | 20Frequency |
| 16 | 10 | | 200 | 0 | 5 | 20Frequency |
| 17 | 8 | | 160 | 0 | 5 | 20Frequency |
| 18 | 6 | | 120 | 0 | 5 | 20Frequency |
| 19 | 4 | | 80 | 0 | 5 | 20Frequency |
| 20 | 2 | | 40 | 0 | 5 | 20Frequency |
| 21 | 1 | | 20 | 0 | 5 | 20Frequency |
| 22 | 0.5 | | 10 | 0 | 5 | 20Frequency |
| 23 | 2000 | 500 | 15 Ramp | | 5 | 45Ramp |
| 24 | 1000 | 500 | 15 Ramp | | 5 | 23Ramp |
| 25 | 3000 | 500 | 15 Ramp | | 5 | 67.5Ramp |
| 26 | 25 | 500 | 25 | 2.5 | 5 | 12Dark Flash |
| 27 | 25 | 500 | 25 | 0 | 2.5 | 12Dark Flash |
| 28 | 8 | 500 | 25 | 2.5 | 5 | 14Dark Flash |
| 29 | 8 | 500 | 25 | 0 | 2.5 | 14Dark Flash |
| 30 | 500 | 25 | 25 | 0 | 5 | 14Light Flash |
| 31 | 500 | 8 | 25 | 0 | 5 | 12Light Flash |
| 32 | 500 | 4 | 25 | 0 | 5 | 12Light Flash |
| 33 | 0.5 | | 10 | 0 | 5 | 20Frequency |

Image analysis was performed using custom python scripts. ROIs were chosen to include 2-3 columns that produced maximum ΔF/F$_0$ responses. In addition to the ROI containing L2 columns, a background ROI was selected where no fluorescence was evident. The mean intensity in the background was subtracted from the mean L2 ROI. In the ΔF/F$_0$ calculation, baseline included the last 1/5 images taken during at the end of the light period. Stimulus onset is the light to dark transition. Change in fluorescence ΔF is the intensity subtracted baseline. ΔF/F$_0$ is ΔF divided by baseline. The final signal is processed through a gaussian filter (σ=3).

Quantifying Protein Levels

NMJ Staining

Variants were crossed to pan-neuronal driver line, also containing tdTomato, (pJFRC22-10XUAS-IVS-myr::tdTomato in su(Hw)attP8;; R57C10 at VK00020, R57C10 at VK00040) to allow staining in the NMJ. The 3rd instar larvae were filleted and fixed following standard techniques (Aso et al., 2014, Elife, 3:e04580). Primary chicken anti-GFP (Thermo Fisher A10262, 1:1000) and secondary goat anti-chicken AF488 plus (Thermo Fisher A32931, 1:800) targeted GCaMP variants. Primary rabbit anti-RFP (Clontech 632496, 1:1000) and secondary goat anti-rabbit Cy3 (Jackson 111-165-144, 1:1000) targeted tdTomato.

MBON-γ2a'1 Staining

Variants were co-co expressed with myr::tdTomato using the MB077B driver. Adults 3-6 days old were harvested, brains dissected, and fixed using standard techniques. GCaMP variants were directly labeled with anti-GFP (AF488, Molecular Probes A-21311, 1:500). Primary Rat anti-RFP (mAb 5F8 Chromotek, 1:500) and secondary goat anti-rat Cy3 (Jackson 112-165-167, 1:1000) labeled the tdTomato.

Analyzing IHC Staining

ROIs were draw on targeted regions using custom python scripts. Within the ROIs otsu-thresholding was used to identify regions expressing myr::tdTomato. Intensity measurements were then taken for both the variant and tdTomato within these regions. The ratio is the intensity from the green channel (variant staining) divided by the intensity from the red channel (myr::tdTomato staining).

Western Blot

Protein was extracted from female brains with the same genotype used in the NMJ IHC staining. Western blot was performed following standard techniques. Variant was stained using primary rabbit anti-GFP (Millipore Sigma) and secondary goat anti-rabbit IgG conjugated to HRP (Thermo). Actin was stained using mouse IgM anti-a actin (Thermo, 1:5000) and goat anti-mouse IgG and IgM-HRP (Thermo, 1:5000). Signal formed using SuperSignal West Dura luminescence and imaged on a BioRad Gel imager. Band intensity was measured using FIJI. Band intensity from the variant was divided by band intensity from the actin band to determine the ratio.

Imaging in the Drosophila Larval Neuromuscular Junction

We made 20XUAS—IVS-Syn21-op1-GECI-p10 in VK00005 transgenic flies and crossed them with 10XUAS-IVS-myr::tdTomato in su(Hw)attP8×R57C10-Gal4 at VK00020; R57C10-Gal4 at VK00040 pan-neuronal driver line. Sensor cDNAs were codon-optimized for Drosophila for improving expression. The NMJ assay is similar to our previous study (Dana et al., 2019, Nat. Methods, 16(7):649-57). Briefly, female 3rd instar larvae were dissected in chilled)(4° C. Schneider's Insect Medium (Sigma) to fully expose the body wall muscles. Segment nerves were severed in proximity to ventral nerve cord (VNC). Dissection medium was then replaced with room temperature HL-6 saline in which 2 mM of calcium and 7 mM of L-glutamic acid were added to block synaptic transmission and muscle contraction. A mercury lamp (X-CITE exacte) light source was used for excitation and out-of-objective power of was less than 5 mW to reduce bleaching. Type Ib boutons on muscle 13 from segment A3-A5 were imaged while the corresponding hemi-segment nerve were stimulated with square voltage pulses (4 V, 0.3 ms pulse width, 2 s duration, 1-160 Hz frequency) through a suction electrode driven by a customized stimulator. Bath temperature and pH were continuously monitored with a thermometer and PH meter, respectively, and recorded throughout the experiment. The filters for imaging were: excitation: 472/30; dichroic: 495; emission: 520/35. Images were captured with an EMCCD (Andor iXon 897) at 128.5 fps and acquired with Metamorph software. ROIs around boutons were manually drawn and data were analyzed with a custom Python script.

Reagent Distribution and Data Availability

DNA constructs and AAV particles of jGCaMP8s, jGCaMP8m, and jGCaMP8f (pCMV, pAAV-synapsin-1, pAAV-synapsin-1-FLEX, and pAAV-CAG-FLEX) have been deposited at Addgene (#162371-162382). Drosophila stocks were deposited at the Bloomington Drosophila Stock Center (at flystocks.bio.indiana.edu on the World Wide Web). Fish lines are available on request. The majority of datasets generated for characterizing the new sensors are included in the published article (and its supplementary information files). Additional datasets are available from the corresponding authors on reasonable request.

Part B-Results

Sensor Design

We surveyed the Protein Data Bank for unique structures of calmodulin (CaM) in complex with a peptide. Twenty-nine peptides were sufficiently different from the RS20 peptide sequence used in previous GCaMPs to warrant testing (Table 4). The structures of these complexes were superimposed on the GCaMP2 structure (PDB 3EK4) in PyMOL, and amino acids were added or removed to bring all peptides to a length estimated to work well in the GCaMP topology. Synthetic DNA encoding each of the 29 peptides replaced the RS20 peptide in the bacterial expression vector pRSET-GCaMP6s. Of the initial sensors, 20/29 showed calcium sensing. All variants had lower $(\Delta F/F_0)_{max}$ than GCaMP6s, all but three had weaker $Ca^{2+}$ affinity ($K_d$) than GCaMP6s, all but one had lower cooperativity (Hill coefficient, n), and many were dimmer (Table 4). Several initial sensor variants showed much faster $Ca^{2+}$ decay kinetics, as determined by stopped-flow fluorescence on purified protein (Table 4). Based on fast kinetics, $(\Delta F/F_0)_{max}$, $K_d$, Hill coefficient, and apparent brightness, we prioritized those based on the peptides from endothelial nitric oxide synthase (PDB INIW; peptide "ENOSP") and death-associated protein kinase 1 (1YR5; peptide "DAPKP") for optimization (Table 4).

TABLE 4

Biophysical Properties of Various Sensors with Different Calmodulin-Binding Peptides

| PDBID/ peptide name | Sequence of the peptides | SEQ ID NO: | Kd nM | Max ΔF/F | Hill Coefficient | $K_{off1}$ ($S^{-1}$) | $K_{off2}$ ($S^{-1}$) | Normalized $F_0$ |
|---|---|---|---|---|---|---|---|---|
| 1CDL | ARRKWQKTGHAVRAIGRLSS | 25 | 205 | 50 | 2.1 | 1.87 | | 1.18 |
| 1CDM | LKKFNARRKLKGAILTTMLATRNFS | 26 | 728 | 14.5 | 2 | 6.03 | 5.76 | 1.80 |
| 1IQ5 | VRVIPRLDTLILVKAMGHRKRFGNPFR | 27 | N/A | N/A | N/A | N/A | N/A | 5.13 |
| 1IWQ | KKRFSFKKSFKLSGFSFKK | 28 | 3436 | 10.6 | 1.4 | | | 2.17 |
| 1NIW | RKKTFKEVANAVKISASLMG | 29 | 1062 | 14.8 | 2 | 23.01 | 0.12 | 1.42 |
| 1SY9 | GGFRRIARLVGVLREWAYR | 30 | 67 | 11.9 | 2.7 | 8.13 | 0.45 | 0.91 |
| 1YR5 | RKKWKQSVRLISLCQRLSR | 31 | 205 | 18 | 1.8 | 15.01 | 0.39 | 2.19 |
| 2BCX | KSKKAVWHKLLSKQRRRAVVACFRM | 32 | 3288 | 5.8 | 2 | | | 3.08 |
| 2F3Y | KFYATFLIQEYFRKFKK | 33 | N/A | N/A | N/A | N/A | N/A | 1.98 |
| 2FOT | ASASPWKSARLMVHTVATFNSIKER | 34 | 34.2 | 7.4 | 2.1 | 1.92 | 0.057 | 1.68 |
| 2HQW | KKKATFRAITSTLASSFKR | 35 | 682 | 29.9 | 1.7 | 5.01 | 0.43 | 1.65 |
| 2KNE | LRRGQILWFRGLNRIQTQIKVVKAFHS | 36 | 38.1 | 11 | 1.4 | 1.99 | | 1.82 |
| 2LGF | AFIIWLARRLKKGKK | 37 | N/A | N/A | N/A | N/A | N/A | 1.87 |
| 2M55 | MDVFMKGLSKAKEGWAAA | 38 | N/A | N/A | N/A | N/A | N/A | 0.97 |

TABLE 4-continued

Biophysical Properties of Various Sensors with Different Calmodulin-Binding Peptides

| PDBID/peptide name | Sequence of the peptides | SEQ ID NO: | Kd nM | Max ΔF/F | Hill Coefficient | $K_{off1}$ ($S^{-1}$) | $K_{off2}$ ($S^{-1}$) | Normalized $F_0$ |
|---|---|---|---|---|---|---|---|---|
| 2MES | MDCLCIVTTKKYRYQD | 39 | N/A | N/A | N/A | N/A | N/A | 0.29 |
| 2N6A | AAGSGWRKIKLAVRGAQAK | 40 | N/A | N/A | N/A | N/A | N/A | 1.52 |
| 2o60 | KRRAIGFKKLAEAVKFSAKLMG | 41 | 653 | 16.6 | 1.7 | 24.5 | 0.68 | 1.57 |
| 2VAY | KFYATFLIQEHFRKFMKRQEE | 42 | 1814 | 2.2 | 1.1 | | | 0.93 |
| 3BXX | KIYAAMMIMEYYRQSKAKKLQ | 43 | 615 | 3.5 | 1.9 | | | 1.66 |
| 3EWT | SKYITTIAGVMTLSQV | 44 | 5931 | 17.9 | 1 | | | 0.35 |
| 3GOF | RRREIRFRVLVKVVFFSS | 45 | 490 | 41.6 | 1.8 | 1.89 | | 0.26 |
| 3GP2 | SFNARRKLKGAILTTMLATAS | 46 | 1523 | 31.4 | 1.6 | | | 0.66 |
| 3SUI | GRVSGRNWKNFALVPLLRDAS | 47 | N/A | N/A | N/A | N/A | N/A | 1.41 |
| 4AQRA | ERLQQWRKAALVLNASRRFRY | 48 | 420 | 22 | 1.8 | 2.82 | | 1.52 |
| 4AQRB | REMRQKIRSHAHALLAANRFMDM | 49 | 865 | 16 | 1.9 | 6.04 | 1.15 | 0.92 |
| 4Q5U | ARKEVIRNKIRAIGKMARVFSVLR | 50 | 705 | 17.1 | 1.8 | 28.9 | 1.32 | 1.17 |
| 4UPU | NHWQKIRTMVNLPVISPFKSS | 51 | 13000 | | | | | 1.60 |
| 5DOW | KRNKALKKIRKLQKRGLIQMT | 52 | N/A | N/A | N/A | N/A | N/A | 0.55 |
| RS20[1] | SSRRKWNKTGHAVRAIGRLSS | 53 | 131 | 56.5 | 2.2 | 1.09 | | 1.00 |
| CKKAP[2] | VKLIPSLTTVILVKSMLRKRSFGNPF | 54 | N/A | N/A | N/A | N/A | N/A | 1.91 |
| 6GGS[3] | GGSGGSGGSGGSGGSGGS | 55 | N/A | N/A | N/A | N/A | N/A | 1.48 |

Sensor Optimization

These two sensor scaffolds were optimized in protein purified from *E. coli* expression. Libraries were constructed to mutate the linker connecting the peptide to cpGFP (linker 1) (Akerboom et al., 2012, J. Neurosci., 32(40):13819-40) and screened for high signal change and retained fast kinetics. The linker connecting cpGFP and CaM (linker 2) was similarly mutated on top of variants from the optimization of linker 1. Out of 4000 ENOSP-based variants and 1600 DAPKP-based variants, 23 and 10 respectively had fast kinetics and high (ΔF/F$_0$)max in purified protein (data not shown).

These promising sensors were tested in response to action potentials (APs) elicited in cultured neurons in 96-well plates. Action potentials produce essentially instantaneous increases in calcium (Maravall et al., 2000, Biophys. J., 78(5):2655-67) and are therefore ideal to screen for GECIs with fast kinetics (Pologruto et al., 2004, J. Neurosci., 24(43):9572-9). Fluorescence changes were extracted from multiple single neurons per well. Sensors were evaluated according to several properties (Appendix A): sensitivity (response to 1 AP), dynamic range (response to a saturating train of 160 APs, applied at high frequency), kinetics (rise and decay times to 1 AP), and baseline brightness. Sensors based on DAPKP showed fast decay time and good sensitivity compared to jGCaMP7f—but with slow rise times (Appendix A). Sensors with ENOSP had similar sensitivity and significantly faster rise and decay times than jGCaMP7f (Appendix A).

We prioritized ENOSP-based sensors for further optimization. ENOSP variant jGCaMP8.410.80 (linker 1 Leu-Lys-Ile) showed 1.8-fold faster half-rise time and 4.4-fold faster half-decay time than jGCaMP7f, with similar resting brightness and dynamic range, and 35% lower 1-AP response. We solved the crystal structure of jGCaMP8.410.80 (FIG. 12A; FIG. 18A). The overall structure is similar to previous GCaMP versions. The main differences are at the 3-way interface between cpGFP, CaM, and the new ENOSP peptide (FIG. 13B). Guided by the crystal structure, we targeted 16 interface positions for site-saturation mutagenesis: 7 in ENOSP, 4 on cpGFP, and 5 on CaM (FIG. 18A). Sensor variants were tested in cultured neurons for higher sensitivity in detecting neural activity while maintaining fast kinetics. Several single mutations improved properties (Appendix A), particularly residues near the ENOSP C-terminus and the cpGFP-CaM interface. Beneficial point mutations were combined in subsequent rounds of screening (FIG. 18B). Ten additional CaM positions (FIG. 18A) surrounding ENOSP were subjected to site-saturation mutagenesis. Finally, mutations (FIG. 18A) from the FGCaMP sensor (developed using CaM and RS20-like peptide sequences from the fungus *Aspergillus niger* and the yeast *Komagataella pastoris*) (Barykina et al., 2017, PLOS One, 10.1371; Barykina et al., 2020, Int. J. Mol. Sci., 10.3390) were introduced to improve biorthogonality and/or kinetics.

Mutagenesis and screening in neurons covered 776 total sensor variants, of which 683 (88%) produced detectable responses to 1 AP (FIG. 17, Appendix A). Kinetics were improved relative to the previous fast sensor jGCaMP7f.

Specifically, compared to jGCaMP7f, the half-rise time (t rise, 1/2) was significantly shorter in 48% of screened variants, the time to peak fluorescence (t peak) was significantly shorter in 47%, and the half-decay time ($t_{decay, 1/2}$) was significantly shorter in 40%. Sensitivity (1-AP $\Delta F/F_0$) was higher than jGCaMP7f in 19%, and only 2% of variants had increased saturation response (160-AP $\Delta F/F_0$). Together, the mutagenesis produced a large set of variants with significant improvement in kinetics and sensitivity (Appendix A).

jGCaMP8 Characterization

Three high-performing "jGCaMP8" variants were selected for additional characterization (FIG. 12B-12G). jGCaMP8f ("fast") exhibited 1-AP $t_{rise. 1/2}$ of 7.0±0.7 ms, and 1-AP $t_{peak}$ of 24.9±6.0 ms, more than 3- and 5-fold shorter than jGCaMP7f, respectively. jGCaMP8s ("sensitive") exhibited 1-AP $\Delta F/F_0$ of 1.1±0.2, and 1-AP signal-to-noise ratio (SNR) of 41.3±10.4, approximately twice that of the most sensitive GECI to date, jGCaMP7s. jGCaMP8m ("medium") is a useful compromise between sensitivity and kinetics: it exhibits 1-AP $\Delta F/F_0$ and 1-AP SNR comparable to jGCaMP7s, and kinetics comparable to jGCaMP8f, with the exception of a slower half-decay time ($t_{decay, 1/2}$, 134±14 vs. 92±22 ms; FIG. 12B). The fast kinetics and high sensitivity of the jGCaMP8 indicators allowed resolution of electrically evoked spikes at frequencies of up to 40 Hz (FIG. 12H); jGCaMP7f performed quite poorly. When stimulated with short bursts consisting of 3 and 10 APs, the jGCaMP8 sensors retained fast kinetics and high sensitivity. Overall, the jGCaMP8 series exhibited significant, multi-fold improvements across several parameters over previous GECIs.

We next compared the jGCaMP8 sensors to the XCaMP series (green XCaMP variants XCaMP-G, XCaMP-Gf, and XCaMP-Gf$_0$ (Inoue et al., 2019, Cell, 177(5):1346-60), side-by-side in cultured neurons. The 1-AP $\Delta F/F_0$ was significantly higher for all jGCaMP8 sensors; the 1-AP SNR was significantly higher for jGCaMP8m and jGCaMP8s, 1-AP $t_{rise. 1/2}$ was significantly shorter for all jGCaMP8 sensors, 1-AP $t_{peak}$ was significantly shorter for jGCaMP8f and jGCaMP8m, and $t_{decay, 1/2}$ was significantly shorter for jGCaMP8f, when evaluated against all XCaMP sensors (FIG. 12D-12G; Appendix A). The baseline fluorescence of the jGCaMP8 series was similar to jGCaMP7f, and significantly higher than the XCaMP sensors (FIG. 19). Photobleaching was also similar between jGCaMP7f and the jGCaMP8 sensors (FIG. 15).

GECIs with linear (i.e., Hill coefficient ~1) fluorescence responses to APs provide a larger effective dynamic range of AP detection and facilitate applications such as counting spikes within trains; large slope (m) values further aid this. Conversely, highly cooperative sensors magnify signals from small bursts, thus offering greater sensitivity. The jGCaMP8 sensors are more linear and have higher slope from 1-10 AP than previous GECIs (FIG. 16). Reassuringly, characterization in purified protein (FIG. 17; Table 5) showed similar affinity, kinetics, and cooperativity as in neuronal culture. Finally, the jGCaMP8 variants showed similar diffusion in neurons (FIG. 30) followed by fluorescence recovery after photobleaching (FRAP), suggesting that they do not have altered cellular interactions versus previous GECIs.

TABLE 5

Characterization of Purified Protein

| | jGCaMP7f | jGCaMP8f | jGCaMP8m | jGCaMP8s |
|---|---|---|---|---|
| Kd, nM | 150 ± 2 | 334 ± 18 | 108 ± 3 | 46 ± 1 |
| Hill Coefficient | 3.10 ± 0.16 | 2.08 ± 0.22 | 1.92 ± 0.12 | 2.20 ± 0.13 |
| Max dF/F | 31.0 + 1.1 | 78.8 + −9.7 | 45.7 + −0.9 | 49.5 + −0.1 |
| $k_{off}$, fast (s$^{-1}$) | 7.34 ± 0.12 | 37.03 ± 0.75 | 18.25 ± 0.31 | 3.68 ± 0.04 |
| $k_{off}$, fast % | | 91% | | |
| $k_{off}$, slow (s$^{-1}$) | | 1.37 ± 3.49 | | |
| $k_{off}$, slow % | | 9% | | |
| pKa, apo | 8.68 ± 0.13 | 7.71 ± 0.06 | 7.40 ± 0.02 | 7.65 ± 0.04 |
| pKa, sat | 6.71 ± 0.06 | 6.68 ± 00.01 | 6.68 ± 0.07 | 6.51 ± 0.04 |
| $\lambda_{exi}$ (nm) | 497 | 497 | 497 | 498 |
| $\lambda_{emi}$ (nm) | 512 | 512 | 512 | 513 |
| $\lambda_{abs}$ (nm) | 496 | 496 | 496 | 496 |
| EC$_{sat}$ (M$^{-1}$ cm$^{-1}$) | 52458 | 50759 | 49856 | 56960 |
| EC$_{apo}$ (M$^{-1}$ cm$^{-1}$) | 2783 | 1927 | 2249 | 2116 |

Imaging Neural Populations in Mouse Primary Visual Cortex

We next tested the jGCaMP8 sensors in L2/3 pyramidal neurons of mouse primary visual cortex (V1). We made a craniotomy over V1 and infected neurons with adeno-associated virus (AAV2/1-hSynapsin-1) (Huber et al., 2012, Nature, 484(7395):473-8) encoding a jGCaMP8 variant, jGCaMP7f or XCaMP-Gf. After three weeks of expression, mice were lightly anesthetized and mounted under a custom two-photon microscope. Full-field, high-contrast drifting gratings were presented in each of eight directions to the contralateral eye (FIG. 13A). Two-photon frame-scan imaging (30 Hz) was performed of L2/3 somata and neuropil.

With the jGaMP8 indicators, visual stimulus-evoked fluorescence transients were observed in many cells (FIG. 13B, 13C; three representative cells shown) and were stable across trials (FIG. 21). All sensors produced transients with sharp rise and decay (FIG. 13B-13E). Nearly identical responses were measured after long-term expression of jGCaMP8 (five additional weeks; FIG. 22).

The dynamics of sensory stimuli were tracked by fluorescence changes (FIG. 13B, 13C). Consistent with in vitro characterization (FIG. 12), jGCaMP8f showed significantly shorter half-decay time (median=84 ms) than jGCaMP7f (median=110 ms) but comparable to jGCaMP8m (84 ms) or XCaMP-Gf (91 ms) (FIG. 13E). On the other hand, jGCaMP8s decay was significantly slower than the other indicators.

We quantified indicator sensitivity both as the proportion of labeled neurons responsive to visual stimuli (FIG. 13F) and as the cumulative distribution of peak $\Delta F/F_0$ across cells (FIG. 13G). Significantly, more responsive cells were seen for jGCaMP8s and jGCaMP8m than for jGCaMP8f and jGCaMP7f (FIG. 13F). Furthermore, jGCaMP8s was dramatically right-shifted relative to the other indicators, reflective of its high sensitivity and $(\Delta F/F_0)$max. XCaMP-Gf was quite dim and had few responsive cells, precluding sensitivity analysis. As protein expression levels were similar across indicators (FIG. 23), XCaMP-Gf is deficient in maturation, brightness, and/or signal change in vivo and was not studied further. SNR of visually evoked fluorescence transients was significantly higher for jGCaMP8s than for other sensors, followed by jGCaMP8m and jGCaMP7s, and then by the rest (FIG. 13G).

Orientation tuning was similar for all sensors, except that jGCaMP8m and jGCaMP8s revealed a larger proportion of neurons with low orientation selectivity (FIG. 24). A potential explanation for this is that the high-sensitivity indicators detect activity of GABAergic interneurons that is missed by the other sensors. Interneurons are highly buffered, yielding smaller and slower fluorescence responses, and have much less sharp tuning than excitatory neurons. This possibility is bolstered by the experimental results shown in FIG. 25.

Simultaneous Imaging and Electrophysiology

To quantify GECI responses to precise neural activity stimuli, we combined two-photon frame-scan imaging (122 Hz) and loose-seal, cell-attached electrophysiological recordings in V1. We compared fluorescence changes and spiking across sensors (n=44 cells, jGCaMP8f; n=47, jGCaMP8m; n=53, jGCaMP8s; n=26, jGCaMP7f; FIG. 26, FIG. 27). All jGCaMP8 variants produced large fluorescence transients even in response to single action potentials (APs) (FIG. 14A, 14B).

Each recorded neuron occupied less than $\frac{1}{5}^{th}$ of the laser scan lines of each imaging frame and the neurons were scanned at random phases with respect to the recorded action potentials to avoid any bias during recording (FIG. 29). Across action potentials, fluorescence responses were thus sampled with effective temporal resolutions of approximately 500 Hz. All three jGCaMP8 variants showed rapid rise times (0-80%) below 10 ms, approximately 3x faster than jGCaMP7f (FIG. 14C, 14D). Peak responses for jGCaMP8m and jGCaMP8s were also larger than for jGCaMP7f.

Indicator rise time is the limiting determinant of neural activity deconvolution algorithms and spike-timing estimates. The much faster rise times of the jGCaMP8 indicators should thus translate into better resolution of individual APs in bursts. We binned action potential doublets with respect to their inter-spike interval length. The jGCaMP8 indicators conclusively resolved individual action potentials at spike rates of up to 100 Hz (FIG. 14F).

We also grouped spike bursts based on the number of APs in a 20 ms integration window. All sensors show monotonic increases in fluorescence response with AP count, with the jGCaMP8 sensors responding more linearly than jGCaMP7f (FIG. 14G). This greater linearity is consistent with neuronal culture results and lower Hill coefficients in purified protein (Table 5). The jGCaMP8 indicators performed much better than GCaMP6 or jGCaMP7 in fitting fluorescence traces from diverse spike trains, reflecting their improved linearity, SNR, and kinetics (Jiang et al., 2020, PloS Comput. Biol., 16(4):e1007522).

Finally, in our recordings we identified fast-spiking (FS, presumably parvalbumin-expressing) interneurons, judged by their high spike rates and short spike durations (FIG. 25). All three jGCaMP8 sensors produced robust responses (~5% $\Delta F/F_0$) to single APs in FS interneurons, much larger than GCaMP6s. jGCaMP8f and jGCaMP8m maintained their rapid kinetics, returning to baseline between bursts, whereas jGCaMP8s did not. The excellent SNR and dynamic range of jGCaMP8f and jGCaMP8m in FS interneurons likely results from their fast on-rates, enabling them to outcompete endogenous PV $Ca^{2+}$ buffering.

Taken together, in mouse cortex in vivo, the jGCaMP8 sensors show excellent single-spike detection, spike-time estimation and burst deconvolution, good expression, strong performance in fast-spiking interneurons, and no evidence of adverse effects of long-term expression. jGCaMP8m and jGCaMP8s are the most sensitive GECIs to date, and jGCaMP8m and jGCaMP8f are the fastest.

Imaging in the *Drosophila* L2 Neurons and Expression Levels

GCaMP responses to visual stimulation were compared in *Drosophila* laminar monopolar L2 neurons (FIG. 14A), part of the OFF-motion visual system. Intensity measurements were taken where L2 dendrites connect to columns in medulla layer 2. These non-spiking neurons depolarize during light decrease and hyperpolarize during increase. Fluorescence response to visual stimulation were followed in multiple single neurons in individual animals (FIG. 14B). At dark-light and light-dark transitions, jGCaMP8 variants showed faster rise and decay than 7f (FIG. 14C, 14D; half-rise times: 7f, 128+10 ms; 8f, 76±8; 8m, 58±6; 8s, 80±8 ms). Decay times also decreased: 7f, 149±15 ms; 8f, 94±16; 8m, 7310 ms.

Since the jGCaMP8 variants showed faster kinetics, they should be able to follow activity changes at faster frequencies than jGCaMP7f. Variants were tested at visual stimulation frequencies from 0.5-30 Hz. The jGCaMP8f and jGCaMP8m variants had increased power across faster frequencies (FIG. 14E), demonstrating improved ability to follow fast transients.

In addition, faster rise-time should produce more sensitive responses to weak signals. Visual simulation using short (4 ms, 8 ms, and 24 ms) dimming periods elicited a range of responses in L2 neurons (FIG. 14F). The 8f and 8m variants proved more sensitive when detecting responses to the shorter stimuli. The d' measure provides a likelihood to detect a signal. When d' is 2, detection is probable but false positives remain high and only fall off when d' increases above 3. The d' metric improves from 2.3±0.08 for 7f to 3.0±0.2 for 8f and 3.5±0.2 for 8m at 8 ms duration. At 4 ms, d' for 7f scored at 2.1±0.08 but increased to 2.5±0.1 for 8f and 2.9±0.2 for 8m. This indicates that using the 8 variants described herein will reduce the false positive rate in signal detection.

Variants 8f and 8m have increased $\Delta F/F_0$ responses due to lower baseline fluorescence compared to 7f. Both 8f and 8m have similar changes in fluorescence ($\Delta F$) to 7f (FIG. 18). However, mean fluorescent intensity taken over the entire trial period, irrespective of the lighting transition, is lower (FIG. 15A, 15B). This reduced fluorescence is the reason why 8f and 8m had increased $\Delta F/F_0$ responses compared to 7f. During the 0.5 Hz stimulation, 7f was the brightest variant, being 3 times brighter than 8f and 2 times brighter than 8m. XCaMP was included in the comparison, and it was the dimmest variant with 7f being 44 times brighter. Although dim, responses to visual stimulation could be detected using XCaMP (FIG. 15C). Detecting in individual responses was marginal since during the 25 ms dark flash, the XCaMP d' scored (2.3±0.19) lower than 7f (3.5±0.21) during the 25 ms dark flash (MRS p-value=0.046).

Since in vitro study found no difference in quantum efficiency between 8 and 7f, protein expression levels were assessed using Western and immunostained neurons to determine if differences in expression could explain the mean fluorescent differences. Western blots loaded with protein expressed pan-neuronally and isolated from the adult CNS found ~3 times more protein in 7f compared to other variants (FIG. 14A). XCaMP did not have significantly different protein levels compared to 8. Images from immunostaining within the NMJ and MBON-γ2a'1 confirmed the Western blot findings. In these neurons, GCaMP variants and myr::tdTomato were co-expressed and the ratio in staining between these two proteins consistently found reduced GCaMP staining (FIG. 14B, 14C). Subdividing the MBON-γ2a'1 neuron into ROIs including the cell body, axons and dendrites consistently found reduced 8 and XCaMP protein levels in all regions compared to 7f.

Imaging in the *Drosophila* Larval Neuromuscular Junction

We next imaged jGCaMP8 variants as well as jGCaMP7f and XCaMP-Gf in presynaptic boutons of the *Drosophila* larval NMJ in response to electrical stimuli of motor axons. The jGCaMP8 GECIs as well as jGCaMP7f exhibited robust responses to electrical stimulation. XCaMP-Gf was generally too dim to image, produced poor fluorescent signal, and was therefore not included for subsequent analysis. jGCaMP7f had the most robust response at high frequency (>40 Hz) stimuli, and all responses of jGCaMP8 sensors and jGCaMP7f as control saturated when stimulated at 80 Hz or above. All jGCaMP8 sensors displayed a faster rise kinetics at 40 Hz stimuli than jGCaMP7f. The decay kinetics showed a clear separation of jGCaMP8f, jGCaMP8m and jGCaMP8s, with the latter slightly slower than jGCaMP7f. All jGCaMP8 sensors have a lower baseline fluorescence level, consistent with in vivo adult fly imaging. jGCaMP8 series are more capable in detecting individual stimuli at low frequencies (1-10 Hz), and this is confirmed with power spectra analysis which further shows jGCaMP8m is the most sensitive sensor in detecting 5, 10 and 20 Hz stimuli.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A nucleic acid molecule encoding a genetically encoded calcium indicator (GECI) polypeptide, wherein the GECI polypeptide comprises an amino acid sequence having at least 99% sequence identity to a sequence shown in SEQ ID NO:1, SEQ ID NO:3, SEQ ID NO:5, SEQ ID NO:7, SEQ ID NO:9, SEQ ID NO:11, SEQ ID NO: 13, SEQ ID NO:15, SEQ ID NO:17, SEQ ID NO: 19, or SEQ ID NO:21.

2. The nucleic acid molecule of claim 1, wherein the GECI comprises an amino acid sequence shown in SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO:19, or SEQ ID NO:21.

3. The nucleic acid molecule of claim 1, having the sequence shown in SEQ ID NO:2, SEQ ID NO:4, SEQ ID NO:6, SEQ ID NO:8, SEQ ID NO: 10, SEQ ID NO: 12, SEQ ID NO:14, SEQ ID NO: 16, SEQ ID NO: 18, SEQ ID NO:20, or SEQ ID NO:22.

4. A vector comprising the nucleic acid molecule of claim 1.

5. A cell comprising the vector of claim 4.

6. A cell comprising the nucleic acid molecule of claim 1.

7. A GECI polypeptide, wherein the polypeptide comprises an amino acid sequence having at least 99% sequence identity to a sequence shown in SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO: 17, SEQ ID NO: 19, or SEQ ID NO:21.

8. The polypeptide of claim 7, wherein the polypeptide comprises an amino acid sequence shown in SEQ ID NO:1, SEQ ID NO:3, SEQ ID NO:5, SEQ ID NO:7, SEQ ID NO:9, SEQ ID NO:11, SEQ ID NO: 13, SEQ ID NO: 15, SEQ ID NO: 17, SEQ ID NO: 19, or SEQ ID NO:21.

9. A cell comprising the polypeptide of claim 7.

10. A method of screening agents for agonists or antagonists of G-protein coupled receptor (GPCR) polypeptides, comprising:

(i) contacting a test agent with a cell comprising a GPCR polypeptide and a genetically encoded calcium indicator (GECI) polypeptide, wherein the GECI polypeptide comprises an amino acid sequence having at least 99% sequence identity to SEQ ID NO:1, SEQ ID NO:3, SEQ ID NO:5, SEQ ID NO:7, SEQ ID NO:9, SEQ ID NO: 11, SEQ ID NO: 13, SEQ ID NO:15, SEQ ID NO: 17, SEQ ID NO: 19, or SEQ ID NO:21; and (ii) determining a level of fluorescence produced by the cell, wherein an increase in fluorescence relative to a control indicates that the test agent is an agonist of the GPCR polypeptide and wherein a decrease in fluorescence relative to a control indicates that the test agent is an antagonist of the GPCR polypeptide.

11. The method of claim 10, wherein the cell is in vitro.

12. The method of claim 10, wherein the cell is in vivo.

13. The method of claim 12, wherein the cell is in vivo in a mouse, a worm, a rat, a fish, or a fly.

14. The method of claim 10, wherein the agent is selected from the group consisting of a nucleic acid, a polypeptide, a chemical compound, a small molecule and combinations thereof.

15. The method of claim 14, wherein the nucleic acid is an inhibitory nucleic acid.

16. The method of claim 15, wherein the inhibitory nucleic acid is a triplex forming oligonucleotide, an aptamer, a ribozyme, an antisense RNA, a short interfering RNA (siRNA), or a micro-RNA (miRNA).

17. The method of claim 14, wherein the polypeptide is an antibody.

18. A method of monitoring the activity of a cell, comprising:
(i) providing a cell comprising a GPCR and a GECI, wherein the GECI comprises an amino acid sequence having at least 99% sequence identity to a sequence shown in SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO: 17, SEQ ID NO: 19, or SEQ ID NO:21;
(ii) stimulating the cell; and
(iii) detecting the fluorescence emitted by the cell.

19. A nucleic acid molecule encoding a calmodulin-binding peptide portion of a genetically encoded calcium indicator (GECI) polypeptide, wherein the peptide portion of the GECI polypeptide comprises an amino acid sequence having at least 95% sequence identity to residues 10-29 of the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or the entirety of SEQ ID NO: 45 or SEQ ID NO: 51.

20. A calmodulin-binding peptide portion of a GECI polypeptide, wherein the peptide portion comprises an amino acid sequence having at least 95% sequence identity to residues 10-29 of the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or the entirety of SEQ ID NO: 45 or SEQ ID NO: 51.

21. A method of imaging neurons in mouse primary visual cortex (V1), comprising:
introducing a nucleic acid encoding a jGCaMP8 sensor into a neuronal cell under conditions in which the nucleic acid is expressed, wherein the nucleic acid has at least 99% sequence identity to a sequence shown in SEQ ID NO:2, SEQ ID NO:4, SEQ ID NO:6, SEQ ID NO:8, SEQ ID NO: 10, SEQ ID NO:12, SEQ ID NO: 14, SEQ ID NO: 16, SEQ ID NO: 18, SEQ ID NO:20, or SEQ ID NO:22, or wherein the nucleic acid encodes a polypeptide having at least 99% sequence identity to the amino acid sequence shown in SEQ ID NO:1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO:17, SEQ ID NO:19, or SEQ ID NO:21; and
recording neuronal response to drifting grating stimuli.

22. A method of discriminating single action potentials in vivo, comprising:
introducing a nucleic acid encoding a jGCaMP8 sensor into a neuronal cell under conditions in which the nucleic acid is expressed, wherein the nucleic acid has at least 99% sequence identity to a sequence shown in SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, or SEQ ID NO:22, or wherein the nucleic acid encodes a polypeptide having at least 99% sequence identity to the amino acid sequence shown in SEQ ID NO:1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO:17, SEQ ID NO: 19, or SEQ ID NO:21;
thereby significantly improving spike deconvolution.

23. A method of imaging neurons, comprising:
introducing a nucleic acid encoding a jGCaMP8 sensor into a neuronal cell under conditions in which the nucleic acid is expressed, wherein the nucleic acid has at least 99% sequence identity to a sequence shown in SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, or SEQ ID NO:22, or wherein the nucleic acid encodes a polypeptide having at least 99% sequence identity to the amino acid sequence shown in SEQ ID NO:1, SEQ ID NO:3, SEQ ID NO:5, SEQ ID NO:7, SEQ ID NO:9, SEQ ID NO: 11, SEQ ID NO:13, SEQ ID NO: 15, SEQ ID NO:17, SEQ ID NO:19, or SEQ ID NO:21; and
imaging the neurons.

24. A method of monitoring neuronal activity in cells, comprising:
introducing a nucleic acid encoding a jGCaMP8 sensor into a neuronal cell under conditions in which the nucleic acid is expressed, wherein the nucleic acid has at least 99% sequence identity to a sequence shown in SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, or SEQ ID NO:22, or wherein the nucleic acid encodes a polypeptide having at least 99% sequence identity to the amino acid sequence shown in SEQ ID NO:1, SEQ ID NO:3, SEQ ID NO:5, SEQ ID NO:7, SEQ ID NO:9, SEQ ID NO:11, SEQ ID NO: 13, SEQ ID NO: 15, SEQ ID NO:17, SEQ ID NO:19, or SEQ ID NO:21; and
monitoring neuronal activity.

25. A method of monitoring cells, comprising:
introducing a nucleic acid encoding a jGCaMP8 sensor into a cell under conditions in which the nucleic acid is expressed, wherein the nucleic acid has at least 99% sequence identity to a sequence shown in SEQ ID NO:2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20, or SEQ ID NO:22, or wherein the nucleic acid encodes a polypeptide having at least 99% sequence identity to the amino acid sequence shown in SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, or SEQ ID NO:21; and
monitoring the cell.

\* \* \* \* \*

SEQUENCE LISTING

```
<160> NUMBER OF SEQ ID NOS: 55

<210> SEQ ID NO 1
<211> LENGTH: 422
<212> TYPE: PRT
<213> ORGANISM: Artificial
<220> FEATURE:
<223> OTHER INFORMATION: Synthetically-generated construct

<400> SEQUENCE: 1

Met His His His His His His Thr Arg Arg Lys Lys Thr Phe Lys Glu
1               5                   10                  15

Val Ala Thr Ala Val Lys Ile Ile Ala Arg Leu Met Gly Leu Lys Ile
                20                  25                  30

Asn Val Tyr Ile Lys Ala Asp Lys Gln Lys Asn Gly Ile Lys Ala Asn
            35                  40                  45

Phe His Ile Arg His Asn Ile Glu Asp Gly Gly Val Gln Leu Ala Tyr
        50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125

Met Val Ser Lys Gly Glu Glu Leu Phe Thr Gly Val Val Pro Ile Leu
    130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
```

195                 200                 205
Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Leu Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Met Ala Arg Lys Met Lys Tyr
            340                 345                 350

Arg Asp Thr Glu Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
    370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 2
<211> LENGTH: 1269
<212> TYPE: DNA
<213> ORGANISM: Artificial
<220> FEATURE:
<223> OTHER INFORMATION: Synthetically-generated construct

<400> SEQUENCE: 2
atgcatcatc accatcatca cacgcgtcgc aagaagacct tcaaggaggt ggccaccgcc      60
gtgaagatca tcgcccgcct gatgggcctg aagatcaacg tctatatcaa ggccgacaag     120
cagaagaacg gcatcaaggc gaacttccac atccgccaca catcgagga cggcggcgtg      180 cagctcgcct accactacca gcagaacacc cccatcggcg acggcccgt gctgctgccc      240 gacaaccact acctgagcgt ggagtccaaa ctttcgaaag accccaacga aagcgcgat     300 cacatggtcc tgctggagtt cgtgaccgcc gccgggatca ctctcggcat ggacgagctg     360
tacaagggcg gtaccggagg gagcatggtg agcaagggcg aggagctgtt caccggggtg     420
gtgcccatcc tggtcgagct ggacggcgac gtaaacggcc acaagttcag cgtgtccggc     480
gagggtgagg gcgatgccac ctacggcaag ctgaccctga agttcatctg caccaccggc     540
aagctgcccg tgccctggcc caccctcgtg accaccctga cctacggcgt gcagtgcttc     600
agccgctacc ccgaccacat gaagcagcac gacttcttca gtccgccat gcccgaaggc     660 tacatccagg agcgcaccat cttcttcaag gacgacggca actacaagac ccgcgccgag     720
gtgaagttcg agggcgacac cctggtgaac cgcatcgagc tgaagggcat cgacttcaag     780

-continued

```
gaggacggca acatcctggg gcacaagctg gagtacaacc tgccggacca actgactgaa    840
gagcagatcg cagaatttaa agaggctttc tccctatttg acaaggacgg ggatgggaca    900
ataacaacca aggagctggg gacggtgatg cggtctctcg gactgaaccc cacagaagca    960
gagctgcagg acatgatcaa tgaagtagat gccgacggtg acggcacaat cgacttccct   1020
gagttcctga caatgatggc aagaaaaatg aaatacaggg acacggaaga agaaattaga   1080
gaagcgttcg gtgtgtttga taaggatggc aatggctaca tcagtgcagc agagcttcgc   1140
cacgtgatga caaaccttgg agagaagtta acagatgaag aggttgatga aatgatcagg   1200
gaagcagaca tcgatgggga tggtcaggta aactacgaag agtttgtaca aatgatgaca   1260
gcgaagtaa                                                           1269
```

<210> SEQ ID NO 3
<211> LENGTH: 422
<212> TYPE: PRT
<213> ORGANISM: Artificial
<220> FEATURE:
<223> OTHER INFORMATION: Synthetically-generated construct

<400> SEQUENCE: 3

```
Met His His His His His Thr Arg Arg Lys Lys Thr Phe Lys Glu
1               5                   10                  15

Val Ala Thr Ala Val Lys Ile Ile Ala Met Leu Met Gly Leu Lys Ile
            20                  25                  30

Asn Val Tyr Ile Lys Ala Asp Lys Gln Lys Asn Gly Ile Lys Ala Asn
        35                  40                  45

Phe His Ile Arg His Asn Ile Glu Asp Gly Gly Val Gln Leu Ala Tyr
    50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125

Met Val Ser Lys Gly Glu Glu Leu Phe Thr Gly Val Val Pro Ile Leu
    130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270
```

```
Asn Leu Pro Asp Gln Leu Thr Glu Glu Gln Ile Ala Glu Tyr Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly His Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Met Ala Arg Lys Met Lys Tyr
            340                 345                 350

Arg Asp Thr Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
    370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 4
<211> LENGTH: 1269
<212> TYPE: DNA
<213> ORGANISM: Artificial
<220> FEATURE:
<223> OTHER INFORMATION: Synthetically-generated construct

<400> SEQUENCE: 4
atgcatcatc accatcatca cacgcgtcgc aagaagacct tcaaggaggt ggccaccgcc    60
gtgaagatca tcgccatgct gatgggcctg aagatcaacg tctatatcaa ggccgacaag   120
cagaagaacg gcatcaaggc gaacttccac atccgccaca catcgagga cggcggcgtg   180 cagctcgcct accactacca gcagaacacc cccatcggcg acggccccgt gctgctgccc   240
gacaaccact acctgagcgt ggagtccaaa ctttcgaaag accccaacga gaagcgcgat   300
cacatggtcc tgctggagtt cgtgaccgcc gccgggatca ctctcggcat ggacgagctg   360
tacaagggcg gtaccggagg gagcatggtg agcaagggcg aggagctgtt caccggggtg   420
gtgcccatcc tggtcgagct ggacggcgac gtaaacggcc acaagttcag cgtgtccggc   480
gagggtgagg gcgatgccac ctacggcaag ctgaccctga gttcatctg caccaccggc   540 aagctgcccg tgccctggcc caccctcgtg accaccctga cctacggcgt gcagtgcttc   600
agccgctacc ccgaccacat gaagcagcac gacttcttca gtccgccat gcccgaaggc   660 tacatccagg agcgcaccat cttcttcaag gacgacggca actacaagac ccgcgccgag   720
gtgaagttcg agggcgacac cctggtgaac cgcatcgagc tgaagggcat cgacttcaag   780
gaggacggca acatcctggg cacaagctg gagtacaacc tgccggacca actgactgaa   840
gagcagatcg cagaatacaa agaggctttc tccctatttg acaaggacgg ggatgggaca   900
ataacaacca aggagctggg gacggtgatg cggtctctcg gacacaaccc cacagaagca   960
gagctgcagg acatgatcaa tgaagtagat gccgacggtg acggcacaat cgacttccct  1020
gagttcctga caatgatggc aagaaaaatg aaatacaggg acacgaaga agaaattaga  1080 gaagcgttcg gtgtgtttga taaggatggc aatggctaca tcagtgcagc agagcttcgc  1140
```

-continued

```
cacgtgatga caaaccttgg agagaagtta acagatgaag aggttgatga aatgatcagg    1200
gaagcagaca tcgatgggga tggtcaggta aactacgaag agtttgtaca aatgatgaca    1260
gcgaagtaa                                                           1269
```

<210> SEQ ID NO 5
<211> LENGTH: 422
<212> TYPE: PRT
<213> ORGANISM: Artificial
<220> FEATURE:
<223> OTHER INFORMATION: Synthetically-generated construct

<400> SEQUENCE: 5

```
Met His His His His His His Thr Arg Arg Lys Lys Thr Phe Lys Glu
1               5                   10                  15

Val Ala Thr Ala Val Lys Ile Ile Gly Arg Leu Met Gly Leu Lys Ile
            20                  25                  30

Asn Val Tyr Ile Lys Ala Asp Lys Gln Lys Asn Gly Ile Lys Ala Asn
        35                  40                  45

Phe His Ile Arg His Asn Ile Glu Asp Gly Gly Val Gln Leu Ala Tyr
    50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125

Met Val Ser Lys Gly Glu Glu Leu Phe Thr Gly Val Val Pro Ile Leu
130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Tyr Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
                325                 330                 335
```

Ile Asp Phe Pro Glu Phe Leu Thr Met Met Ala Arg Lys Met Lys Tyr
                340                 345                 350

Arg Asp Thr Glu Glu Glu Ile Arg Glu Ala Phe Gly Val Phe Asp Lys
            355                 360                 365

Asp Gly Asn Gly Tyr Ile Ser Ala Ala Glu Leu Arg His Val Met Thr
        370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 6
<211> LENGTH: 1269
<212> TYPE: DNA
<213> ORGANISM: Artificial
<220> FEATURE:
<223> OTHER INFORMATION: Synthetically-generated construct

<400> SEQUENCE: 6
atgcatcatc accatcatca cacgcgtcgc aagaagacct tcaaggaggt ggccaccgcc        60
gtgaagatca tcggccgcct gatgggcctg aagatcaacg tctatatcaa ggccgacaag       120
cagaagaacg gcatcaaggc gaacttccac atccgccaca catcgagga cggcggcgtg       180 cagctcgcct accactacca gcagaacacc cccatcggcg acggcccgt gctgctgccc       240 gacaaccact acctgagcgt ggagtccaaa ctttcgaaag accccaacga gaagcgcgat       300
cacatggtcc tgctggagtt cgtgaccgcc gccgggatca ctctcggcat ggacgagctg       360
tacaagggcg gtaccggagg gagcatggtg agcaagggcg aggagctgtt caccggggtg       420
gtgcccatcc tggtcgagct ggacggcgac gtaaacggcc acaagttcag cgtgtccggc       480
gagggtgagg gcgatgccac ctacggcaag ctgaccctga gttcatctg caccaccggc       540 aagctgcccg tgccctggcc caccctcgtg accaccctga cctacggcgt gcagtgcttc       600
agccgctacc ccgaccacat gaagcagcac gacttcttca gtccgccat gcccgaaggc       660 tacatccagg agcgcaccat cttcttcaag gacgacggca actacaagac ccgcgccgag       720
gtgaagttcg agggcgacac cctggtgaac cgcatcgagc tgaagggcat cgacttcaag       780
gaggacggca acatcctggg cacaagctg gagtacaacc tgccggacca actgactgaa       840
gagcagatcg cagaatacaa agaggctttc tccctatttg acaaggacgg ggatgggaca       900
ataacaacca aggagctggg gacggtgatg cggtctctcg acagaacccc cacagaagca       960
gagctgcagg acatgatcaa tgaagtagat gccgacggtg acggcacaat cgacttccct      1020
gagttcctga caatgatggc aagaaaaatg aaatacaggg acacggaaga agaaattaga      1080
gaagcgttcg gtgtgtttga taaggatggc aatggctaca tcagtgcagc agagcttcgc      1140
cacgtgatga caaaccttgg agagaagtta acagatgaag aggttgatga atgatcagg       1200 gaagcagaca tcgatgggga tggtcaggta aactacgaag agtttgtaca atgatgaca      1260 gcgaagtaa                                                              1269

<210> SEQ ID NO 7
<211> LENGTH: 422
<212> TYPE: PRT
<213> ORGANISM: Artificial
<220> FEATURE:
<223> OTHER INFORMATION: Synthetically-generated construct -continued

```
<400> SEQUENCE: 7

Met His His His His His Thr Arg Arg Lys Lys Thr Phe Lys Glu
1               5                   10                  15

Val Ala Thr Ala Val Lys Ile Ile Ala Arg Leu Met Gly Leu Lys Ile
            20                  25                  30

Asn Val Tyr Ile Lys Ala Asp Lys Gln Lys Asn Gly Ile Lys Ala Asn
            35                  40                  45

Phe His Ile Arg His Asn Ile Glu Asp Gly Gly Val Gln Leu Ala Tyr
        50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Thr Gly Gly Ser
        115                 120                 125

Met Val Ser Lys Gly Glu Glu Leu Phe Thr Gly Val Val Pro Ile Leu
130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Met Ala Arg Lys Met Lys Tyr
            340                 345                 350

Arg Asp Thr Glu Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
    370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
```

Gln Met Met Thr Ala Lys
        420

<210> SEQ ID NO 8
<211> LENGTH: 1269
<212> TYPE: DNA
<213> ORGANISM: Artificial
<220> FEATURE:
<223> OTHER INFORMATION: Synthetically-generated construct

<400> SEQUENCE: 8

```
atgcatcatc accatcatca cacgcgtcgc aagaagacct tcaaggaggt ggccaccgcc      60
gtgaagatca tcgcccgcct gatgggcctg aagatcaacg tctatatcaa ggccgacaag     120
cagaagaacg gcatcaaggc gaacttccac atccgccaca catcgagga cggcggcgtg      180
cagctcgcct accactacca gcagaacacc cccatcggcg acggccccgt gctgctgccc     240
gacaaccact acctgagcgt ggagtccaaa ctttcgaaag accccaacga gaagcgcgat     300
cacatggtcc tgctggagtt cgtgaccgcc gccgggatca ctctcggcat ggacgagctg     360
tacaagggcg gtaccggagg gagcatggtg agcaagggcg aggagctgtt caccggggtg     420
gtgcccatcc tggtcgagct ggacggcgac gtaaacggcc acaagttcag cgtgtccggc     480
gagggtgagg gcgatgccac ctacggcaag ctgaccctga gttcatctg caccaccggc      540
aagctgcccg tgccctggcc caccctcgtg accaccctga cctacggcgt gcagtgcttc     600
agccgctacc ccgaccacat gaagcagcac gacttcttca gtccgccat gcccgaaggc      660
tacatccagg agcgcaccat cttcttcaag gacgacggca actacaagac ccgcgccgag     720
gtgaagttcg agggcgacac cctggtgaac cgcatcgagc tgaagggcat cgacttcaag     780
gaggacggca acatcctggg gcacaagctg gagtacaacc tgccggacca actgactgaa     840
gagcagatcg cagaatttaa agaggctttc tccctatttg acaaggacgg ggatgggaca     900
ataacaacca aggagctggg gacggtgatg cggtctctcg acagaacccc cacagaagca     960
gagctgcagg acatgatcaa tgaagtagat gccgacggtg acggcacaat cgacttccct    1020
gagttcctga caatgatggc aagaaaaatg aaatacaggg gacacgaaga gaaaattaga    1080
gaagcgttcg gtgtgtttga taaggatggc aatggctaca tcagtgcagc agagcttcgc    1140
cacgtgatga caaaccttgg agagaagtta acagatgaag aggttgatga aatgatcagg    1200
gaagcagaca tcgatgggga tggtcaggta aactacgaag agtttgtaca aatgatgaca    1260
gcgaagtaa                                                           1269
```

<210> SEQ ID NO 9
<211> LENGTH: 422
<212> TYPE: PRT
<213> ORGANISM: Artificial
<220> FEATURE:
<223> OTHER INFORMATION: Synthetically-generated construct

<400> SEQUENCE: 9

Met His His His His His His Thr Arg Arg Lys Lys Thr Phe Lys Glu
1               5                   10                  15

Val Ala Thr Ala Val Lys Ile Ile Ala Arg Leu Met Gly Leu Lys Ile
            20                  25                  30

Asn Val Tyr Ile Lys Ala Asp Lys Gln Lys Asn Gly Ile Lys Ala Asn
        35                  40                  45

Phe His Ile Arg His Asn Ile Glu Asp Gly Gly Val Gln Leu Ala Tyr

```
            50                  55                  60
His Tyr Gln Gln Asn Thr Pro Ile Gly Asp Gly Pro Val Leu Leu Pro
 65                  70                  75                  80

Asp Asn His Tyr Leu Ser Val Glu Ser Lys Leu Ser Lys Asp Pro Asn
                 85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
            115                 120                 125

Met Val Ser Lys Gly Glu Glu Leu Phe Thr Gly Val Val Pro Ile Leu
        130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Met Ala Arg Lys Met Lys Tyr
            340                 345                 350

Arg Asp Thr Glu Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
    370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Ser Thr Ala Lys
            420
```

<210> SEQ ID NO 10
<211> LENGTH: 1269
<212> TYPE: DNA
<213> ORGANISM: Artificial
<220> FEATURE:
<223> OTHER INFORMATION: Synthetically-generated construct -continued

```
<400> SEQUENCE: 10
atgcatcatc accatcatca cacgcgtcgc aagaagacct tcaaggaggt ggccaccgcc        60
gtgaagatca tcgcccgcct gatgggcctg aagatcaacg tctatatcaa ggccgacaag       120
cagaagaacg gcatcaaggc gaacttccac atccgccaca acatcgagga cggcggcgtg       180
cagctcgcct accactacca gcagaacacc cccatcggcg acggcccgt gctgctgccc        240
gacaaccact acctgagcgt ggagtccaaa ctttcgaaag accccaacga gaagcgcgat       300
cacatggtcc tgctggagtt cgtgaccgcc gccgggatca ctctcggcat ggacgagctg       360
tacaagggcg gtaccggagg gagcatggtg agcaagggcg aggagctgtt caccggggtg       420
gtgcccatcc tggtcgagct ggacggcgac gtaaacggcc acaagttcag cgtgtccggc       480
gagggtgagg gcgatgccac ctacggcaag ctgaccctga gttcatctg caccaccggc        540
aagctgcccg tgccctggcc caccctcgtg accaccctga cctacggcgt gcagtgcttc       600
agccgctacc ccgaccacat gaagcagcac gacttcttca gtccgccat gcccgaaggc        660
tacatccagg agcgcaccat cttcttcaag gacgacggca actacaagac ccgcgccgag       720
gtgaagttcg agggcgacac cctggtgaac cgcatcgagc tgaagggcat cgacttcaag       780
gaggacggca acatcctggg gcacaagctg gagtacaacc tgccggacca actgactgaa       840
gagcagatcg cagaatttaa agaggctttc tccctatttg acaaggacgg ggatgggaca       900
ataacaacca aggagctggg gacggtgatg cggtctctcg gacagaaccc cacagaagca       960
gagctgcagg acatgatcaa tgaagtagat gccgacggtg acggcacaat cgacttccct      1020
gagttcctga caatgatggc aagaaaaatg aaatacaggg gacacgaaga agaaaattaga     1080
gaagcgttcg gtgtgtttga taaggatggc aatggctaca tcagtgcagc agagcttcgc     1140
cacgtgatga caaaccttgg agagaagtta acagatgaag aggttgatga aatgatcagg     1200
gaagcagaca tcgatgggga tggtcaggta aactacgaag agtttgtaca aatgagcaca     1260
gcgaagtaa                                                             1269

<210> SEQ ID NO 11
<211> LENGTH: 422
<212> TYPE: PRT
<213> ORGANISM: Artificial
<220> FEATURE:
<223> OTHER INFORMATION: Synthetically-generated construct

<400> SEQUENCE: 11

Met His His His His His His Thr Arg Arg Lys Lys Thr Phe Lys Glu
1               5                   10                  15

Val Ala Asn Ala Val Lys Ile Ser Ala Arg Leu Ser Gly Leu Lys Ile
                20                  25                  30

Asn Val Tyr Ile Lys Ala Asp Lys Gln Lys Asn Gly Ile Lys Ala Asn
            35                  40                  45

Phe His Ile Arg His Asn Ile Glu Asp Gly Gly Val Gln Leu Ala Tyr
        50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125
```

Met Val Ser Lys Gly Glu Glu Leu Phe Thr Gly Val Val Pro Ile Leu
130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
            165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
            245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
            325                 330                 335

Ile Asp Phe Pro Glu Phe Leu Thr Met Met Ala Arg Lys Met Lys Tyr
            340                 345                 350

Arg Asp Thr Glu Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
            405                 410                 415

Gln Met Met Thr Ala Lys
            420

<210> SEQ ID NO 12
<211> LENGTH: 1269
<212> TYPE: DNA
<213> ORGANISM: Artificial
<220> FEATURE:
<223> OTHER INFORMATION: Synthetically-generated construct

<400> SEQUENCE: 12
atgcatcatc accatcatca cacgcgtcgc aagaagacct tcaaggaggt ggccaacgcc      60
gtgaagatct ccgcccgcct gtccggcctg aagatcaacg tctatatcaa ggccgacaag     120
cagaagaacg gcatcaaggc gaacttccac atccgccaca catcgagga cggcggcgtg      180 cagctcgcct accactacca gcagaacacc cccatcggcg acggccccgt gctgctgccc     240
gacaaccact acctgagcgt ggagtccaaa ctttcgaaag accccaacga gaagcgcgat     300
cacatggtcc tgctggagtt cgtgaccgcc gccgggatca ctctcggcat ggacgagctg     360

```
tacaagggcg gtaccggagg gagcatggtg agcaagggcg aggagctgtt caccggggtg      420
gtgcccatcc tggtcgagct ggacggcgac gtaaacggcc acaagttcag cgtgtccggc      480
gagggtgagg gcgatgccac ctacggcaag ctgaccctga agttcatctg caccaccggc      540
aagctgcccg tgcccggcc cacctcgtg accaccctga cctacggcgt gcagtgcttc        600
```

```
tacaagggcg gtaccggagg gagcatggtg agcaagggcg aggagctgtt caccggggtg      420
gtgcccatcc tggtcgagct ggacggcgac gtaaacggcc acaagttcag cgtgtccggc      480
gagggtgagg gcgatgccac ctacggcaag ctgaccctga agttcatctg caccaccggc      540
aagctgcccg tgcccggcc cacctcgtg accaccctga cctacggcgt gcagtgcttc        600
agccgctacc ccgaccacat gaagcagcac gacttcttca gtccgccat gcccgaaggc       660 tacatccagg agcgcaccat cttcttcaag gacgacgga actacaagac ccgcgccgag       720
gtgaagttcg agggcgacac cctggtgaac cgcatcgagc tgaagggcat cgacttcaag      780
gaggacggca acatcctggg cacaagctg gagtacaacc tgccggacca actgactgaa       840
gagcagatcg cagaatttaa agaggctttc tccctatttg acaaggacgg ggatgggaca      900
ataacaacca aggagctggg gacggtgatg cggtctctgg ggcagaaccc cacagaagca      960
gagctgcagg acatgatcaa tgaagtagat gccgacggtg acggcacaat cgacttccct     1020
gagttcctga caatgatggc aagaaaaatg aaatacaggg acacggaaga agaaattaga     1080
gaagcgttcg gtgtgtttga taaggatggc aatggctaca tcagtgcagc agagcttcgc     1140
cacgtgatga caaaccttgg agagaagtta acagatgaag aggttgatga atgatcagg      1200 gaagcagaca tcgatgggga tggtcaggta aactacgaag agtttgtaca atgatgaca      1260 gcgaagtaa                                                              1269
```

<210> SEQ ID NO 13
<211> LENGTH: 422
<212> TYPE: PRT
<213> ORGANISM: Artificial
<220> FEATURE:
<223> OTHER INFORMATION: Synthetically-generated construct

<400> SEQUENCE: 13

Met His His His His His His Thr Arg Arg Lys Lys Thr Phe Lys Glu
1               5                   10                  15

Val Ala Thr Ala Val Lys Ile Ile Ala Arg Leu Met Gly Leu Lys Ile
                20                  25                  30

Asn Val Tyr Ile Lys Ala Asp Lys Gln Lys Asn Gly Ile Lys Ala Asn
            35                  40                  45

Phe His Ile Arg His Asn Ile Glu Asp Gly Gly Val Gln Leu Ala Tyr
        50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125

Met Val Ser Lys Gly Glu Glu Leu Phe Thr Gly Val Val Pro Ile Leu
    130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
            195                 200                 205

Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Gln Ala Arg Lys Met Lys Tyr
            340                 345                 350

Arg Asp Thr Glu Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 14
<211> LENGTH: 1269
<212> TYPE: DNA
<213> ORGANISM: Artificial
<220> FEATURE:
<223> OTHER INFORMATION: Synthetically-generated construct

<400> SEQUENCE: 14
atgcatcatc accatcatca cacgcgtcgc aagaagacct tcaaggaggt ggccaccgcc      60
gtgaagatca tcgcccgcct gatgggcctg aagatcaacg tctatatcaa ggccgacaag     120
cagaagaacg gcatcaaggc gaacttccac atccgccaca acatcgagga cggcggcgtg     180
cagctcgcct accactacca gcagaacacc cccatcggcg acggccccgt gctgctgccc     240
gacaaccact acctgagcgt ggagtccaaa ctttcgaaag accccaacga gaagcgcgat     300
cacatggtcc tgctggagtt cgtgaccgcc gccgggatca ctctcggcat ggacgagctg     360
tacaagggcg gtaccggagg gagcatggtg agcaagggcg aggagctgtt caccggggtg     420
gtgcccatcc tggtcgagct ggacggcgac gtaaacggcc acaagttcag cgtgtccggc     480
gagggtgagg gcgatgccac ctacggcaag ctgaccctga agttcatctg caccaccggc     540
aagctgcccg tgccctggcc caccctcgtg accaccctga cctacggcgt gcagtgcttc     600
agccgctacc ccgaccacat gaagcagcac gacttcttca gtccgccat gcccgaaggc      660 tacatccagg agcgcaccat cttcttcaag gacgacggca ctacaagac ccgcgccgag      720

-continued

```
gtgaagttcg agggcgacac cctggtgaac cgcatcgagc tgaagggcat cgacttcaag    780
gaggacggca acatcctggg gcacaagctg gagtacaacc tgccggacca actgactgaa    840
gagcagatcg cagaattaa agaggctttc tccctatttg acaaggacgg ggatgggaca    900
ataacaacca aggagctggg gacggtgatg cggtctctcg acagaacccc cacagaagca    960
gagctgcagg acatgatcaa tgaagtagat gccgacggtg acggcacaat cgacttccct   1020
gagttcctga caatgcaggc aagaaaaatg aaatacaggg acacggaaga agaaattaga   1080
gaagcgttcg gtgtgtttga taaggatggc aatggctaca tcagtgcagc agagcttcgc   1140
cacgtgatga caaaccttgg agagaagtta acagatgaag aggttgatga aatgatcagg   1200
gaagcagaca tcgatgggga tggtcaggta aactacgaag agtttgtaca aatgatgaca   1260
gcgaagtaa                                                           1269
```

<210> SEQ ID NO 15
<211> LENGTH: 422
<212> TYPE: PRT
<213> ORGANISM: Artificial
<220> FEATURE:
<223> OTHER INFORMATION: Synthetically-generated construct

<400> SEQUENCE: 15

```
Met His His His His His His Thr Arg Arg Lys Lys Thr Phe Lys Glu
1               5                   10                  15

Val Ala Thr Ala Val Lys Ile Ile Ala Arg Leu Met Gly Leu Lys Ile
            20                  25                  30

Asn Val Tyr Ile Lys Ala Asp Lys Gln Lys Asn Gly Ile Lys Ala Asn
        35                  40                  45

Phe His Ile Arg His Asn Ile Glu Asp Gly Gly Val Gln Leu Ala Tyr
    50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125

Met Val Ser Lys Gly Glu Glu Leu Phe Thr Gly Val Val Pro Ile Leu
    130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
```

```
                        260                 265                 270
Asn Leu Pro Asp Gln Leu Thr Glu Glu Gln Ile Ala Glu Tyr Lys Gln
            275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly His Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Met Ala Arg Lys Met Lys Tyr
            340                 345                 350

Arg Asp Thr Glu Glu Glu Ile Arg Glu Ala Phe Gly Val Phe Asp Lys
                355                 360                 365

Asp Gly Asn Gly Tyr Ile Ser Ala Ala Glu Leu Arg His Val Met Thr
            370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 16
<211> LENGTH: 1269
<212> TYPE: DNA
<213> ORGANISM: Artificial
<220> FEATURE:
<223> OTHER INFORMATION: Synthetically-generated construct

<400> SEQUENCE: 16
atgcatcatc accatcatca cacgcgtcgc aagaagacct tcaaggaggt ggccaccgcc      60
gtgaagatca tcgcccgcct gatgggcctg aagatcaacg tctatatcaa ggccgacaag     120
cagaagaacg gcatcaaggc gaacttccac atccgccaca catcgagga cggcggcgtg      180 cagctcgcct accactacca gcagaacacc cccatcggcg acggcccgt gctgctgccc      240 gacaaccact acctgagcgt ggagtccaaa ctttcgaaag accccaacga gaagcgcgat     300
cacatggtcc tgctggagtt cgtgaccgcc gccgggatca ctctcggcat ggacgagctg     360
tacaagggcg gtaccggagg gagcatggtg agcaagggcg aggagctgtt caccggggtg     420
gtgcccatcc tggtcgagct ggacggcgac gtaaacggcc acaagttcag cgtgtccggc     480
gagggtgagg gcgatgccac ctacggcaag ctgaccctga gttcatctg caccaccggc      540 aagctgcccg tgccctggcc cacccttcgtg accaccctga cctacggcgt gcagtgcttc     600
agccgctacc ccgaccacat gaagcagcac gacttcttca gtccgccat gcccgaaggc      660 tacatccagg agcgcaccat cttcttcaag gacgacggca actacaagac ccgcgccgag     720
gtgaagttcg agggcgacac cctggtgaac cgcatcgagc tgaagggcat cgacttcaag     780
gaggacggca acatcctggg gcacaagctg gagtacaacc tgccggacca actgactgaa     840
gagcagatcg cagaatacaa acaagctttc tccctatttg acaaggacgg gatgggaca      900 ataacaacca aggagctggg gacggtgatg cggtctctcg gacacaaccc cacagaagca     960
gagctgcagg acatgatcaa tgaagtagat gccgacggtg acggcacaat cgacttccct    1020
gagttcctga caatgatggc aagaaaaatg aaatacaggg acacggaaga agaaattaga    1080
gaagcgttcg gtgtgtttga taaggatggc aatggctaca tcagtgcagc agagcttcgc    1140
```

```
cacgtgatga caaaccttgg agagaagtta acagatgaag aggttgatga aatgatcagg    1200
gaagcagaca tcgatgggga tggtcaggta aactacgaag agtttgtaca aatgatgaca    1260
gcgaagtaa                                                            1269
```

<210> SEQ ID NO 17
<211> LENGTH: 422
<212> TYPE: PRT
<213> ORGANISM: Artificial
<220> FEATURE:
<223> OTHER INFORMATION: Synthetically-generated construct

<400> SEQUENCE: 17

```
Met His His His His His Thr Arg Arg Lys Lys Thr Phe Lys Glu
1               5                   10                  15

Val Ala Thr Ala Val Lys Ile Ile Ala Arg Leu Met Gly Leu Lys Ile
                20                  25                  30

Asn Val Tyr Ile Lys Ala Asp Lys Gln Lys Asn Gly Ile Lys Ala Asn
            35                  40                  45

Phe His Ile Arg His Asn Ile Glu Asp Gly Gly Val Gln Leu Ala Tyr
        50                  55                  60

His Tyr Gln Gln Asn Thr Pro Ile Gly Asp Gly Pro Val Leu Leu Pro
65                  70                  75                  80

Asp Asn His Tyr Leu Ser Val Glu Ser Lys Leu Ser Lys Asp Pro Asn
                85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
        115                 120                 125

Met Val Ser Lys Gly Glu Glu Leu Phe Thr Gly Val Val Pro Ile Leu
130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
        195                 200                 205

Gln His Asp Phe Phe Lys Ser Ala Met Pro Glu Gly Tyr Ile Gln Glu
    210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Lys Asn Pro Thr Glu Ala
305                 310                 315                 320

Glu Leu Gln Asp Met Ile Asn Glu Val Asp Ala Asp Gly Asp Gly Thr
                325                 330                 335
```

Ile Asp Phe Pro Glu Phe Leu Thr Met Met Ala Arg Lys Met Lys Tyr
            340                 345                 350

Arg Asp Thr Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 18
<211> LENGTH: 1269
<212> TYPE: DNA
<213> ORGANISM: Artificial
<220> FEATURE:
<223> OTHER INFORMATION: Synthetically-generated construct

<400> SEQUENCE: 18
atgcatcatc accatcatca cacgcgtcgc aagaagacct tcaaggaggt ggccaccgcc        60
gtgaagatca tcgcccgcct gatgggcctg aagatcaacg tctatatcaa ggccgacaag       120
cagaagaacg gcatcaaggc gaacttccac atccgccaca catcgagga cggcggcgtg        180 cagctcgcct accactacca gcagaacacc cccatcggcg acggcccgt gctgctgccc        240 gacaaccact acctgagcgt ggagtccaaa ctttcgaaag accccaacga aagcgcgat        300 cacatggtcc tgctggagtt cgtgaccgcc gccgggatca ctctcggcat ggacgagctg       360
tacaagggcg gtaccggagg gagcatggtg agcaagggcg aggagctgtt caccggggtg       420
gtgcccatcc tggtcgagct ggacggcgac gtaaacggcc acaagttcag cgtgtccggc       480
gagggtgagg gcgatgccac ctacggcaag ctgaccctga gttcatctg caccaccggc        540 aagctgcccg tgccctggcc caccctcgtg accaccctga cctacggcgt gcagtgcttc       600
agccgctacc ccgaccacat gaagcagcac gacttcttca gtccgccat gcccgaaggc        660 tacatccagg agcgcaccat cttcttcaag gacgacggca actacaagac ccgcgccgag       720
gtgaagttcg agggcgacac cctggtgaac cgcatcgagc tgaagggcat cgacttcaag       780
gaggacggca acatcctggg gcacaagctg gagtacaacc tgccggacca actgactgaa       840
gagcagatcg cagaatttaa agaggctttc tccctatttg acaaggacgg ggatgggaca       900
ataacaacca aggagctggg gacggtgatg cggtctctcg aaagaacccc cacagaagca       960
gagctgcagg acatgatcaa tgaagtagat gccgacggtg acggcacaat cgacttccct      1020
gagttcctga caatgatggc aagaaaaatg aaatacaggg acacggaaga agaaattaga      1080
gaagcgttcg gtgtgtttga taaggatggc aatggctaca tcagtgcagc agagcttcgc      1140
cacgtgatga caaaccttgg agagaagtta acagatgaag aggttgatga atgatcagg       1200 gaagcagaca tcgatgggga tggtcaggta aactacgaag agtttgtaca aatgatgaca      1260
gcgaagtaa                                                              1269

<210> SEQ ID NO 19
<211> LENGTH: 421
<212> TYPE: PRT
<213> ORGANISM: Artificial
<220> FEATURE:

<223> OTHER INFORMATION: Synthetically-generated construct

<400> SEQUENCE: 19

```
Met His His His His His Thr Arg Arg Lys Lys Thr Phe Lys Glu
1               5                   10                  15

Val Ala Asn Ala Val Lys Ile Ser Ala Ser Leu Met Gly Leu Glu Asn
            20                  25                  30

Val Tyr Ile Lys Ala Asp Lys Gln Lys Asn Gly Ile Lys Ala Asn Phe
            35                  40                  45

His Ile Arg His Asn Ile Glu Asp Gly Gly Val Gln Leu Ala Tyr His
        50                  55                  60

Tyr Gln Gln Asn Thr Pro Ile Gly Asp Gly Pro Val Leu Leu Pro Asp
65                  70                  75                  80

Asn His Tyr Leu Ser Val Gln Ser Lys Leu Ser Lys Asp Pro Asn Glu
                85                  90                  95

Lys Arg Asp His Met Val Leu Leu Glu Phe Val Thr Ala Ala Gly Ile
            100                 105                 110

Thr Leu Gly Met Asp Glu Leu Tyr Lys Gly Gly Thr Gly Gly Ser Met
        115                 120                 125

Val Ser Lys Gly Glu Glu Leu Phe Thr Gly Val Val Pro Ile Leu Val
    130                 135                 140

Glu Leu Asp Gly Asp Val Asn Gly His Lys Phe Ser Val Ser Gly Glu
145                 150                 155                 160

Gly Glu Gly Asp Ala Thr Tyr Gly Lys Leu Thr Leu Lys Phe Ile Cys
                165                 170                 175

Thr Thr Gly Lys Leu Pro Val Pro Trp Pro Thr Leu Val Thr Thr Leu
            180                 185                 190

Thr Tyr Gly Val Gln Cys Phe Ser Arg Tyr Pro Asp His Met Lys Gln
        195                 200                 205

His Asp Phe Phe Lys Ser Ala Met Pro Glu Gly Tyr Ile Gln Glu Arg
    210                 215                 220

Thr Ile Phe Phe Lys Asp Asp Gly Asn Tyr Lys Thr Arg Ala Glu Val
225                 230                 235                 240

Lys Phe Glu Gly Asp Thr Leu Val Asn Arg Ile Glu Leu Lys Gly Ile
                245                 250                 255

Asp Phe Lys Glu Asp Gly Asn Ile Leu Gly His Lys Leu Glu Tyr Asn
            260                 265                 270

Leu Pro Asp Gln Leu Thr Glu Glu Gln Ile Ala Glu Phe Lys Glu Ala
        275                 280                 285

Phe Ser Leu Phe Asp Lys Asp Gly Asp Gly Thr Ile Thr Thr Lys Glu
    290                 295                 300

Leu Gly Thr Val Met Arg Ser Leu Gly Gln Asn Pro Thr Glu Ala Glu
305                 310                 315                 320

Leu Gln Asp Met Ile Asn Glu Val Asp Ala Asp Gly Asp Gly Thr Ile
                325                 330                 335

Asp Phe Pro Glu Phe Leu Thr Met Met Ala Arg Lys Met Lys Tyr Arg
            340                 345                 350

Asp Thr Glu Glu Glu Ile Arg Glu Ala Phe Gly Val Phe Asp Lys Asp
        355                 360                 365

Gly Asn Gly Tyr Ile Ser Ala Ala Glu Leu Arg His Val Met Thr Asn
    370                 375                 380

Leu Gly Glu Lys Leu Thr Asp Glu Glu Val Asp Glu Met Ile Arg Glu
385                 390                 395                 400
```

Ala Asp Ile Asp Gly Asp Gly Gln Val Asn Tyr Glu Glu Phe Val Gln
            405                 410                 415

Met Met Thr Ala Lys
            420

<210> SEQ ID NO 20
<211> LENGTH: 1266
<212> TYPE: DNA
<213> ORGANISM: Artificial
<220> FEATURE:
<223> OTHER INFORMATION: Synthetically-generated construct

<400> SEQUENCE: 20

| | | |
|---|---|---|
| atgcatcatc accatcatca cacgcgtcgc aagaagacct tcaaggaggt ggccaacgcc | 60 |
| gtgaagatct ccgcctccct gatgggcctc gagaacgtct atatcaaggc cgacaagcag | 120 |
| aagaacggca tcaaggcgaa cttccacatc cgccacaaca tcgaggacgg cggcgtgcag | 180 |
| ctcgcctacc actaccagca gaacaccccc atcggcgacg ccccgtgct gctgcccgac | 240 |
| aaccactacc tgagcgtgca gtccaaactt tcgaaagacc caacgagaa gcgcgatcac | 300 |
| atggtcctgc tggagttcgt gaccgccgcc gggatcactc tcggcatgga cgagctgtac | 360 |
| aagggcggta ccggagggag catggtgagc aagggcgagg agctgttcac cggggtggtg | 420 |
| cccatcctgg tcgagctgga cggcgacgta acggccaca agttcagcgt gtccggcgag | 480 |
| ggtgagggcg atgccaccta cggcaagctg accctgaagt tcatctgcac caccggcaag | 540 |
| ctgcccgtgc cctggcccac cctcgtgacc accctgacct acggcgtgca gtgcttcagc | 600 |
| cgctaccccg accacatgaa gcagcacgac ttcttcaagt ccgccatgcc cgaaggctac | 660 |
| atccaggagc gcaccatctt cttcaaggac gacggcaact acaagacccg cgccgaggtg | 720 |
| aagttcgagg gcgacaccct ggtgaaccgc atcgagctga agggcatcga cttcaaggag | 780 |
| gacggcaaca tcctggggca caagctggag tacaacctgc cggaccaact gactgaagag | 840 |
| cagatcgcag aatttaaaga ggctttctcc ctatttgaca aggacgggga tgggacaata | 900 |
| acaaccaagg agctggggac ggtgatgcgg tctctggggc agaaccccac agaagcagag | 960 |
| ctgcaggaca tgatcaatga agtagatgcc gacggtgacg gcacaatcga cttccctgag | 1020 |
| ttcctgacaa tgatggcaag aaaaatgaaa tacagggaca cggaagaaga aattagagaa | 1080 |
| gcgttcggtg tgtttgataa ggatggcaat ggctacatca gtgcagcaga gcttcgccac | 1140 |
| gtgatgacaa accttggaga gaagttaaca gatgaagagg ttgatgaaat gatcaggaa | 1200 |
| gcagacatcg atggggatgg tcaggtaaac tacgaagagt ttgtacaaat gatgacagcg | 1260 |
| aagtaa | 1266 |

<210> SEQ ID NO 21
<211> LENGTH: 422
<212> TYPE: PRT
<213> ORGANISM: Artificial
<220> FEATURE:
<223> OTHER INFORMATION: Synthetically-generated construct

<400> SEQUENCE: 21

Met His His His His His His Thr Arg Arg Lys Lys Thr Phe Lys Glu
1               5                   10                  15

Val Ala Asn Ala Val Lys Ile Ser Ala Ser Leu Met Gly Leu Lys Ile
            20                  25                  30

Asn Val Tyr Ile Lys Ala Asp Lys Gln Lys Asn Gly Ile Lys Ala Asn
        35                  40                  45

Phe His Ile Arg His Asn Ile Glu Asp Gly Gly Val Gln Leu Ala Tyr
 50                  55                  60

His Tyr Gln Gln Asn Thr Pro Ile Gly Asp Gly Pro Val Leu Leu Pro
 65                  70                  75                  80

Asp Asn His Tyr Leu Ser Val Gln Ser Lys Leu Ser Lys Asp Pro Asn
                 85                  90                  95

Glu Lys Arg Asp His Met Val Leu Leu Glu Phe Val Thr Ala Ala Gly
            100                 105                 110

Ile Thr Leu Gly Met Asp Glu Leu Tyr Lys Gly Gly Thr Gly Gly Ser
            115                 120                 125

Met Val Ser Lys Gly Glu Glu Leu Phe Thr Gly Val Val Pro Ile Leu
130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
            180                 185                 190

Leu Thr Tyr Gly Val Gln Cys Phe Ser Arg Tyr Pro Asp His Met Lys
            195                 200                 205

Gln His Asp Phe Phe Lys Ser Ala Met Pro Glu Gly Tyr Ile Gln Glu
        210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
            260                 265                 270

Asn Leu Pro Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
                325                 330                 335

Ile Asp Phe Pro Glu Phe Leu Thr Met Met Ala Arg Lys Met Lys Tyr
            340                 345                 350

Arg Asp Thr Glu Glu Glu Ile Arg Glu Ala Phe Gly Val Phe Asp Lys
        355                 360                 365

Asp Gly Asn Gly Tyr Ile Ser Ala Ala Glu Leu Arg His Val Met Thr
    370                 375                 380

Asn Leu Gly Glu Lys Leu Thr Asp Glu Glu Val Asp Glu Met Ile Arg
385                 390                 395                 400

Glu Ala Asp Ile Asp Gly Asp Gly Gln Val Asn Tyr Glu Glu Phe Val
                405                 410                 415

Gln Met Met Thr Ala Lys
            420

<210> SEQ ID NO 22
<211> LENGTH: 1269
<212> TYPE: DNA
<213> ORGANISM: Artificial
<220> FEATURE:
<223> OTHER INFORMATION: Synthetically-generated construct

<400> SEQUENCE: 22

```
atgcatcatc accatcatca cacgcgtcgc aagaagacct tcaaggaggt ggccaacgcc      60
gtgaagatct ccgcctctct gatgggcctg aagatcaacg tctatatcaa ggccgacaag     120
cagaagaacg gcatcaaggc gaacttccac atccgccaca acatcgagga cggcggcgtg     180
cagctcgcct accactacca gcagaacacc cccatcggcg acggcccgt gctgctgccc      240
gacaaccact acctgagcgt gcagtccaaa ctttcgaaag accccaacga gaagcgcgat     300
cacatggtcc tgctggagtt cgtgaccgcc gccgggatca ctctcggcat ggacgagctg     360
tacaagggcg gtaccggagg gagcatggtg agcaagggcg aggagctgtt caccggggtg     420
gtgcccatcc tggtcgagct ggacggcgac gtaaacggcc acaagttcag cgtgtccggc     480
gagggtgagg gcgatgccac ctacggcaag ctgaccctga agttcatctg caccaccggc     540
aagctgcccg tgccctggcc caccctcgtg accaccctga cctacggcgt gcagtgcttc     600
agccgctacc ccgaccacat gaagcagcac gacttcttca gtccgccat gcccgaaggc      660
tacatccagg agcgcaccat cttcttcaag gacgacggca actacaagac ccgcgccgag     720
gtgaagttcg agggcgacac cctggtgaac cgcatcgagc tgaagggcat cgacttcaag     780
gaggacggca acatcctggg gcacaagctg gagtacaacc tgccggacca actgactgaa     840
gagcagatcg cagaatttaa agaggctttc tccctatttg acaaggacgg ggatgggaca     900
ataacaacca aggagctggg gacggtgatg cggtctctgg ggcagaaccc cacagaagca     960
gagctgcagg acatgatcaa tgaagtagat gccgacggtg acggcacaat cgacttccct    1020
gagttcctga caatgatggc aagaaaaatg aaatacaggg acacggaaga gaaaattaga    1080
gaagcgttcg gtgtgtttga taaggatggc aatggctaca tcagtgcagc agagcttcgc    1140
cacgtgatga caaaccttgg agagaagtta acagatgaag aggttgatga atgatcagg    1200
gaagcagaca tcgatgggga tggtcaggta aactacgaag agtttgtaca atgatgaca    1260
gcgaagtaa                                                           1269
```

<210> SEQ ID NO 23
<211> LENGTH: 450
<212> TYPE: PRT
<213> ORGANISM: Artificial
<220> FEATURE:
<223> OTHER INFORMATION: Synthetically-generated construct

<400> SEQUENCE: 23

```
Met Gly Ser His His His His His Gly Met Ala Ser Met Thr Gly
1               5                   10                  15

Gly Gln Gln Met Gly Arg Asp Leu Tyr Asp Asp Asp Lys Asp Leu
                20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
```

```
              115                 120                 125
His Met Val Leu Leu Glu Phe Val Thr Ala Ala Gly Ile Thr Leu Gly
    130                 135                 140
Met Asp Glu Leu Tyr Lys Gly Gly Thr Gly Gly Ser Met Val Ser Lys
145                 150                 155                 160
Gly Glu Glu Leu Phe Thr Gly Val Val Pro Ile Leu Val Glu Leu Asp
                165                 170                 175
Gly Asp Val Asn Gly His Lys Phe Ser Val Ser Gly Glu Gly Glu Gly
            180                 185                 190
Asp Ala Thr Tyr Gly Lys Leu Thr Leu Lys Phe Ile Cys Thr Thr Gly
        195                 200                 205
Lys Leu Pro Val Pro Trp Pro Thr Leu Val Thr Thr Leu Thr Tyr Gly
    210                 215                 220
Val Gln Cys Phe Ser Arg Tyr Pro Asp His Met Lys Gln His Asp Phe
225                 230                 235                 240
Phe Lys Ser Ala Met Pro Glu Gly Tyr Ile Gln Glu Arg Thr Ile Phe
                245                 250                 255
Phe Lys Asp Asp Gly Asn Tyr Lys Thr Arg Ala Glu Val Lys Phe Glu
            260                 265                 270
Gly Asp Thr Leu Val Asn Arg Ile Glu Leu Lys Gly Ile Asp Phe Lys
        275                 280                 285
Glu Asp Gly Asn Ile Leu Gly His Lys Leu Glu Tyr Asn Leu Pro Asp
    290                 295                 300
Gln Leu Thr Glu Glu Gln Ile Ala Glu Phe Lys Glu Leu Phe Ser Leu
305                 310                 315                 320
Phe Asp Lys Asp Gly Asp Gly Thr Ile Thr Thr Lys Glu Leu Gly Thr
                325                 330                 335
Val Met Arg Ser Leu Gly Gln Asn Pro Thr Glu Ala Glu Leu Gln Asp
            340                 345                 350
Met Ile Asn Glu Val Asp Ala Asp Gly Asp Gly Thr Ile Asp Phe Pro
        355                 360                 365
Glu Phe Leu Thr Met Met Ala Arg Lys Met Lys Tyr Thr Asp Ser Glu
    370                 375                 380
Glu Glu Ile Arg Glu Ala Phe Arg Val Phe Asp Lys Asp Gly Asn Gly
385                 390                 395                 400
Tyr Ile Ser Ala Ala Glu Leu Arg His Val Met Thr Asn Leu Gly Glu
                405                 410                 415
Lys Leu Thr Asp Glu Glu Val Asp Glu Met Ile Arg Glu Ala Asp Ile
            420                 425                 430
Asp Gly Asp Gly Gln Val Asn Tyr Glu Glu Phe Val Gln Met Met Thr
        435                 440                 445
Ala Lys
    450

<210> SEQ ID NO 24
<211> LENGTH: 1353
<212> TYPE: DNA
<213> ORGANISM: Artificial
<220> FEATURE:
<223> OTHER INFORMATION: Synthetically-generated construct

<400> SEQUENCE: 24
atgggttctc atcatcatca tcatcatggt atgctagca tgactggtgg acagcaaatg      60
ggtcgggatc tgtacgacga tgacgataag gatctcgcca ccatggtcga ctcatcacgt     120
```

| | |
|---|---|
| cgtaagtgga ataagacagg tcacgcagtc agagctatag gtcggctgag ctcactcgag | 180 |
| aacgtctata tcaaggccga caagcagaag aacggcatca aggcgaactt caagatccgc | 240 |
| cacaacatcg aggacggcgg cgtgcagctc gcctaccact accagcagaa cacccccatc | 300 |
| ggcgacggcc ccgtgctgct gcccgacaac cactacctga gcgtgcagtc caaactttcg | 360 |
| aaagacccca acgagaagcg cgatcacatg gtcctgctgg agttcgtgac cgccgccggg | 420 |
| atcactctcg gcatggacga gctgtacaag gcggtaccg agggagcat ggtgagcaag | 480 |
| ggcgaggagc tgttcaccgg ggtggtgccc atcctggtcg agctggacgg cgacgtaaac | 540 |
| ggccacaagt tcagcgtgtc cggcgagggt gagggcgatg ccacctacgg caagctgacc | 600 |
| ctgaagttca tctgcaccac cggcaagctg cccgtgccct ggcccaccct cgtgaccacc | 660 |
| ctgacctacg gcgtgcagtg cttcagccgc taccccgacc acatgaagca gcacgacttc | 720 |
| ttcaagtccg ccatgcccga aggctacatc caggagcgca ccatcttctt caaggacgac | 780 |
| ggcaactaca agacccgcgc cgaggtgaag ttcgagggcg acaccctggt gaaccgcatc | 840 |
| gagcttaagg gcatcgactt caaggaggac ggcaacatcc tggggcacaa gctggagtac | 900 |
| aacctgccgg accaactgac tgaagagcag atcgcagaat taaagagct gttctcccta | 960 |
| tttgacaagg acgggatgg gacaataaca accaaggagc tggggacggt gatgcggtct | 1020 |
| ctggggcaga accccacaga agcagagctg caggacatga tcaatgaagt agatgccgac | 1080 |
| ggtgacggca caatcgactt ccctgagttc ctgacaatga tggcaagaaa atgaaaatac | 1140 |
| acagacagtg aagaagaaat tagagaagcg ttccgtgtgt ttgataagga tggcaatggc | 1200 |
| tacatcagtg cagcagagct tcgccacgtg atgacaaacc ttggagagaa gttaacagat | 1260 |
| gaagaggttg atgaaatgat cagggaagca gacatcgatg gggatggtca ggtaaactac | 1320 |
| gaagagtttg tacaaatgat gacagcgaag taa | 1353 |

<210> SEQ ID NO 25
<211> LENGTH: 20
<212> TYPE: PRT
<213> ORGANISM: Artificial
<220> FEATURE:
<223> OTHER INFORMATION: Synthetically-generated peptide

<400> SEQUENCE: 25

Ala Arg Arg Lys Trp Gln Lys Thr Gly His Ala Val Arg Ala Ile Gly
1               5                   10                  15

Arg Leu Ser Ser
            20

<210> SEQ ID NO 26
<211> LENGTH: 25
<212> TYPE: PRT
<213> ORGANISM: Artificial
<220> FEATURE:
<223> OTHER INFORMATION: Synthetically-generated peptide

<400> SEQUENCE: 26

Leu Lys Lys Phe Asn Ala Arg Arg Lys Leu Lys Gly Ala Ile Leu Thr
1               5                   10                  15

Thr Met Leu Ala Thr Arg Asn Phe Ser
            20                  25

<210> SEQ ID NO 27
<211> LENGTH: 27
<212> TYPE: PRT
<213> ORGANISM: Artificial

<220> FEATURE:
<223> OTHER INFORMATION: Synthetically-generated peptide

<400> SEQUENCE: 27

Val Arg Val Ile Pro Arg Leu Asp Thr Leu Ile Leu Val Lys Ala Met
1               5                   10                  15

Gly His Arg Lys Arg Phe Gly Asn Pro Phe Arg
            20                  25

<210> SEQ ID NO 28
<211> LENGTH: 19
<212> TYPE: PRT
<213> ORGANISM: Artificial
<220> FEATURE:
<223> OTHER INFORMATION: Synthetically-generated peptide

<400> SEQUENCE: 28

Lys Lys Arg Phe Ser Phe Lys Lys Ser Phe Lys Leu Ser Gly Phe Ser
1               5                   10                  15

Phe Lys Lys

<210> SEQ ID NO 29
<211> LENGTH: 20
<212> TYPE: PRT
<213> ORGANISM: Artificial
<220> FEATURE:
<223> OTHER INFORMATION: Synthetically-generated peptide

<400> SEQUENCE: 29

Arg Lys Lys Thr Phe Lys Glu Val Ala Asn Ala Val Lys Ile Ser Ala
1               5                   10                  15

Ser Leu Met Gly
            20

<210> SEQ ID NO 30
<211> LENGTH: 19
<212> TYPE: PRT
<213> ORGANISM: Artificial
<220> FEATURE:
<223> OTHER INFORMATION: Synthetically-generated peptide

<400> SEQUENCE: 30

Gly Gly Phe Arg Arg Ile Ala Arg Leu Val Gly Val Leu Arg Glu Trp
1               5                   10                  15

Ala Tyr Arg

<210> SEQ ID NO 31
<211> LENGTH: 19
<212> TYPE: PRT
<213> ORGANISM: Artificial
<220> FEATURE:
<223> OTHER INFORMATION: Synthetically-generated peptide

<400> SEQUENCE: 31

Arg Lys Lys Trp Lys Gln Ser Val Arg Leu Ile Ser Leu Cys Gln Arg
1               5                   10                  15

Leu Ser Arg

<210> SEQ ID NO 32
<211> LENGTH: 25
<212> TYPE: PRT
<213> ORGANISM: Artificial
<220> FEATURE:
<223> OTHER INFORMATION: Synthetically-generated peptide

```
<400> SEQUENCE: 32

Lys Ser Lys Lys Ala Val Trp His Lys Leu Leu Ser Lys Gln Arg Arg
1               5                   10                  15

Arg Ala Val Val Ala Cys Phe Arg Met
            20                  25

<210> SEQ ID NO 33
<211> LENGTH: 17
<212> TYPE: PRT
<213> ORGANISM: Artificial
<220> FEATURE:
<223> OTHER INFORMATION: Synthetically-generated peptide

<400> SEQUENCE: 33

Lys Phe Tyr Ala Thr Phe Leu Ile Gln Glu Tyr Phe Arg Lys Phe Lys
1               5                   10                  15

Lys

<210> SEQ ID NO 34
<211> LENGTH: 25
<212> TYPE: PRT
<213> ORGANISM: Artificial
<220> FEATURE:
<223> OTHER INFORMATION: Synthetically-generated peptide

<400> SEQUENCE: 34

Ala Ser Ala Ser Pro Trp Lys Ser Ala Arg Leu Met Val His Thr Val
1               5                   10                  15

Ala Thr Phe Asn Ser Ile Lys Glu Arg
            20                  25

<210> SEQ ID NO 35
<211> LENGTH: 19
<212> TYPE: PRT
<213> ORGANISM: Artificial
<220> FEATURE:
<223> OTHER INFORMATION: Synthetically-generated peptide

<400> SEQUENCE: 35

Lys Lys Lys Ala Thr Phe Arg Ala Ile Thr Ser Thr Leu Ala Ser Ser
1               5                   10                  15

Phe Lys Arg

<210> SEQ ID NO 36
<211> LENGTH: 27
<212> TYPE: PRT
<213> ORGANISM: Artificial
<220> FEATURE:
<223> OTHER INFORMATION: Synthetically-generated peptide

<400> SEQUENCE: 36

Leu Arg Arg Gly Gln Ile Leu Trp Phe Arg Gly Leu Asn Arg Ile Gln
1               5                   10                  15

Thr Gln Ile Lys Val Val Lys Ala Phe His Ser
            20                  25

<210> SEQ ID NO 37
<211> LENGTH: 15
<212> TYPE: PRT
<213> ORGANISM: Artificial
<220> FEATURE:
<223> OTHER INFORMATION: Synthetically-generated peptide
```

-continued

```
<400> SEQUENCE: 37

Ala Phe Ile Ile Trp Leu Ala Arg Arg Leu Lys Lys Gly Lys Lys
1               5                   10                  15

<210> SEQ ID NO 38
<211> LENGTH: 19
<212> TYPE: PRT
<213> ORGANISM: Artificial
<220> FEATURE:
<223> OTHER INFORMATION: Synthetically-generated peptide

<400> SEQUENCE: 38

Met Asp Val Phe Met Lys Gly Leu Ser Lys Ala Lys Glu Gly Val Val
1               5                   10                  15

Ala Ala Ala

<210> SEQ ID NO 39
<211> LENGTH: 16
<212> TYPE: PRT
<213> ORGANISM: Artificial
<220> FEATURE:
<223> OTHER INFORMATION: Synthetically-generated peptide

<400> SEQUENCE: 39

Met Asp Cys Leu Cys Ile Val Thr Thr Lys Lys Tyr Arg Tyr Gln Asp
1               5                   10                  15

<210> SEQ ID NO 40
<211> LENGTH: 19
<212> TYPE: PRT
<213> ORGANISM: Artificial
<220> FEATURE:
<223> OTHER INFORMATION: Synthetically-generated peptide

<400> SEQUENCE: 40

Ala Ala Gly Ser Gly Trp Arg Lys Ile Lys Leu Ala Val Arg Gly Ala
1               5                   10                  15

Gln Ala Lys

<210> SEQ ID NO 41
<211> LENGTH: 22
<212> TYPE: PRT
<213> ORGANISM: Artificial
<220> FEATURE:
<223> OTHER INFORMATION: Synthetically-generated peptide

<400> SEQUENCE: 41

Lys Arg Arg Ala Ile Gly Phe Lys Lys Leu Ala Glu Ala Val Lys Phe
1               5                   10                  15

Ser Ala Lys Leu Met Gly
                20

<210> SEQ ID NO 42
<211> LENGTH: 21
<212> TYPE: PRT
<213> ORGANISM: Artificial
<220> FEATURE:
<223> OTHER INFORMATION: Synthetically-generated peptide

<400> SEQUENCE: 42

Lys Phe Tyr Ala Thr Phe Leu Ile Gln Glu His Phe Arg Lys Phe Met
1               5                   10                  15

Lys Arg Gln Glu Glu
                20
```

```
<210> SEQ ID NO 43
<211> LENGTH: 21
<212> TYPE: PRT
<213> ORGANISM: Artificial
<220> FEATURE:
<223> OTHER INFORMATION: Synthetically-generated peptide

<400> SEQUENCE: 43

Lys Ile Tyr Ala Ala Met Met Ile Met Glu Tyr Tyr Arg Gln Ser Lys
1               5                   10                  15

Ala Lys Lys Leu Gln
            20

<210> SEQ ID NO 44
<211> LENGTH: 16
<212> TYPE: PRT
<213> ORGANISM: Artificial
<220> FEATURE:
<223> OTHER INFORMATION: Synthetically-generated peptide

<400> SEQUENCE: 44

Ser Lys Tyr Ile Thr Thr Ile Ala Gly Val Met Thr Leu Ser Gln Val
1               5                   10                  15

<210> SEQ ID NO 45
<211> LENGTH: 18
<212> TYPE: PRT
<213> ORGANISM: Artificial
<220> FEATURE:
<223> OTHER INFORMATION: Synthetically-generated peptide

<400> SEQUENCE: 45

Arg Arg Arg Glu Ile Arg Phe Arg Val Leu Val Lys Val Val Phe Phe
1               5                   10                  15

Ser Ser

<210> SEQ ID NO 46
<211> LENGTH: 21
<212> TYPE: PRT
<213> ORGANISM: Artificial
<220> FEATURE:
<223> OTHER INFORMATION: Synthetically-generated peptide

<400> SEQUENCE: 46

Ser Phe Asn Ala Arg Arg Lys Leu Lys Gly Ala Ile Leu Thr Thr Met
1               5                   10                  15

Leu Ala Thr Ala Ser
            20

<210> SEQ ID NO 47
<211> LENGTH: 21
<212> TYPE: PRT
<213> ORGANISM: Artificial
<220> FEATURE:
<223> OTHER INFORMATION: Synthetically-generated peptide

<400> SEQUENCE: 47

Gly Arg Val Ser Gly Arg Asn Trp Lys Asn Phe Ala Leu Val Pro Leu
1               5                   10                  15

Leu Arg Asp Ala Ser
            20

<210> SEQ ID NO 48
```

```
<211> LENGTH: 21
<212> TYPE: PRT
<213> ORGANISM: Artificial
<220> FEATURE:
<223> OTHER INFORMATION: Synthetically-generated peptide

<400> SEQUENCE: 48

Glu Arg Leu Gln Gln Trp Arg Lys Ala Ala Leu Val Leu Asn Ala Ser
1               5                   10                  15

Arg Arg Phe Arg Tyr
            20

<210> SEQ ID NO 49
<211> LENGTH: 23
<212> TYPE: PRT
<213> ORGANISM: Artificial
<220> FEATURE:
<223> OTHER INFORMATION: Synthetically-generated peptide

<400> SEQUENCE: 49

Arg Glu Met Arg Gln Lys Ile Arg Ser His Ala His Ala Leu Leu Ala
1               5                   10                  15

Ala Asn Arg Phe Met Asp Met
            20

<210> SEQ ID NO 50
<211> LENGTH: 24
<212> TYPE: PRT
<213> ORGANISM: Artificial
<220> FEATURE:
<223> OTHER INFORMATION: Synthetically-generated peptide

<400> SEQUENCE: 50

Ala Arg Lys Glu Val Ile Arg Asn Lys Ile Arg Ala Ile Gly Lys Met
1               5                   10                  15

Ala Arg Val Phe Ser Val Leu Arg
            20

<210> SEQ ID NO 51
<211> LENGTH: 21
<212> TYPE: PRT
<213> ORGANISM: Artificial
<220> FEATURE:
<223> OTHER INFORMATION: Synthetically-generated peptide

<400> SEQUENCE: 51

Asn His Trp Gln Lys Ile Arg Thr Met Val Asn Leu Pro Val Ile Ser
1               5                   10                  15

Pro Phe Lys Ser Ser
            20

<210> SEQ ID NO 52
<211> LENGTH: 21
<212> TYPE: PRT
<213> ORGANISM: Artificial
<220> FEATURE:
<223> OTHER INFORMATION: Synthetically-generated peptide

<400> SEQUENCE: 52

Lys Arg Asn Lys Ala Leu Lys Lys Ile Arg Lys Leu Gln Lys Arg Gly
1               5                   10                  15

Leu Ile Gln Met Thr
            20
```

```
<210> SEQ ID NO 53
<211> LENGTH: 21
<212> TYPE: PRT
<213> ORGANISM: Artificial
<220> FEATURE:
<223> OTHER INFORMATION: Synthetically-generated peptide

<400> SEQUENCE: 53

Ser Ser Arg Arg Lys Trp Asn Lys Thr Gly His Ala Val Arg Ala Ile
1               5                   10                  15

Gly Arg Leu Ser Ser
            20

<210> SEQ ID NO 54
<211> LENGTH: 26
<212> TYPE: PRT
<213> ORGANISM: Artificial
<220> FEATURE:
<223> OTHER INFORMATION: Synthetically-generated peptide

<400> SEQUENCE: 54

Val Lys Leu Ile Pro Ser Leu Thr Thr Val Ile Leu Val Lys Ser Met
1               5                   10                  15

Leu Arg Lys Arg Ser Phe Gly Asn Pro Phe
            20                  25

<210> SEQ ID NO 55
<211> LENGTH: 18
<212> TYPE: PRT
<213> ORGANISM: Artificial
<220> FEATURE:
<223> OTHER INFORMATION: Synthetically-generated peptide

<400> SEQUENCE: 55

Gly Gly Ser Gly Gly Ser Gly Gly Ser Gly Gly Ser Gly Gly Ser Gly
1               5                   10                  15

Gly Ser
```